US007618816B2

(12) United States Patent
Mascarenhas

(10) Patent No.: US 7,618,816 B2
(45) Date of Patent: *Nov. 17, 2009

(54) METAL-BINDING THERAPEUTIC PEPTIDES

(75) Inventor: Desmond Mascarenhas, Los Altos Hills, CA (US)

(73) Assignee: Ontherix, Inc., Sunnyvale, CA (US)

( * ) Notice: Subject to any disclaimer, the term of this patent is extended or adjusted under 35 U.S.C. 154(b) by 246 days.

This patent is subject to a terminal disclaimer.

(21) Appl. No.: 11/595,367

(22) Filed: Nov. 8, 2006

(65) Prior Publication Data

US 2007/0134257 A1 Jun. 14, 2007

Related U.S. Application Data

(60) Provisional application No. 60/735,529, filed on Nov. 9, 2005, provisional application No. 60/789,100, filed on Apr. 3, 2006.

(51) Int. Cl.
*C12P 21/04* (2006.01)
*C12N 15/00* (2006.01)
*C07K 14/47* (2006.01)

(52) U.S. Cl. .................. 435/320.1; 536/23.4; 530/324; 435/69.7

(58) Field of Classification Search ........................ None
See application file for complete search history.

(56) References Cited

U.S. PATENT DOCUMENTS

| | | | |
|---|---|---|---|
| 4,683,202 | A | 7/1987 | Mullis |
| 5,824,467 | A | 10/1998 | Mascarenhas |
| 5,861,273 | A | 1/1999 | Olson et al. |
| 5,914,254 | A | 6/1999 | Mascarenhas et al. |
| 6,087,090 | A | 7/2000 | Mascarenhas |
| 6,251,639 | B1 | 6/2001 | Kurn |
| 6,630,160 | B1 | 10/2003 | Evans et al. |
| 6,692,918 | B2 | 2/2004 | Kurn |
| 6,914,049 | B2 | 7/2005 | Mascarenhas |
| 2003/0059430 | A1 | 3/2003 | Mascarenhas |
| 2003/0161829 | A1 | 8/2003 | Mascarenhas |
| 2003/0224990 | A1 | 12/2003 | Mascarenhas |
| 2008/0039393 | A1 | 2/2008 | Mascarenhas |
| 2008/0124346 | A1 | 5/2008 | Mascarenhas |
| 2009/0053203 | A1 | 2/2009 | Mascarenhas |

OTHER PUBLICATIONS

Alvarez Garcia, B. et al. (Nov. 2003). "High-Sensitivity C-Reactive Protein in High-Grade Carotid Stenosis: Risk Marker for Unstable Carotid Plaque," *Journal of Vascular Sungery* 38(5):1018-1024.
Ambrosini, G. et al. (Aug. 1997). "A Novel Anti-Apoptosis Gene, Survivin, Expressed in Cancer and Lymphoma," *Nature Medicine* 3(8):917-921.
Anderson, R. L. et al. (1981). "Temperature-Induced Homeoviscous Adaptation of Chinese Hamster Ovary Cells," *Biochimica et Biophysica Acta* 641:334-348.
Antman, K. H. et al. (Nov. 10, 1999). "High-Dose Chemotherapy for Breast Cancer," *JAMA* 282(18):1701-1703.
Arany, E. et al. (1996). "Rapid Clearance of Human Insulin-Like Growth Factor Binding Protein-3 From the Rat Circulation and Cellular Localization in Liver, Kidney and Stomach," *Growth Regulation* 6:32-41.
Barnes, J. A. et al. (2001). "Expression of Inducible Hsp70 Enhances the Proliferation of MCF-7 Breast Cancer Cells and Protects Against the Cytotoxic Effects of Hyperthermia," *Cell Stress Chaperones* 6(4):316-325.
Bosio, A. et al (2002). "Kinetics of Gene Expression Profiling in Swiss 3T3 Cells Exposed to Aqueous Extracts of Cigarette Smoke," *Carinogenesis* 23(5):741-748.
Butcher, J. (Feb. 2005). "Parkin Gene Therapy Could Treat Parkinson's Disease," *Lancet Neurol.* 4:82.
Butt, A. J. et al. (Jul. 2005). "Enhancement of Tumor Necrosis Factor-Alpha-Induced Growth Inhibition by Insulin-Like Growth Factor-Binding Proteins-5 (IGFBP-5), But Not IGFBP-3 in Human Breast Cancer Cells," *Endocrinology* 146(7):3113-3122.
Campisi, J. et al. (2003). "Stress-Induced Extracellular Hsp72 is a Functionally Significant Danger Signal to the Immune System," *Cell Stress & Chaperones* 8(3):272-286.
Chong, Y-P. et al. (Sep. 2005). "C-Terminal Src Kinase (CSK) and CSK-Homologous Kinase (CHK)—Endogenous Negative Regulators of Src-Family Protein Kinases," *Growth Factors* 23(3):233-244.
Ciocca, D. R. et al. (2002). "Hsp27 as a Prognostic and Predictive Factor in Cancer," in *Small Stress Proteins*. A.-P. Arrigo et al. eds., Springer-Verlag Berlin Heidelberg, pp. 205-218.
Ciocca, D. R. et al. (Oct. 6, 1993). "Biological and Clinical Implications of Heat Shock Protein 27000 (Hsp27): a Review," *Journal of National Cancer Institute* 85(19):1558-1570.
Clemmons, D. R. et al. (Jan. 2005). "Interaction Between Insulin-Like Growth Factor-I Receptor and alphaVbeta3 Integrin Linked Signaling Pathways: Cellular Responses to Changes in Multiple Signaling Inputs," *Molecular Endocrinology* 19(1):1-11.
Cornford, P. A. et al. (Dec. 15, 2000). "Heat Shock Protein Expression Independently Predicts Clinical Outcome in Prostate Cancer," *Cancer Research* 60:7099-7105.
Darios, F. et al. (2003). "Parkin Prevents Mitochondrial Swelling and Cytochrome C Release in Mitochondria-Dependent Cell Death," *Human Molecular Genetics* 12(5):517-526.
Dessein, P. H. et al. (2002). "Cardiovascular Risk in Rheumatoid Arthritis Versus Osteoarthritis: Acute Phase Response Related Decreased Insulin Sensitivity and High-Density Lipoprotein Cholesterol as Well as Clustering of Metabolic Syndrome Features in Rheumatoid Arthritis," *Arthritis Research* 4(5):1-6.
Driscoll, M. et al. (Mar. 2003). "Dying For a Cause: Invertebrate Genetics Takes on Human Neurodegeneration," *Nature Reviews Genetics* 4:181-194.
Escobar-Morreale, H. F. et al. (Feb. 2004). "Serum Interleukin-18 Concentrations Are Increased in the Polycystic Ovary Syndrome: Relationship to Insulin Resistance and to Obesity," *The Journal of Clinical Endocrinology & Metabolism* 89(2):806-811.

(Continued)

*Primary Examiner*—Marianne P Allen
(74) *Attorney, Agent, or Firm*—Morrison & Foerster LLP

(57) ABSTRACT

The present invention is related methods of delivering MBD peptide-linked agents into live cells. The methods described herein comprise contacting MBD peptide-linked agents to live cells under a condition of cellular stress. The methods of the invention may be used for therapeutic or diagnostic purposes.

12 Claims, 38 Drawing Sheets

OTHER PUBLICATIONS

Firestein, G. S. (May 15, 2003). "Evolving Concepts of Rheumatoid Arthritis," *Nature* 423:356-361.

Gargalovic, P. et al. (2003). "Cellular Apoptosis is Associated With Increased Caveolin-1 Expression in Macrophages," *Journal of Lipid Research* 44:1622-1632.

Gobert, A. P. et al. (Jan. 2, 2004). "Helicobacter Pylori Heat Shock Protein 60 Mediates Interleukin-6 Production by Macrophages via a Toll-Like Receptor (TLR)-2-,TLR-4-, and Myeloid Differentiation Factor 88-Independent Mechanism," *The Journal of Biological Chemistry* 279(1):245-250.

Goldberg, M. S. et al. (Oct. 31, 2003). "Parkin-Deficient Mice Exhibit Nigrostriatal Deficits but Not Loss of Dopaminergic Neurons," *The Journal of Biological Chemistry* 278(44):43628-43635.

Harkins, M. S. et al. (Dec. 2003). "Regulation of CD23 in the Chronic Inflammatory Response in Asthma: A Role For Interferon-y and Heat-Shock Protein 70 in the TH2 Environment," *Annals of Allergy Asthma & Immunology* 91:567-574.

Haywood, a. F. M. et al. (2004). "Parkin Counteracts Symptoms in a Drosophila Model of Parkinson's Disease," *BMC Neuroscience*. 5:1-12.

Hortobagyi, G. N. (Oct. 1, 1998). "Drug Therapy," *The New England Journal of Medicine* 339(14):974-984.

Jiang, H. et al. (2004). "Parkin Protects Human Dopaminergic Neuroblastoma Cells Against Dopamine-Induced Apoptosis," *Human Molecular Genetics* 13(16):1745-1754.

Kaarniranta, K. et al. (2002). "Neuronal Cells Show Regulatory Differences in the hsp70 Gene Response," *Molecular Brain Research* 101:136-140.

Kiss, A. L. et al. (2002). "Caveolae and Caveolin Isoforms in Rat Peritoneal Macrophages," *Micron* 33:75-93.

Lee, J-W. et al. (Feb. 2004). "Hypoxia-Inducible Factor (HIF-1) Alpha: Its Protein Stability and Biological Functions," *Experimental and Molecular Medicine* 36(1):1-12.

Li, F. et al. (Dec. 1999). "Pleiotropic Cell-Division Defects and Apoptosis Induced by Interference With Survivin Function," *Nat Cell Biol*. 1(8):461-466.

Lin, E. Y. et al. (2004). "Macrophages: Modulators of Breast Cancer Progression" *In Cancer and Inflammation Novartis Foundation Symposium* 256. John Wiley & Sons, Ltd. pp. 158-172.

Lipton, A. (2005). Business Briefing: North American Pharmacotherapy:109-112.

Lo Bianco, C. et al. (Dec. 14, 2004). "Lentiviral Vector Delivery of Parkin Prevents Dopaminergic Degeneration in an Alpha-Synuclein Rat Model of Parkinson's Disease," *Proceedings of the National Academy of Sciences of the United States of America*. 101(50):17510-17515.

Luscher, B. et al. (1999). "The Basic Region/Helix-Loop-Helix/Leucine Zipper Domain of Myc Proto-Oncoproteins: Function and Regulation," *Oncogene* 18:2955-2966.

Ma, J. et al. (Apr. 7, 2004). "A Prospective Study of Plasma C-Peptide and Colorectal Cancer Risk in Men," *Journal of the National Cancer Institute* 96(7):546-553.

Malin, A. et al. (Feb. 15, 2004). "Evaluation of the Synergistic Effect of Insulin Resistance and Insulin-Like Growth Factors on the Risk of Breast Carcinoma," *Cancer* 100(4):694-700.

Martin, C. A. et al. (2003). "Aberrant Extracellular and Dendritic Cell (DC) Surface Expression of Heat Shock Protein (hsp)70 in the Rheumatoid Joint: Possible Mechanisms of hsp/DC-Mediated Cross-Priming," *The Journal of Immunology* 171:5736-5742.

Michl, J. et al. (2006). "PNC-28, a p53-Derived Peptide That is Cytotoxic to Cancer Cells, Blocks Pancreatic Cancer Cell Growth in Vivo," *Int J Cancer*. 119:1557-1585.

Midgley, C. A. et al. (2000). "An N-Terminal p14 ARF Peptide Blocks Mdm2-Dependent Ubiquitination in Vitro and can Activate p53 in Vivo," *Oncogene* 19:2312-2323.

Mitsiades, C. S. et al. (2006). "Proteasome Inhibition as a New Therapeutic Principle in Hematological Malignancies," *Current Drug Targets* 7(10):1341-1347.

Morley, J. F. et al. (Feb. 2004). "Regulation of Longevity in Caenorhabeditis Elegans by Heat Shock Factor and Molecular Chaperones," *Molecular Biology of the Cell* 15:657-664.

Mulero, V. et al. (Oct. 1, 1999). "Regulation of Iron Metabolism in Murine J774 Macrophages: Rate of Nitric Oxide-Dependent and-Independent Pathways Following Activation With Gamma Interferon and Lipopolysaccharide," *Blood* 94(7):2383-2389.

Muqit, M. M. K. et al. (2004). "Parkin is Recruited into Aggresomes in a Stress-Specific Manner: Over-Expression of Parkin Reduces Aggresomes Formation but can be Disassociated From Parkin's Effect on Neuronal Survival," *Human Molecular Genetics* 13(1):117-135.

Nebbioso, A. et al. (Jan. 2005). "Tumor-Selective Action of HDAC Inhibitors Involves Trail Induction in Acute Myeloid Leukemia Cells," *Nature Medicine* 11(1):77-84.

Nitta-Komatsubara, Y. et al. (2000). "Altered Ischemic Induction of Immediate Early Gene and Heat Shock Protein 70 mRNAs After Preconditioning in Rat Hearts," *Life Sciences* 66(13):1261-1270.

Njemini, R. et al. (2003). "Elevated Serum Heat-Shock Protein 70 Levels in Patients With Acute Infection: Use of an Optimized Enzyme-Linked Immunosorbent Assay," *Scandinavian Journal of Immunology* 58:664-669.

Noguchi, T. et al. (2003). "Lymph Node Metastasis Could be Predicted by Evaluation of Macrophage Infiltration and hsp70 Expression in Superficial Carcinoma of the Esophagus," *Oncology Reports* 10:1161-1164.

Nylandsted, J. et al. (2000). "Heat Shock Protein 70 Is Required for the Survival of Cancer Cells" *In* Annals of the New York Academy of Sciences vol. 926: Mechanisms of Cell Death II The Third Annual Conferences of the International Cell Death Society. Z. Zakeri et al. eds., The New York Academy of Sciences, New York, New York, pp. 122-125.

Nylandsted, J. et al. (Dec. 15, 2002). "Eradication of Glioblastoma, and Breast and Colon Carcinoma Xenografts by Hsp70 Depletion," *Cancer Research* 62:7139-7142.

Oluwatosin-Chigbu, Y. et al. (2003). "Parkin Suppresses Wild-Type Alpha-Synuclein-Induced Toxicity in SHSY-5Y Cells," *Biochemical and Biophysical Research Communications* 309:679-684.

Perez, F. A. et al. (Feb. 8, 2005). "Parkin-Deficient Mice Are Not a Robust Model of Parkinsonism," *Proceedings of the National Academy of Sciences of the United States of America* 102(6):2174-2179.

Petropavlovaskaia, M. et al. (2006). "Development of an in Vitro Pancreatic Tissue Model to Study Regulation of Islet Neogenesis Associated Protein Expression," *Journal of Endocrinology* 191:65-81.

Purcell, A. W. et al. (2003). "Association of Stress Proteins With Autoantigens: A Possible Mechanism for Triggering Autoimmunity," *Clinical and Experimental Immunology* 132:193-200.

Rao, R. D. et al. (Oct. 2005). "Disruption of Parallel and Converging Signaling Pathways Contributes to the Synergistic Antitumor Effects of Simultaneous mTDR and EGFR Inhibition in GBM Cells," *Neoplastia* 7(10):921-929.

Rashmi, R. et al. (2004). "Ectopic Expression of Hsp70 Confers Resistance and Silencing its Expression Sensitizes Human Colon Cancer Cells to Curcumin-Induced Apoptosis," *Carcinogenesis* 25(2):179-187.

Ricaniadis, N. et al. (Feb. 2001). "Long-Term Prognostic Significance of HSP-70, C-Myc and HLA-DR Expression in Patients With Malignant Melanoma," *European Journal of Surgical Oncology* 27:88-93.

Rosenberg, L. (1998). "Induction of Islet Cell Neogenesis in the Adult Pancreas: The Partial Duct Obstruction Model," *Microscopy Research and Technique* 43:337-346.

Scharf, J-G. et al. (Apr. 1996). "Synthesis of Insulinlike Growth Factor Binding Proteins and of the Acid-Labile Subunit in Primary Cultures of Rat Hepatocytes, of Kupffer Cells, and in Cocultures: Regulation by Insulin, Insulinlike Growth Factor, and Growth Hormone," *Hepatology* 23(4):818-827.

Schiaffonati, L. et al. (1997). "Gene Expression in Liver After Toxic Injury: Analysis of Heat Shock Response and Oxidative Stress-Inducible Genes," *Liver*. 17:183-191.

Singh, B. et al. (Jan. 2, 2004). "Insulin-Like Growth Factor-Independent Effects Mediated by a C-Terminal Metal-Binding Domain of Insulin-Like Growth Factor Binding Protein-3," *The Journal of Biological Chemistry* 279(1):477-487.

Stohwasser, R. et al. (Jan. 2003). "Hepatitis B Virus HBx Peptide 116-138 and Proteasome Activator PA28 Compete for Binding to the Proteasome Alpha 4/MC6 Subunit," *Biol. Chem.* 384:39-49.

Strik, H. M. et al. (2000). "Heat Shock Protein Expression in Human Gliomas," *Anticancer Research* 20:4457-4462.

Strnad, J. et al. (2006). "NEMO Binding Domain of IKK-2 Encompasses Amino Acids 735-745," *Journal of Molecular Recognition* 19:227-233.

Sun, C. et al (2005). "Solution Structure of Human Survivin and Its Binding Interface With Smac/Diablo," *Biochemistry* 44(1):11-17.

Szabo, S. J. et al. (Mar. 17, 2000). "A Novel Transcription Factor, T-Bet, Directs Th1 Lineage Commitment," *Cell* 100:655-669.

Tai, L-J. et al. (Jan. 4, 2002). "Structure-Function Analysis of the Heat Shock Factor-Binding Protein Reveals a Protein Composed Solely of a Highly Conserved and Dynamic Coiled-Coil Trimerization Domain," *The Journal of Biological Chemistry* 227(1):735-745.

Takada, Y. et al. (Apr. 9, 2004). "Identification of a p65 Peptide That Selectively Inhibits NF-kB Activation Induced by Various Inflammatory Stimuli and Its Role in Down-Regulation of NF-kB-Mediated Gene Expression and Up-Regulation of Apoptosis," *The Journal of Biological Chemistry* 279(15):15096-15104.

Valles, P. et al. (2003). "Heat Shock Proteins HSP27 and HSP70 in Unilateral Obstructed Kidneys," *Pediatr Nephrol* 18:527-535.

Volloch, V. Z. et al. (1999). "Oncogenic Potential of Hsp72," *Oncogene* 18:3648-3651.

Wang, G. et al. (2004). "Essential Requirement for Both hsf1 and hsf2 Transcriptional Activity in Spermatogenesis and Male Fertility," *Genesis* 38:66-80.

Wang, J-H. et al. (2002). "Blocking HSF1 by Dominant-Negative Mutant to Sensitize Tumor Cells to Hyperthermia," *Biochemical and Biophysical Research Communications* 290(5):1454-1461.

Weisberg, S. P. et al. (Dec. 2003). "Obesity is Associated With Macrophage Accumulation in Adipose Tissue," *The Journal of Clinical Investigation* 112(12):1796-1808.

Xu, H. et al. (Dec. 2003). "Chronic Inflammation in Fat Plays a Crucial Role in the Development of Obesity-Related Insulin Resistance," *The Journal of Clinical Investigation* 112(12):1821-1830.

Yamada, M. et al (Feb. 2005). "Parkin Gene Therapy for Alpha-Synucleinopathy: A Rat Model of Parkinson's Disease," *Human Gene Therapy* 16:262-270.

Yamaoka, T. et al. (1999). "Development of Pancreatic Islets (Review)," *International Journal of Molecular Medicine* 3:247-261.

Yang, G. et al. (Mar. 15, 2004). "Reduced Infiltration of Class A Scavenger Receptor Positive Antigen-Presenting Cells Is Associated With Prostate Cancer Progression," *Cancer Research* 64:2076-2082.

Yano, T. (1999). "Activation of Extracellular Signal-Regulated Kinase in Lung Tissues of Mice Treated With Carcinogen," *Life Sciences* 64(4):229-236.

Zhang, R. et al. (2004). "Fluorescence Polarization Assay and Inhibitor Design for MDM2/p53 Interaction," *Analytical Biochemistry* 331:138-146.

Zimmermann, E. M. et al. (2000). "Cell-Specific Localization of Insulin-Like Growth Factor Binding Protein mRNAs in Rat Liver," *Am J. Physiol. Gastrointest. Liver Physiol.* 278:G447-G457.

Zou, Y. et al. (Dec. 16, 2003). "Heat Shock Transcription Factor 1 Protects Cardiomyocytes From Ischemia/Reperfusion Injury," *Circulation* 108:3024-3030.

Cao, G. et al. (Jul. 1, 2002). "In Vivo Delivery of a Bcl-xL Fusion Protein Containing the TAT Protein Transduction Domain Protects Against Ischemic Brain Injury and Neuronal Apoptosis," *The Journal of Neuroscience* 22(13):5423-5431.

Porrini, M. et al. (Aug. 2005). "Promises and Perils of Lycopene/Tomato Supplementation and Cancer Prevention: What are Typical Lycopene Intakes?" *The Journal of Nutrition* 135:2042S-2045S.

Davé, S.H. et al. (Dec. 1, 2007). "Amelioration of Chronic Murine Colitis by Peptide-Mediated Transduction of the Ikb Kinase Inhibitor NEMO Binding Domain Peptide," *The Journal of Immunology* 179(11):7852-7859.

Goldin, A. et al. (2006). "Advanced Glycation End Products: Sparking the Development of Diabetic Vascular Injury," *Circulation* 114:597-605.

Hayden, M.S. et al. (2004). "Signaling to NF-kB," *Genes and Development* 18:2195-2224.

Johnstone, C.N. et al. (Mar. 2005). "*PRR5* Encodes a Conserved Proline-Rich Protein Predominant in Kidney: Analysis of Genomic Organization, Expression, and Mutation Status in Breast and Colorectal Carcinomas," *Genomics* 85(3):338-351.

Koyama, H. et al. (Nov.-Dec. 2007). "Rage and Soluble RAGE: Potential Therapeutic Targets for Cardiovascular Diseases," *Mol. Med.* 13(11-12):625-635.

Li, G.C. et al. (Dec. 1980). "A Proposed Operational Model of Thermotolerance Based on Effects of Nutrients and the Initial Treatment Temperature," *Cancer Res.* 40:4501-4508.

Peterson, L.E. (2003). "Partitioning Large-Sample Microarray-Based Gene Expression Profiles using Principal Components Analysis," *Comput. Methods Programs Biomed.* 70:107-119.

Santa Cruz Biotechnology, Inc. (2007). Product Search: IKK Antibody/IKK Antibodies, located at <http://www.scbt.com/table.php?table=ikk>, last visited on Mar. 13, 2009, two pages.

Tan, A.L.Y. et al. (Mar. 2007). "AGE, RAGE, and ROS in Diabetic Nephropathy," *Semin. Nephrol.* 27(2):130-143.

Tas, S.W. et al. (2006, e-pub. May 9, 2006). "Local Treatment with the Selective IkB Kinase βInhibitor NEMO-Binding Domain Peptide Ameliorates Synovial Inflammation," *Arthritis Research & Therapy* 8:1-9.

Thedieck, K. et al. (Nov. 2007). "PRAS40 and PRR5-Like Protein Are New mTOR Interactors that Regulate Apoptosis," *PLoS ONE* 2(11):e1217.

Tsilibary, E.C. et al. (Jul. 2003). "Microvascular Basement Membranes in Diabetes Mellitus," *J. Pathol.* 200(4):537-546.

Tuttle, K.R. et al. (Sep. 2003). "A Novel Potential Therapy for Diabetic Nephropathy and Vascular Complications: Protein Kinase C β Inhibition," *Am. J. Kidney Dis.* 42(3):456-465.

Woo, S-Y. et al. (Aug. 31, 2007). "PRR5, a Novel Component of mTOR Complex 2, Regulates Platelet-derived Growth Factor Receptor B Expression and Signaling," *J. Biol. Chem.* 282(35):25604-25612.

Yamagishi, S. et al. (Oct. 2007). "Kinetics, Role and Therapeutic Implications of Endogenous Soluble Form of Receptor for Advanced Glycation end Products (sRAGE) in Diabetes," *Curr. Drug Targets* 8(10):1138-1143.

* $p<0.05$

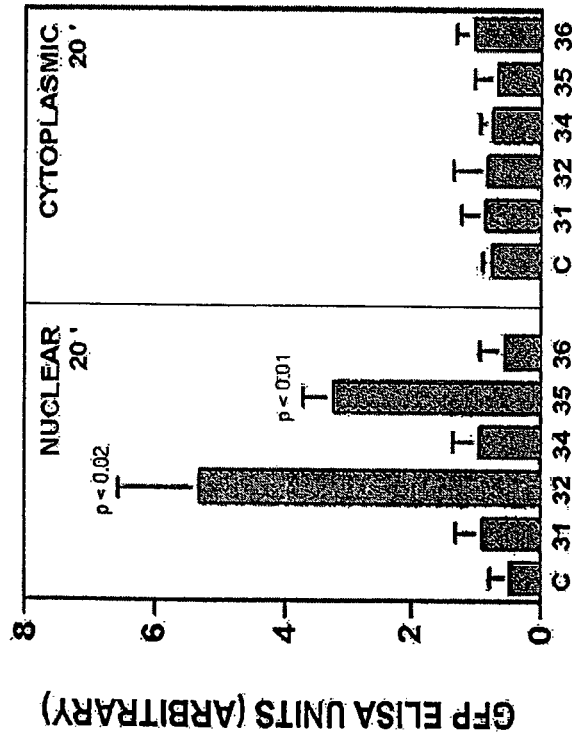
Figure 3. Nuclear Uptake of MBD-GFPs
MBD31: KKGHAKDSQRYKVDESQS
MBD32: KKGFYKKKQCRPSKGRKRGFCW
MBD34: KKGFYKKKQ
MBD35: QCRPSKGRKRGFCW
MBD36: KKGFYKKKQCRPSKGRKR

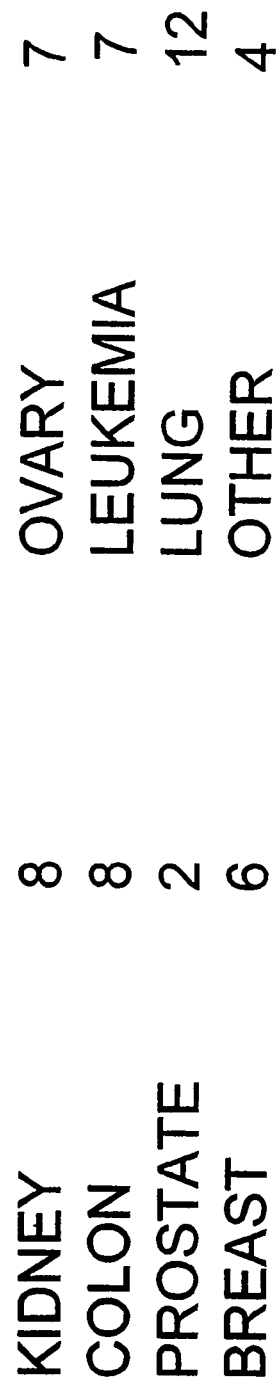
Figure 4. Uptake of MBD-mobilized SA-HRP by tumor cell lines
- 48 tumor cell lines obtained from NCI, ATCC
- passaged in RPMI1640+10% FBS+10 uM $FeCl_2$
- SA-HRP::MBD peptide uptake was quantified
- nuclear / cytoplasmic localization was determined
| | | | |
|---|---|---|---|
| KIDNEY | 8 | OVARY | 7 |
| COLON | 8 | LEUKEMIA | 7 |
| PROSTATE | 2 | LUNG | 12 |
| BREAST | 6 | OTHER | 4 |

Figure 5. Cell Internalization of MBD-mobilized SA-HRP in tumor cell lines

| TISSUE | HIGH-UPTAKE | LOW-UPTAKE |
|---|---|---|
| Prostate | PC-3 | *DU-145* |
| Colon | HT-29 | HCT-15 |
| Lung | NCI-H23 | HOP-62 |
| Kidney | A498 | UO-31 |
| Ovary | OVCAR-8 | OVCAR-5 |
| Breast | MCF-7 | HS-578T |
| Leukemia | CCRF-CEM | K562 |

Figure 6. Cell internalization of MBD-mobilized SA-HRP in tumor cell lines

| GENE CATEGORY | % ARRAY (n=1129) | HIGH vs LOW MBD UPTAKE | |
|---|---|---|---|
| | | UP-REG (n=32) | DN-REG (n=32) |
| TRANSCRIPTION FACTORS | 9.7 | 40.6 | 0 |
| INTRACELLULAR PROTEINS | 18.3 | 25.0 | 0 |
| SIGNAL TRANSDUCTION (I) | 32.6 | 9.4 | 0 |
| CELL-CYCLE, DNA REPAIR | 10.6 | 0 | 0 |
| ECM-RELATED | 13.6 | 3.1 | 68.8 |
| RECEPTORS / LIGANDS | 15.2 | 9.4 | 31.2 |

(top and bottom 3% differentially regulated genes)

Figure 7. Up-regulated genes correlated to MBD-mobilized HRP internalization in tumor cell lines

| | | |
|---|---|---|
| GDF15 | CEBPB | CREM |
| HSP70 | BRF2 | NEK3 |
| NFkB2 | BAX | PSMA4 |
| PSMB9 | GADD153 | RELB |
| ATF3 | CXCR4 | |
| JUNB | SRC | |
| PSMB10 | IRF1 | |
| | JUN | |
| | HSP70B' | |

84% of up-regulated genes are associated with cellular stress responses (they are listed here)

Figure 8. Cell Internalization of MBD-mobilized SA-HRP in tumor cell lines
DOWN-REGULATED GENES
IL6, IL1B, TGFB2
UPA, MMP2, LOX, PAI1
TSP1, SPARC, FBN1, DCN, COL1A1, COL4A1, COL4A2, COL5A1, COL5A2, COL6A2, COL6A3, COL7A1, COL8A1
(all secreted gene products)

Figure 9. Cell Internalization of MBD-mobilized SA-HRP in tumor cell lines

GENE EXPRESSION CORRELATES

| GENE | PR* | CO* | LU* | KI* | BR* |
|---|---|---|---|---|---|
| GDF-15 | 104.0 | 8.3 | 15.0 | 17.7 | 2.8 |
| IRF1 | 7.2 | 7.3 | 1.1 | 3.2 | 1.3 |
| HSP1A1 | 2.4 | 1.3 | 3.8 | 3.7 | 10.1 |
| JUNB | 9.0 | 0.9 | 6.1 | 3.2 | 10.0 |
| TGFB2 | 0.24 | 0.85 | 0.08 | 0.71 | 0.07 |
| IL6 | 1.05 | 0.67 | 0.26 | 0.21 | 0.04 |
| SPARC | 9.67 | 0.67 | 0.02 | 0.23 | 0.00 |

(* the –fold expression difference in pairwise comparisons; PR=prostate; CO=colon; LU=lung; KI=kidney; BR=breast)

Figure 10. Cell Internalization of MBD-mobilized SA-HRP in tumor cell lines

PROTEIN CORRELATES

*Membrane Cross-Link*
- transferrin receptor 1
- caveolin 1
- integrin alpha v
- integrin alpha 2
- integrin alpha 5
- integrin alpha 6
- integrin beta 1
- integrin beta 3
- integrin beta 5

*Intracellular*
- PCNA
- hsp 70
- grp 78/94
- CXCR4

*Extracellular*
- hsp 70
- GDF-15

GDF-15 / MIC-1 / PLAB

GDF-15 / MIC-1 / PLAB

Figure 13. Some candidate cellular stress response programs

- ENDOPLASMIC RETICULUM
- METABOLIC / OXIDATIVE
- THERMAL
- NUTRITIONAL
- SENESCENCE
- CYTOKINE / INFLAMMATORY
- ISCHEMIC / ANOXIC
- MECHANICAL
- CHEMICAL
- OSMOTIC
- GLYCEMIC

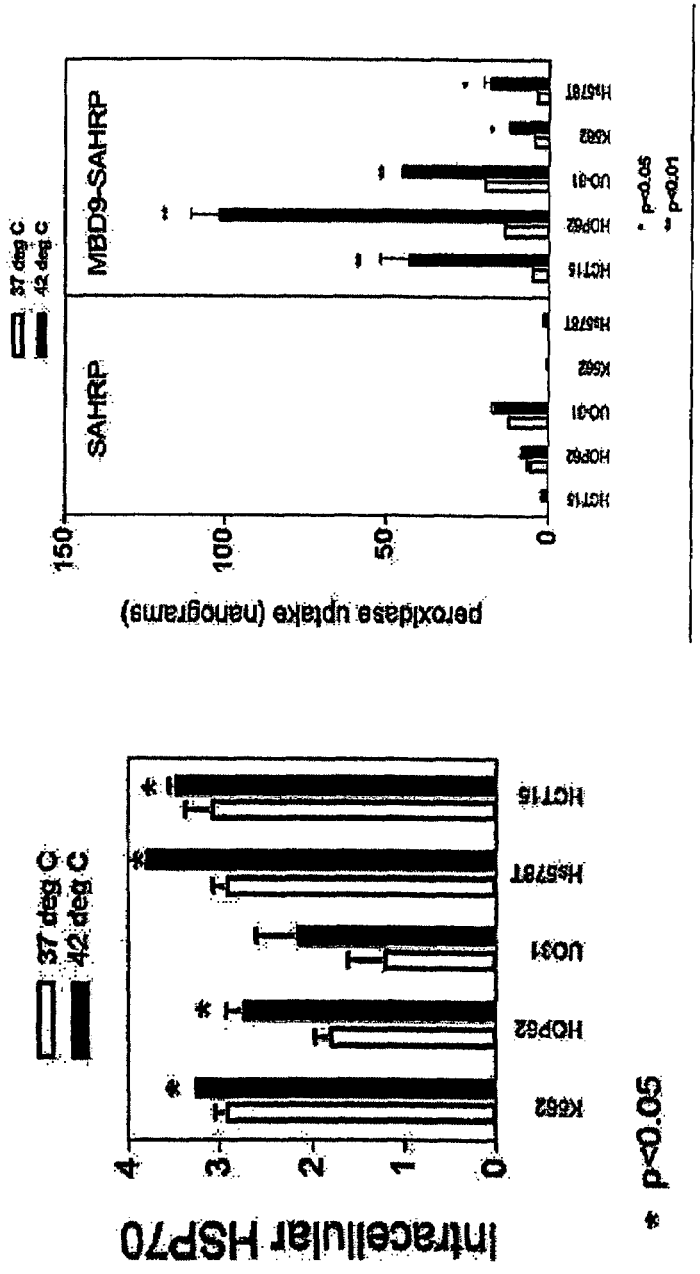
Figure 14. Cell Internalization of MBD-mobilized SA-HRP in tumor cell lines

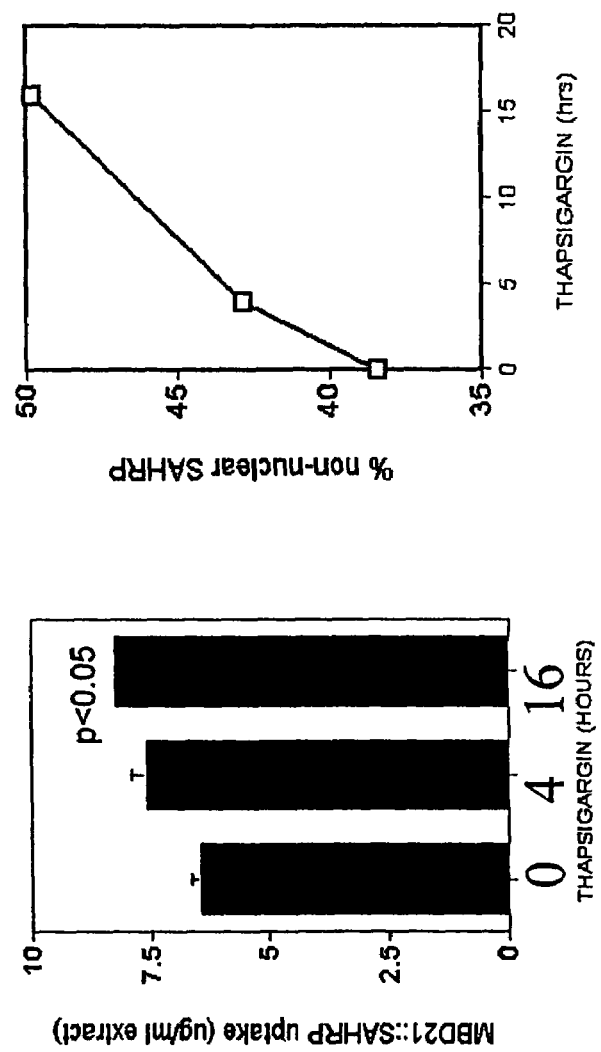
Figure 15. Cell Internalization of MBD-mobilized SA-HRP in UO-31 cell line

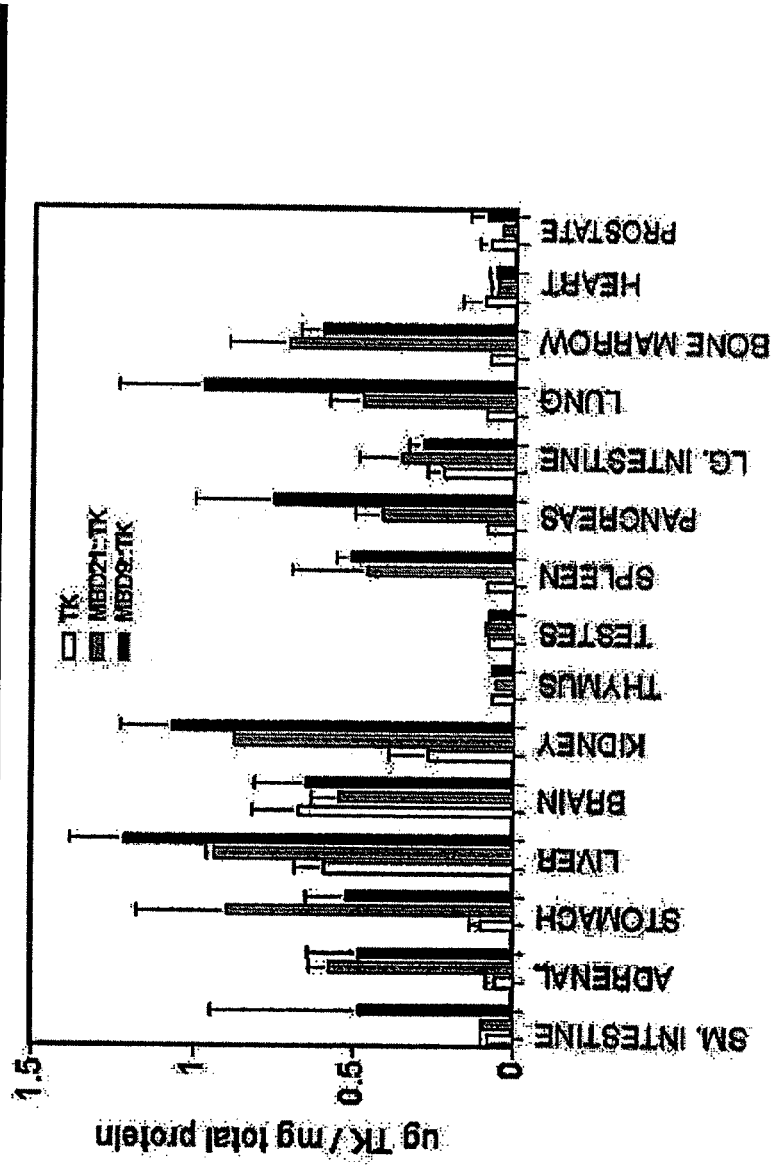
Figure 16. Biodistribution of MBD-tagged proteins systemically administered to rats *in vivo*

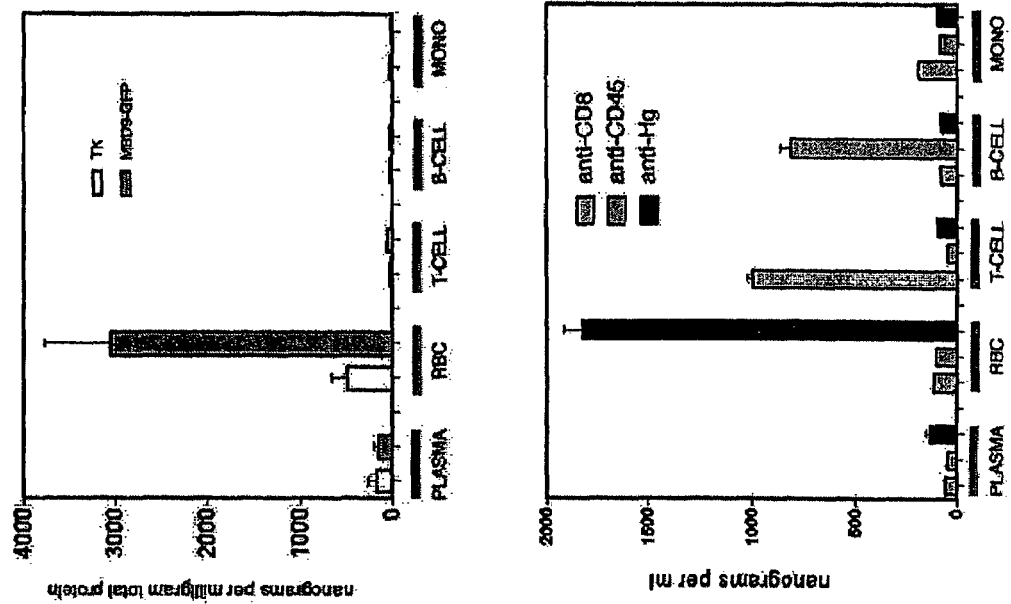
Figure 17. Cell association of MBD-tagged proteins systemically administered in vivo
CONTROL RATS

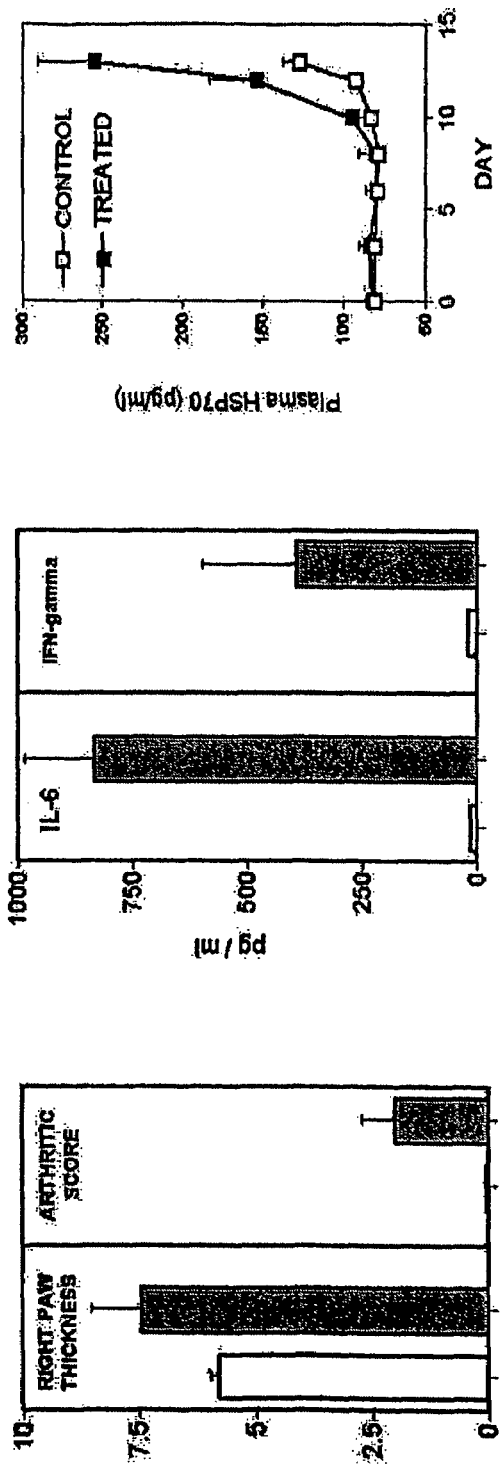
Figure 18. Markers of disease progression in a rat adjuvant arthritis model

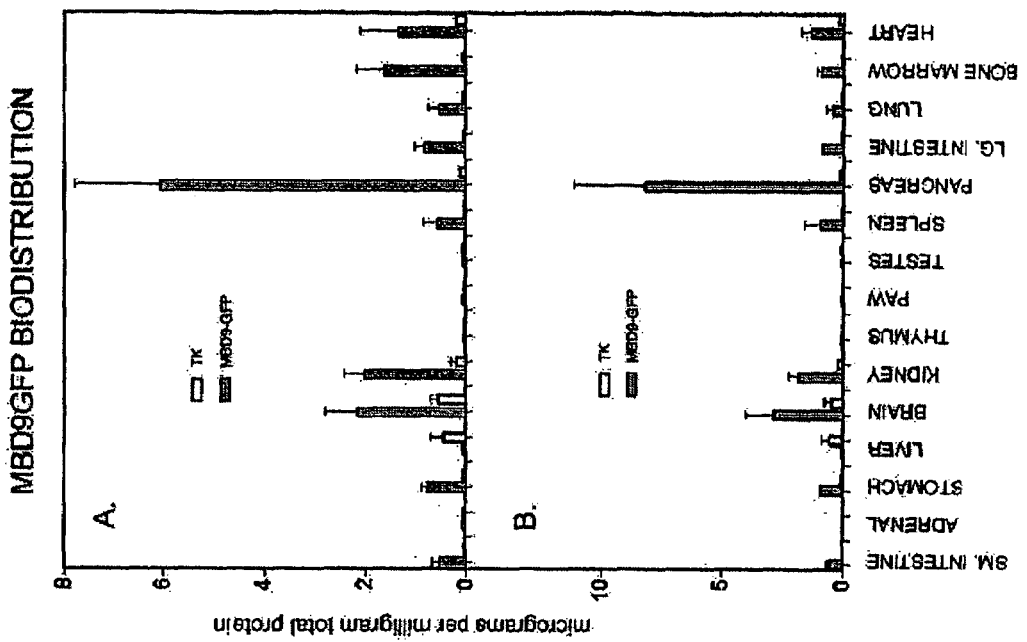
Figure 19. Cell Internalization of MBD-tagged proteins systemically administered *in vivo*
INFLAMMATORY STRESS (ARTHRITIS)
A. CONTROL
B. ARTHRITIC

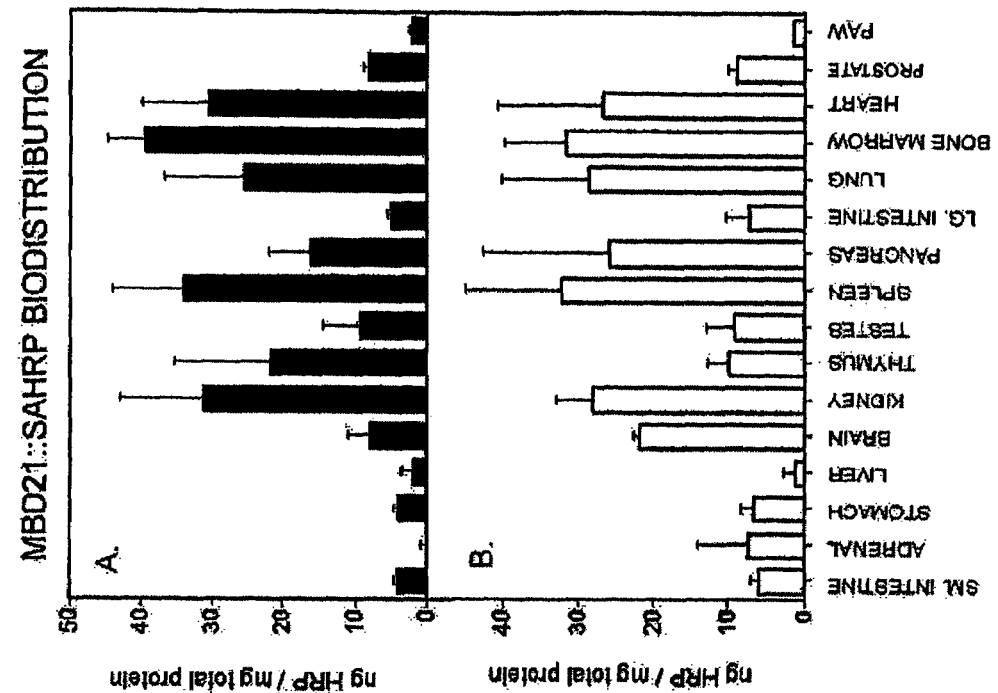
Figure 20. Cell Internalization of MBD-tagged proteins systemically administered *in vivo*
INFLAMMATORY STRESS (ARTHRITIS)
A. CONTROL
B. ARTHRITIC

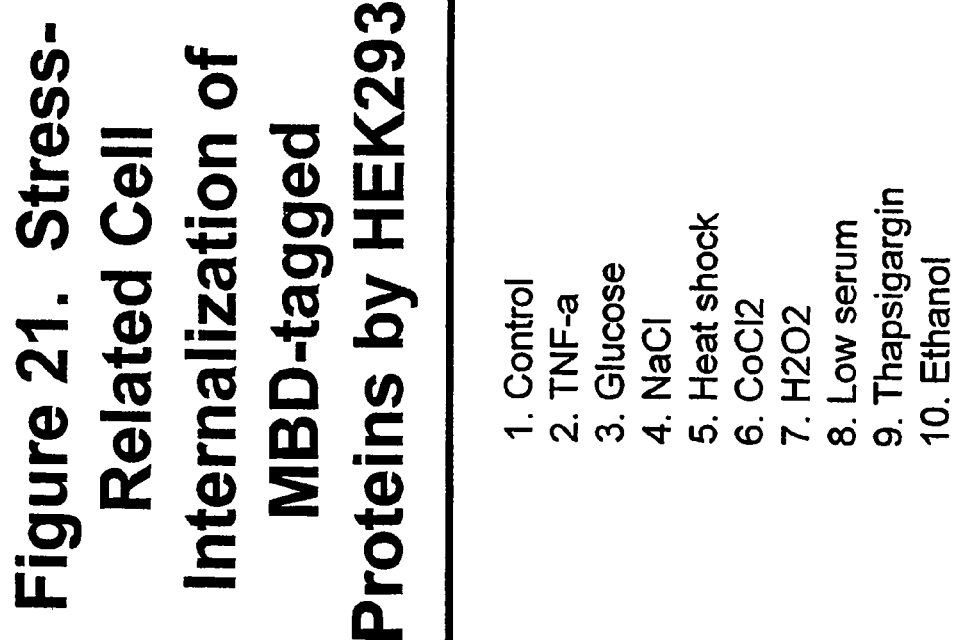
Figure 21. Stress-Related Cell Internalization of MBD-tagged Proteins by HEK293
1. Control
2. TNF-a
3. Glucose
4. NaCl
5. Heat shock
6. CoCl2
7. H2O2
8. Low serum
9. Thapsigargin
10. Ethanol

Figure 22. Stress-Related Internalization of MBD-tagged Proteins by PC12 Cells
Y-axis units = ng HRP
CON = CONTROL
MPP+ = MPTP
6OHDA = 6OHDA
C = cytoplasmic
N = nuclear Figure 23. All peptides showed significantly different effects from control on cells except for peptides 5 and 6 on Hst578T and MDA-MB435 cells.
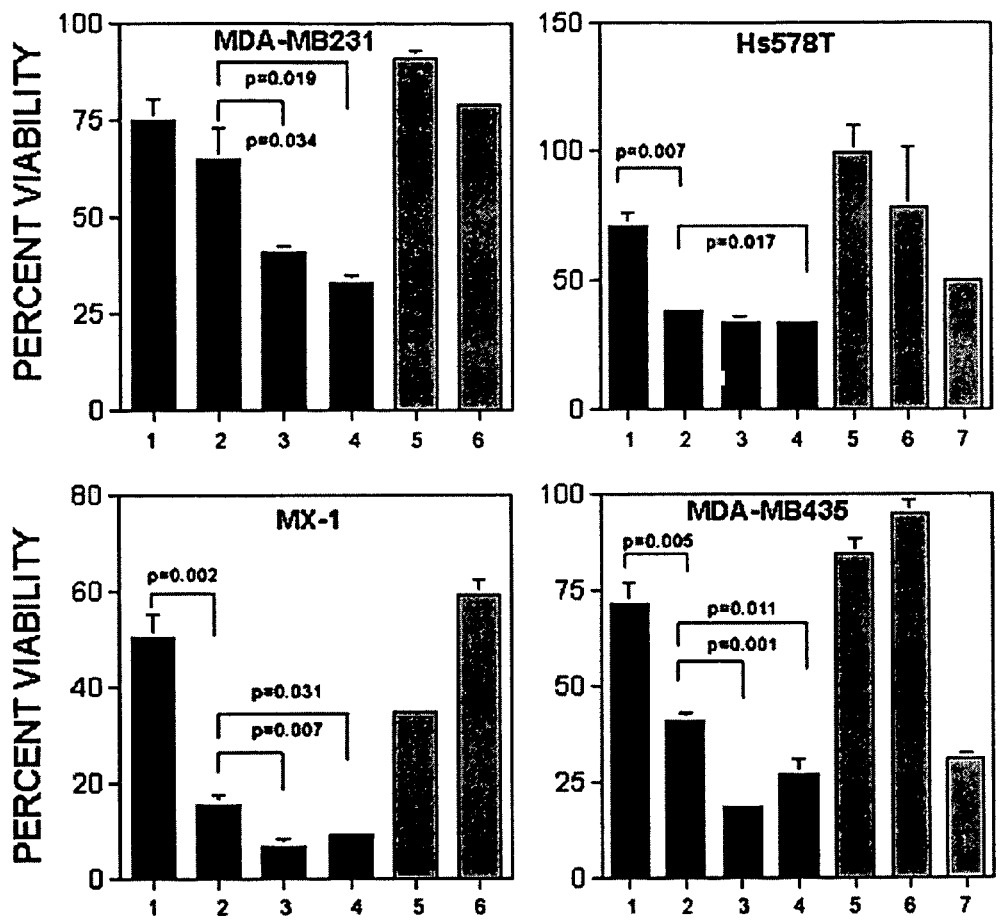
1: PNC-28; 2: PEP-1; 3: PEP-2; 4: PEP-3; 5: NFKB; 6: NEMO; 7: CSK Figure 24. Peptides added to cells: 1: PEP-1; 2: PEP-2; 3: PEP-3; 4: PKCI; 5: CSK; 6: VIVIT; 7: NFKB; 8: CTLA4; 9: CD28; 10: NEMO; 11: MAN
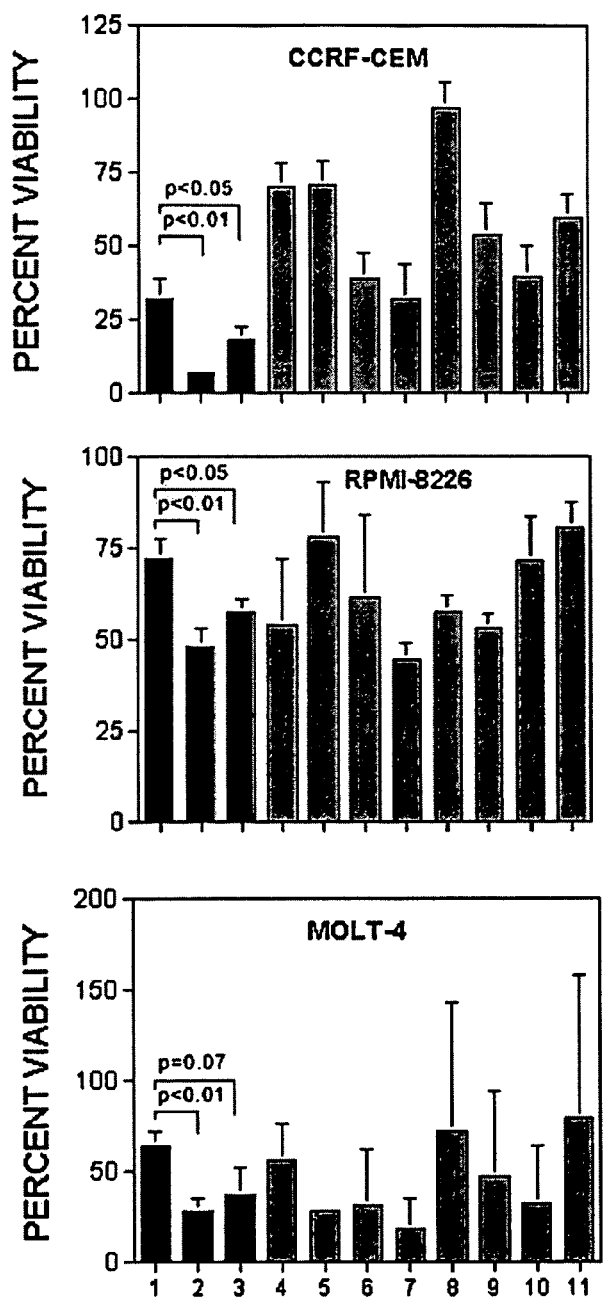

Figure 25. Synergy with nutritional stress on MCF-7 breast cancer cells. PEP-3 was added at 25 ug/ml.
(A)
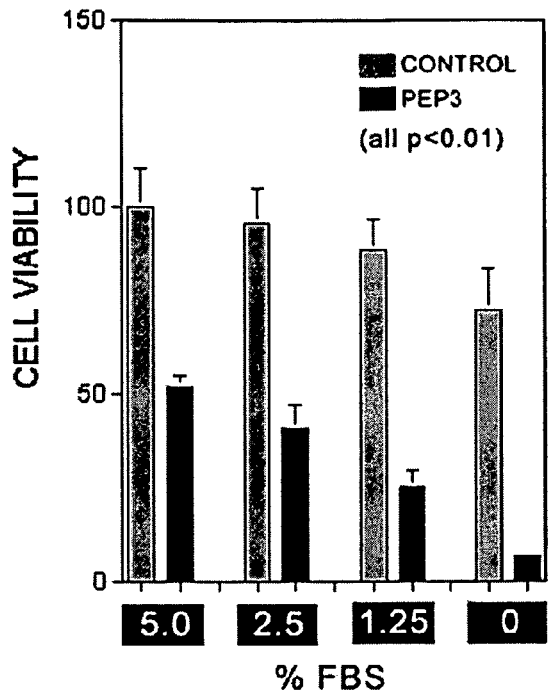
(B)
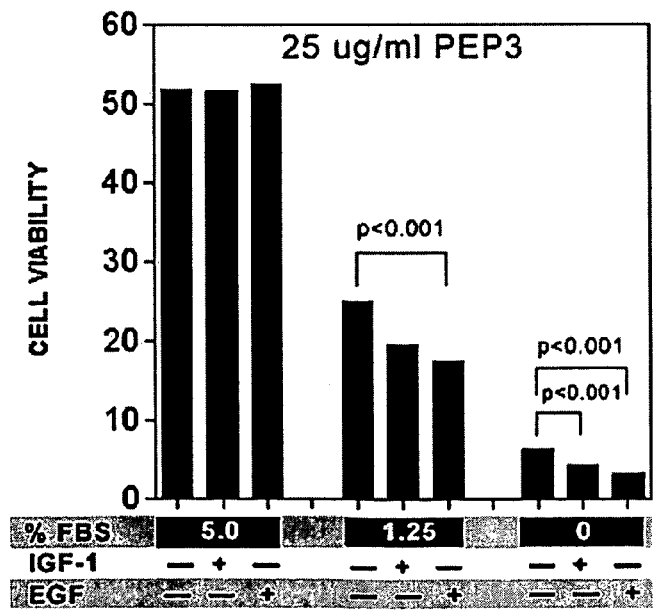

Figure 26. Synergy with chemotherapeutic agents in MCF-7 breast cancer cells. Peptides were added at 25 ug/ml. Tamoxifen (1 mM; TAM) or paclitaxel (0.1 ug/ml; TAX) were added simultaneously.
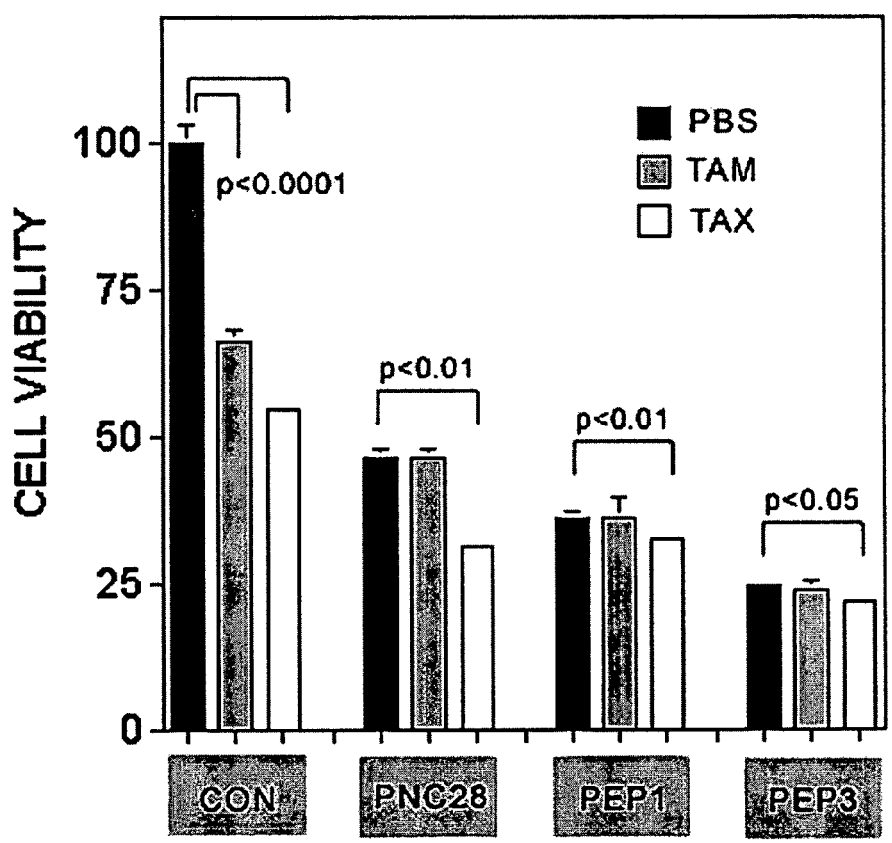

Mouse model of human leukemia

Figure 28. MBD-Mediated Antibody Uptake.
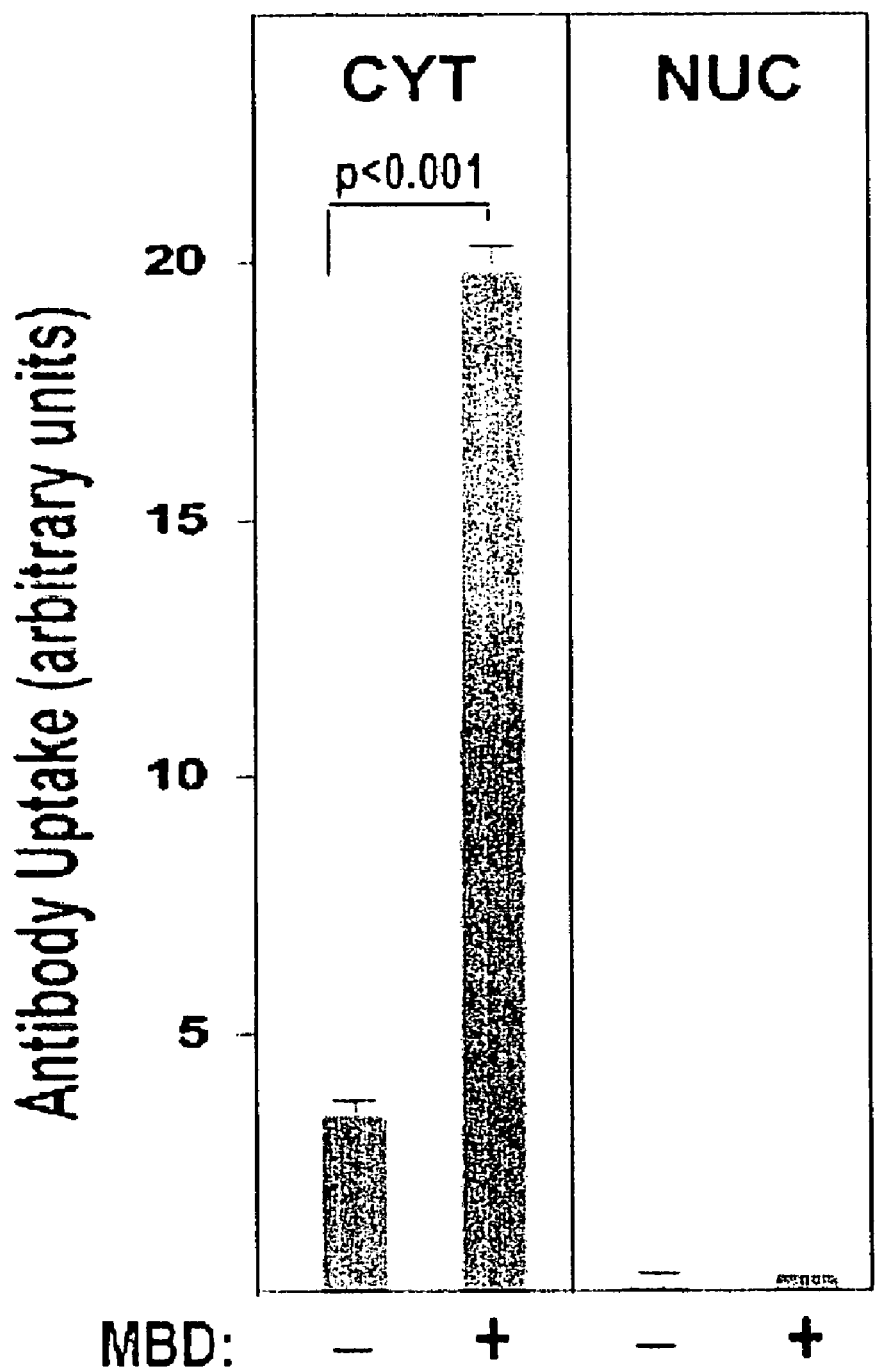

Figure 29. MBD-tagged HRP is preferentially taken up by cancer cells.
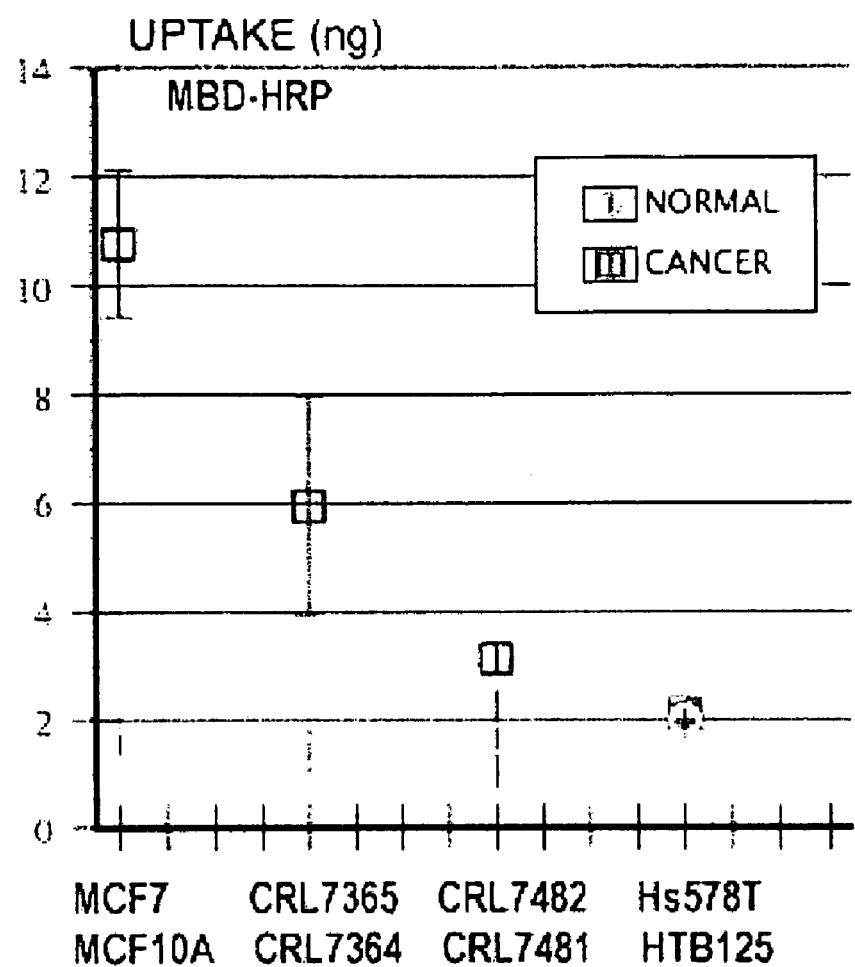

Figure 30. Combinatorial power of therapeutic peptide enhancers.
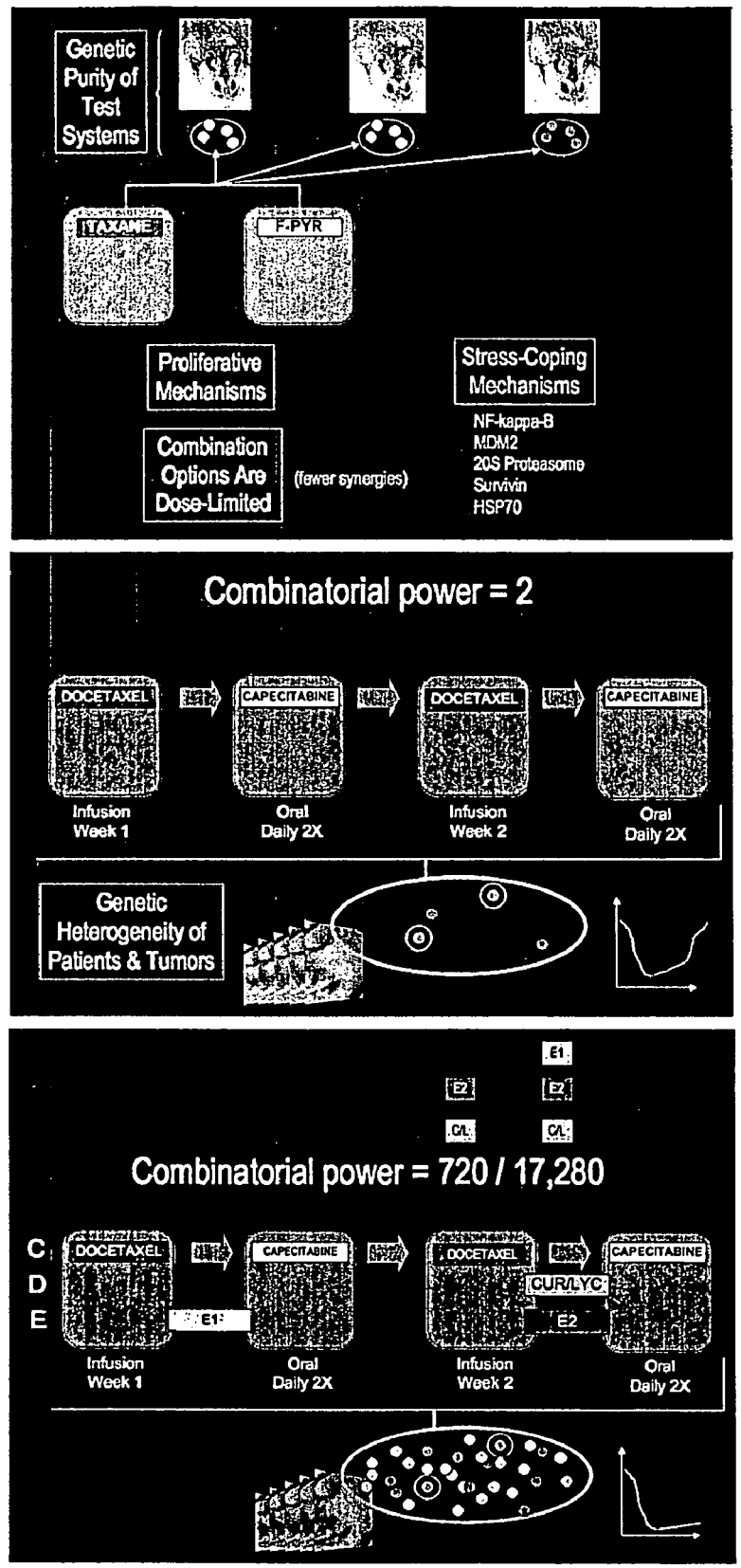

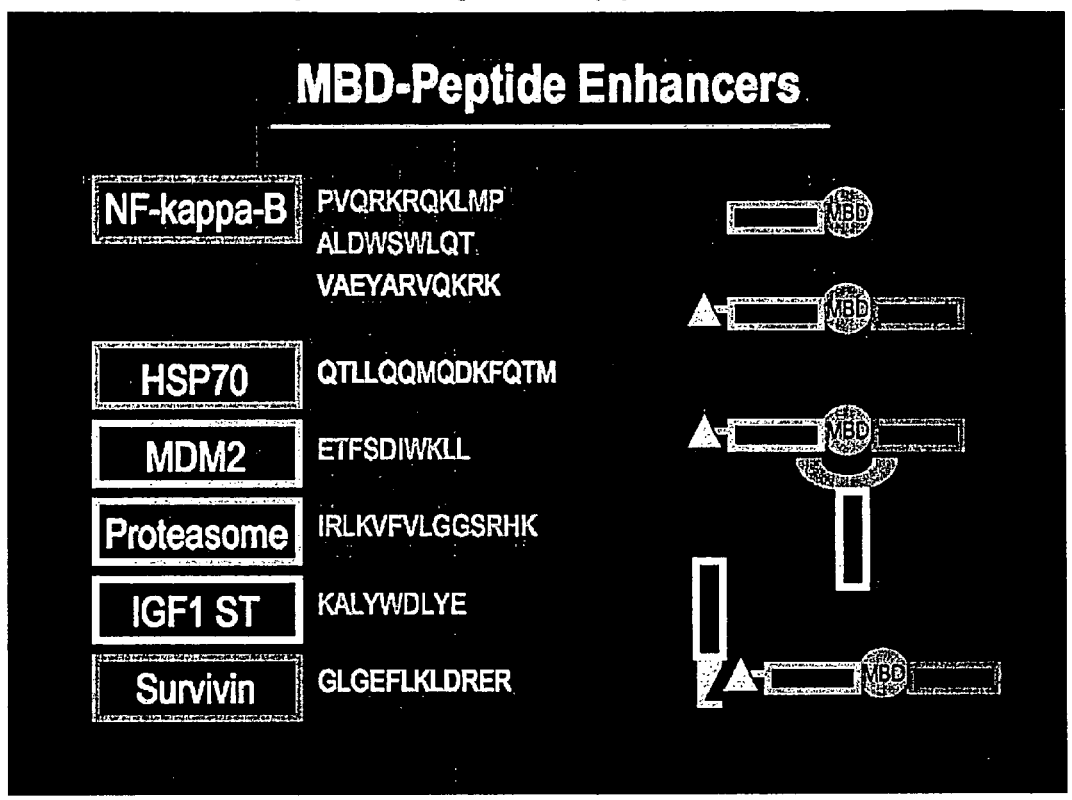
Figure 31. Configurations of peptide enhancers.

Figure 32. Broad spectrum of intrinsic activity of peptide enhancers:

| PEPTIDE | PROSTATE | | | BREAST | | | | | | LEUKEMIA | | | |
|---|---|---|---|---|---|---|---|---|---|---|---|---|---|
| | PC3 | LNCap | DU145 | MCF7 | MDA 231 | MDA 435 | Hs 578T | CRL 7345 | CRL 7365 | CCRF-CEM | MOLT-4 | SR | RPMI-8826 |
| CSK | + | + | + | +++ | | | + | + | + | + | + | | |
| NFKB | +/- | +/- | +/- | ++ | + | ++ | ++ | NT | NT | ++ | ++ | | + |
| NEMO | +++ | +++ | +++ | + | + | + | + | ++ | ++ | | | ++ | |
| VIVIT | ++ | + | + | NT | NT | NT | NT | ++ | + | ++ | ++ | ++ | ++ |
| HSBP1 | | | | + | | | + | ++ | ++ | | | | |
| HSBP2 | + | +/- | +/- | + | | + | ++++ | NT | NT | + | | | |
| PEP2 | | | | ++++ | ++++ | ++++ | + | + | NT | +++ | +++ | +++ | +++ |
| PEP3 | +++ | +++ | +++ | ++++ | ++++ | ++++ | ++++ | ++ | ++ | ++ | ++ | ++ | |
| MSURVN | + | + | + | ++ | + | + | + | ++ | ++ | | | | |
| MDOKB3 | | | | + | | + | + | NT | NT | | | | |
| MDOKSH | | | | ++ | | | + | - | - | ++ | | | |

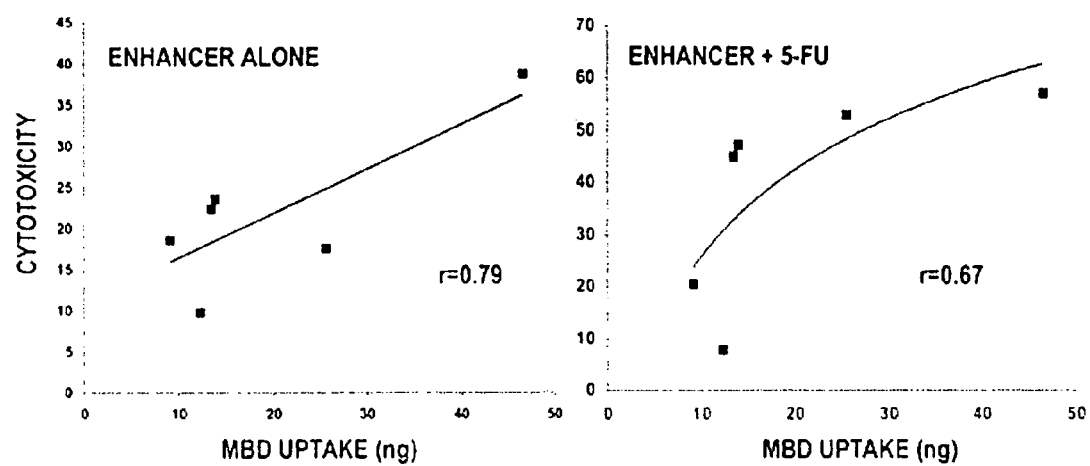
Figure 33. Enhancer effects are proportional to uptake.

Figure 34. Broad spectrum of enhancement in breast cancer.
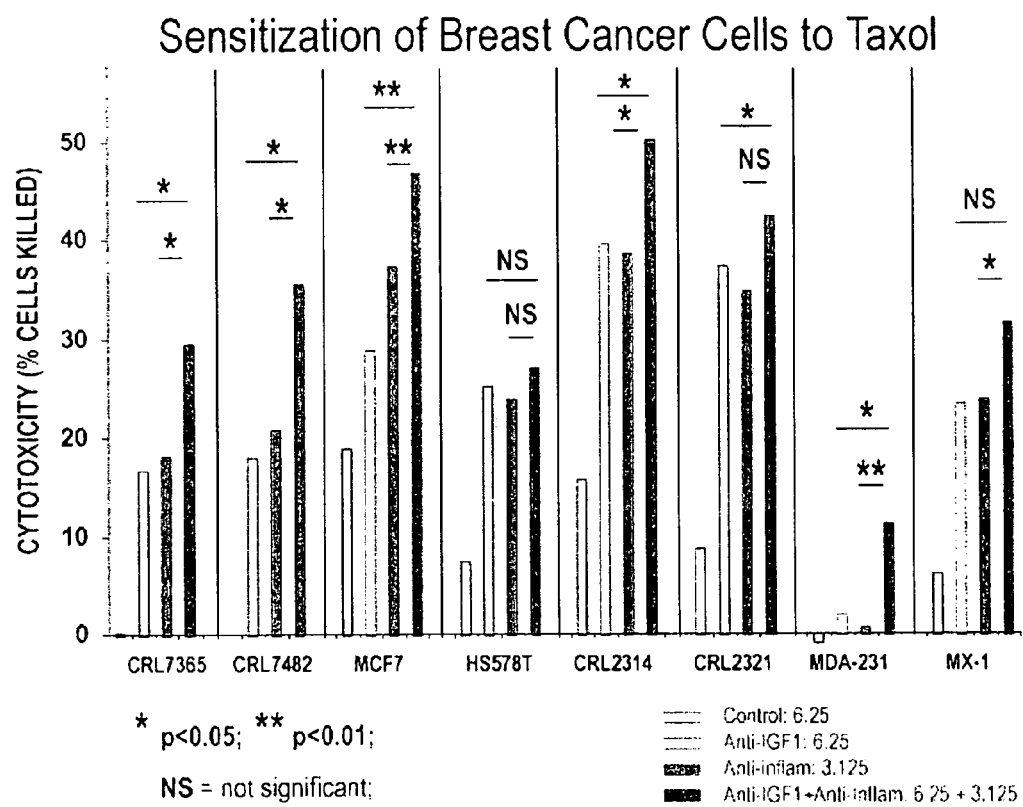

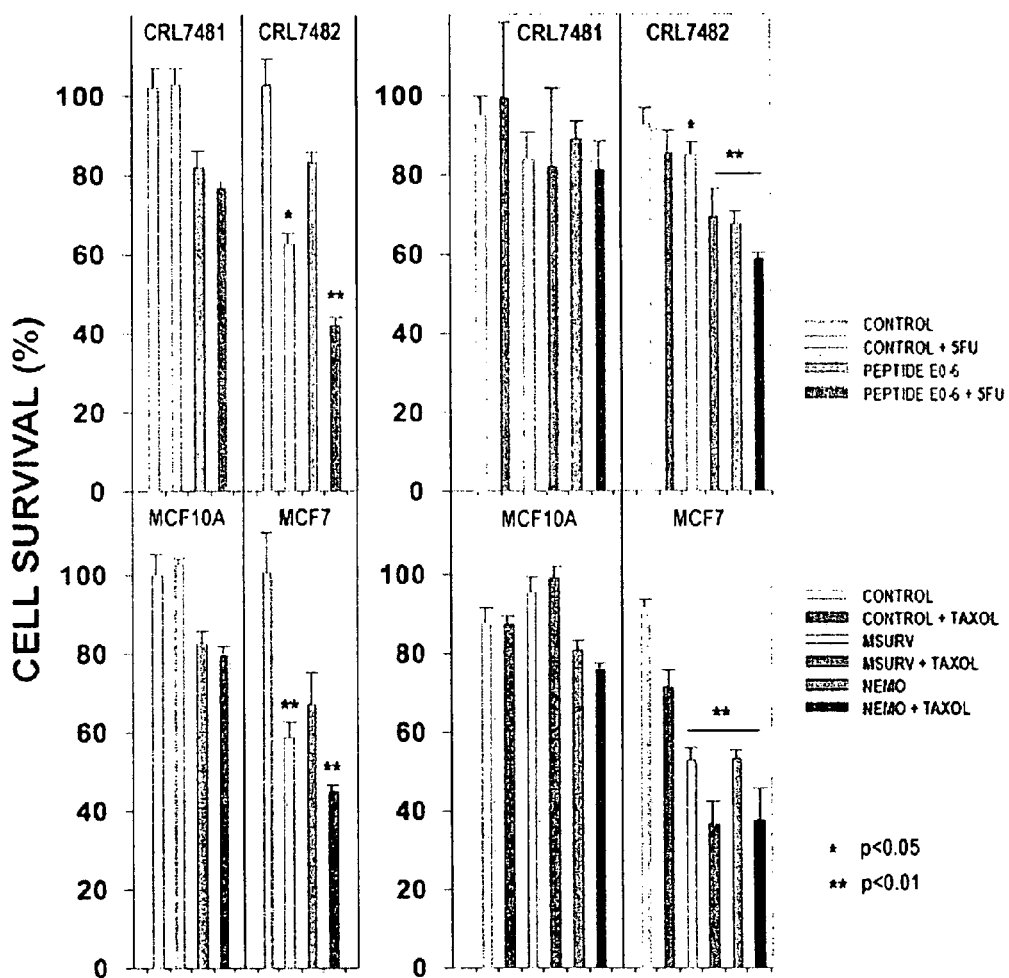
Figure 35. Selective toxicity of enhancers to cancer cells.

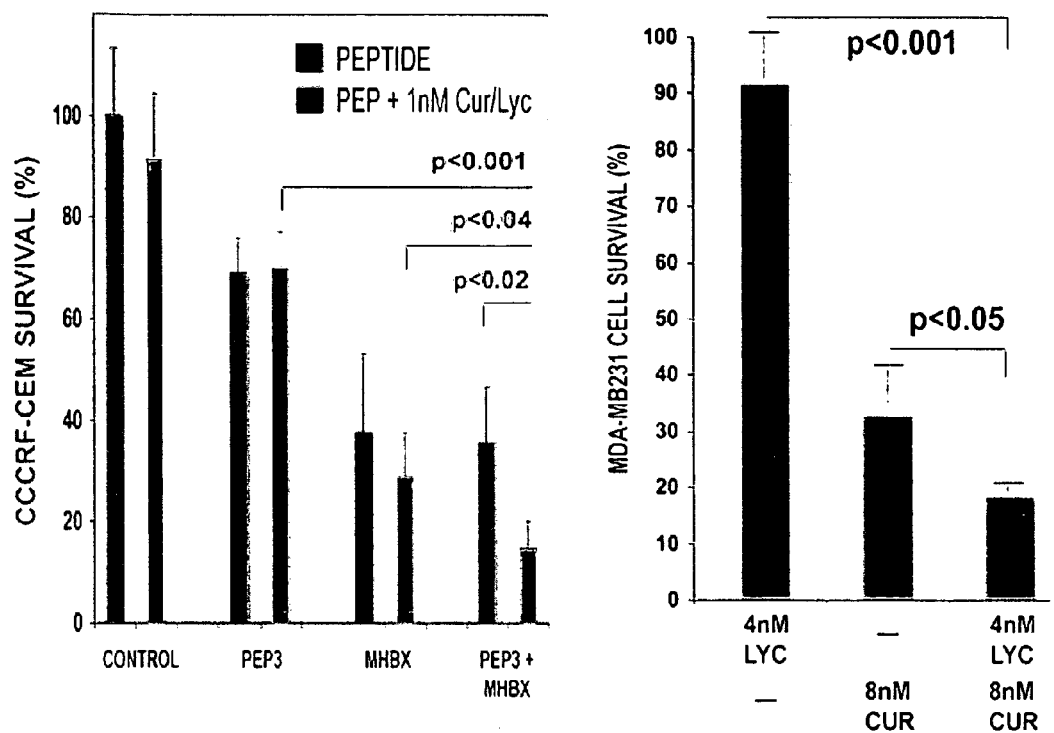
Figure 36. Additive effects of curcumin, lycopene and enhancers.

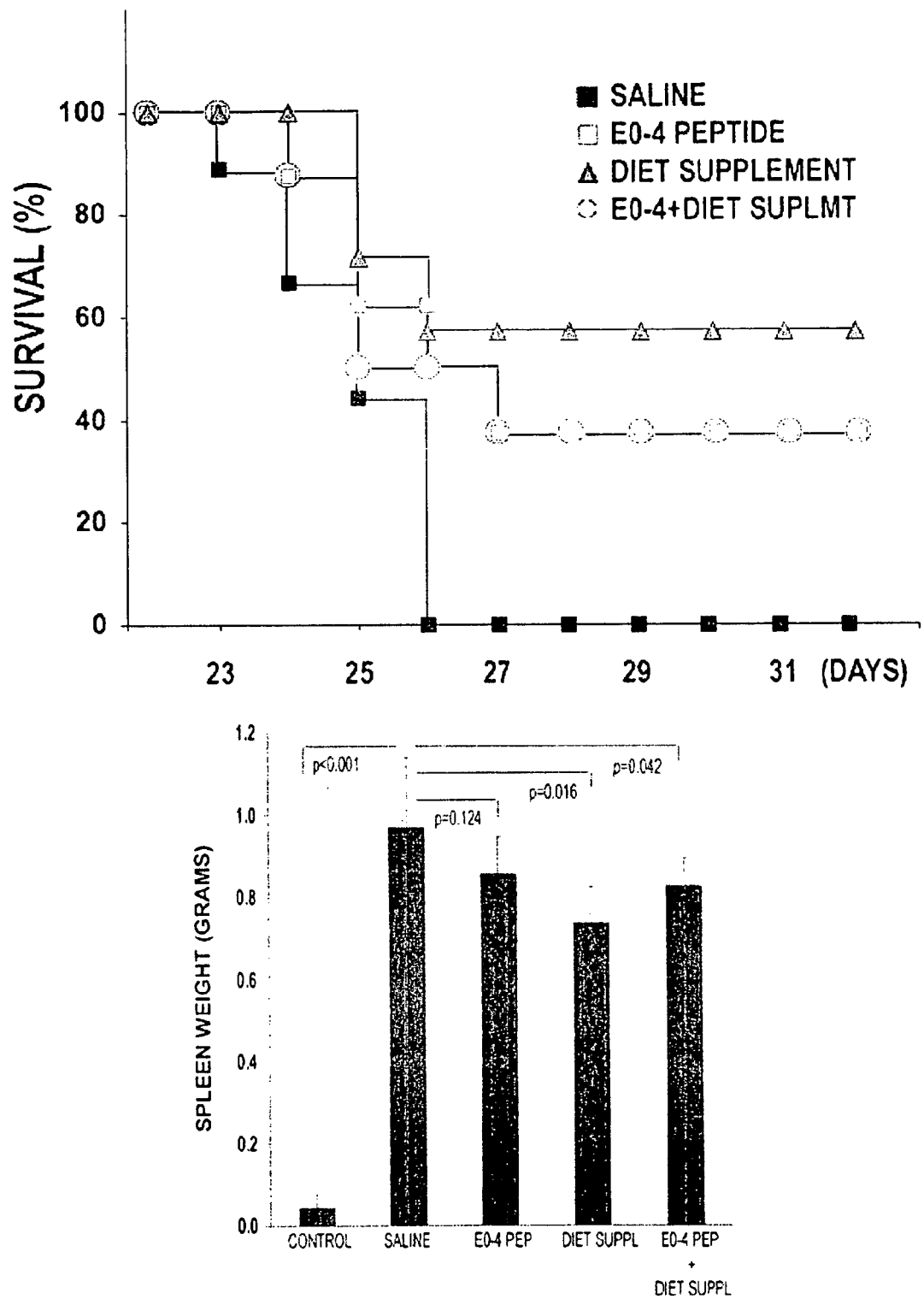
Figure 37. Effectiveness in CCRF-CEM Rag-2 mouse model of leukemia.

Figure 38. Effectiveness in MDA-MB-435 and MDA-MB-231 models of disseminated breast cancer.
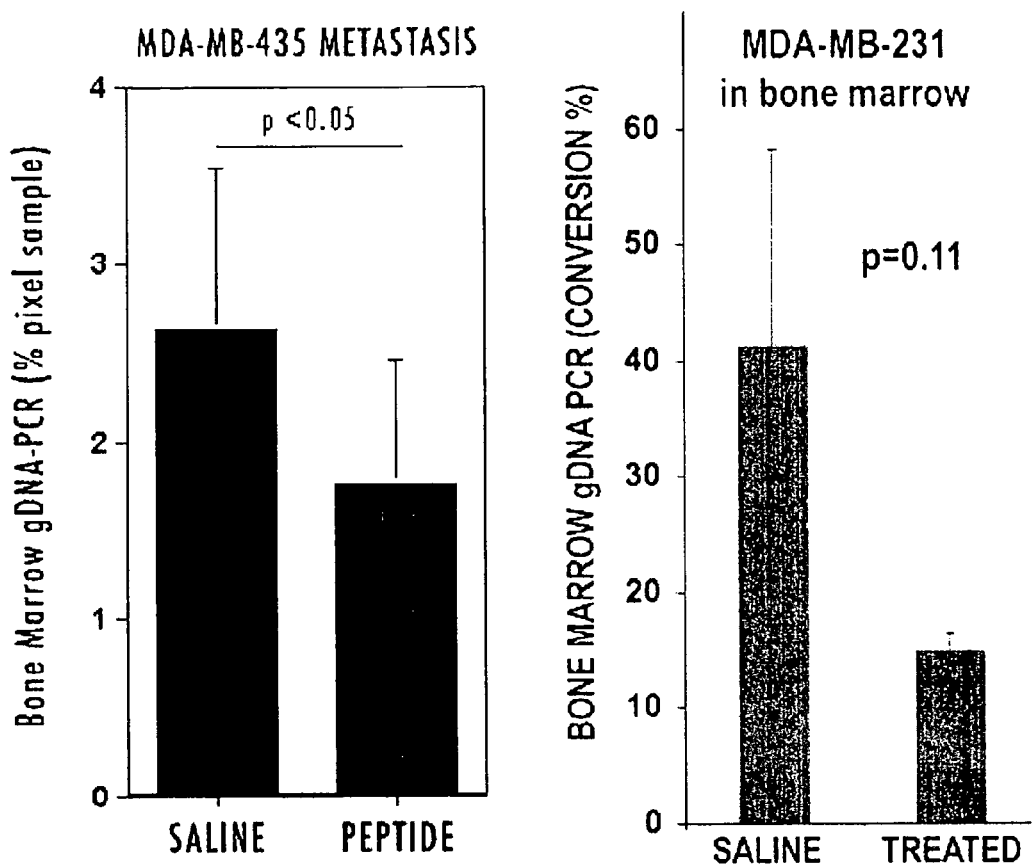

SEQUENCE LISTING

<160> NUMBER OF SEQ ID NOS: 187

<210> SEQ ID NO 1
<211> LENGTH: 15
<212> TYPE: PRT
<213> ORGANISM: Artificial Sequence
<220> FEATURE:
<223> OTHER INFORMATION: Synthetic construct

<400> SEQUENCE: 1

Ile Gly Leu His Asp Pro Ser His Gly Thr Leu Pro Asn Gly Ser
1               5                   10                  15

<210> SEQ ID NO 2
<211> LENGTH: 14
<212> TYPE: PRT
<213> ORGANISM: Artificial Sequence
<220> FEATURE:
<223> OTHER INFORMATION: Synthetic construct

<400> SEQUENCE: 2

Gln Cys Arg Pro Ser Lys Gly Arg Lys Arg Gly Phe Cys Trp
1               5                   10

<210> SEQ ID NO 3
<211> LENGTH: 20
<212> TYPE: PRT
<213> ORGANISM: Artificial Sequence
<220> FEATURE:
<223> OTHER INFORMATION: Synthetic construct -continued

```
<400> SEQUENCE: 3

Gln Cys Arg Pro Ser Lys Gly Arg Lys Arg Gly Phe Cys Trp Ala Val
1               5                   10                  15

Asp Lys Tyr Gly
            20

<210> SEQ ID NO 4
<211> LENGTH: 28
<212> TYPE: PRT
<213> ORGANISM: Artificial Sequence
<220> FEATURE:
<223> OTHER INFORMATION: Synthetic construct

<400> SEQUENCE: 4

Lys Lys Gly Phe Tyr Lys Lys Lys Gln Cys Arg Pro Ser Lys Gly Arg
1               5                   10                  15

Lys Arg Gly Phe Cys Trp Ala Val Asp Lys Tyr Gly
            20                  25

<210> SEQ ID NO 5
<211> LENGTH: 27
<212> TYPE: DNA
<213> ORGANISM: Artificial Sequence
<220> FEATURE:
<223> OTHER INFORMATION: Synthetic construct

<400> SEQUENCE: 5
tagcaataat ccccatcctc catatat                                        27

<210> SEQ ID NO 6
<211> LENGTH: 23
<212> TYPE: DNA
<213> ORGANISM: Artificial Sequence
<220> FEATURE:
<223> OTHER INFORMATION: Synthetic construct

<400> SEQUENCE: 6
acttgtccaa tgatggtaaa agg                                            23

<210> SEQ ID NO 7
<211> LENGTH: 12
<212> TYPE: PRT
<213> ORGANISM: Artificial Sequence
<220> FEATURE:
<223> OTHER INFORMATION: Synthetic construct

<400> SEQUENCE: 7

Cys Arg Pro Ser Lys Gly Arg Lys Arg Gly Phe Cys
1               5                   10

<210> SEQ ID NO 8
<211> LENGTH: 20
<212> TYPE: PRT
<213> ORGANISM: Artificial Sequence
<220> FEATURE:
<223> OTHER INFORMATION: Synthetic construct

<400> SEQUENCE: 8

Gly Phe Tyr Lys Lys Lys Gln Cys Arg Pro Ser Lys Gly Arg Lys Arg
1               5                   10                  15

Gly Phe Cys Trp
            20
```

<210> SEQ ID NO 9
<211> LENGTH: 22
<212> TYPE: PRT
<213> ORGANISM: Artificial Sequence
<220> FEATURE:
<223> OTHER INFORMATION: Synthetic construct

<400> SEQUENCE: 9

Lys Lys Gly Phe Tyr Lys Lys Lys Gln Cys Arg Pro Ser Lys Gly Arg
1               5                   10                  15

Lys Arg Gly Phe Cys Trp
            20

<210> SEQ ID NO 10
<211> LENGTH: 26
<212> TYPE: PRT
<213> ORGANISM: Artificial Sequence
<220> FEATURE:
<223> OTHER INFORMATION: Synthetic construct

<400> SEQUENCE: 10

Lys Lys Gly Phe Tyr Lys Lys Lys Gln Cys Arg Pro Ser Lys Gly Arg
1               5                   10                  15

Lys Arg Gly Phe Cys Trp Asn Gly Arg Lys
            20                  25

<210> SEQ ID NO 11
<211> LENGTH: 40
<212> TYPE: PRT
<213> ORGANISM: Artificial Sequence
<220> FEATURE:
<223> OTHER INFORMATION: Synthetic construct

<400> SEQUENCE: 11

Lys Gly Phe Tyr Lys Lys Lys Gln Cys Arg Pro Ser Lys Gly Arg Lys
1               5                   10                  15

Arg Gly Phe Cys Trp Ala Gln Thr Arg Arg Arg Glu Arg Arg Ala Glu
            20                  25                  30

Lys Gln Ala Gln Trp Lys Ala Ala
        35                  40

<210> SEQ ID NO 12
<211> LENGTH: 55
<212> TYPE: DNA
<213> ORGANISM: Artificial Sequence
<220> FEATURE:
<223> OTHER INFORMATION: Synthetic construct

<400> SEQUENCE: 12
agtttggcac aatcaataac tttttcagtt attgattgtg ccaaactcct gtctc      55

<210> SEQ ID NO 13
<211> LENGTH: 66
<212> TYPE: DNA
<213> ORGANISM: Artificial Sequence
<220> FEATURE:
<223> OTHER INFORMATION: Synthetic construct

<400> SEQUENCE: 13
gatcggcagt tggcacaat caataactga aaaagttatt gattgtgcca aactgttttt      60
tggaag                                                                66

```
<210> SEQ ID NO 14
<211> LENGTH: 66
<212> TYPE: DNA
<213> ORGANISM: Artificial Sequence
<220> FEATURE:
<223> OTHER INFORMATION: Synthetic construct

<400> SEQUENCE: 14
aattcttcca aaaacagtt tggcacaatc ataactttt tcagttattg attgtgccaa      60
actgcg                                                              66

<210> SEQ ID NO 15
<211> LENGTH: 27
<212> TYPE: PRT
<213> ORGANISM: Artificial Sequence
<220> FEATURE:
<223> OTHER INFORMATION: Synthetic construct

<400> SEQUENCE: 15

Glu Thr Phe Ser Asp Leu Trp Lys Leu Leu Lys Lys Trp Lys Met Arg
 1               5                  10                  15

Arg Asn Gln Phe Trp Val Lys Val Gln Arg Gly
            20                  25

<210> SEQ ID NO 16
<211> LENGTH: 32
<212> TYPE: PRT
<213> ORGANISM: Artificial Sequence
<220> FEATURE:
<223> OTHER INFORMATION: Synthetic construct

<400> SEQUENCE: 16

Glu Thr Phe Ser Asp Leu Trp Lys Leu Leu Lys Lys Gly Phe Tyr Lys
 1               5                  10                  15

Lys Lys Gln Cys Arg Pro Ser Lys Gly Arg Lys Arg Gly Phe Cys Trp
            20                  25                  30

<210> SEQ ID NO 17
<211> LENGTH: 32
<212> TYPE: PRT
<213> ORGANISM: Artificial Sequence
<220> FEATURE:
<223> OTHER INFORMATION: Synthetic construct

<400> SEQUENCE: 17

Glu Thr Phe Ser Asp Val Trp Lys Leu Leu Lys Lys Gly Phe Tyr Lys
 1               5                  10                  15

Lys Lys Gln Cys Arg Pro Ser Lys Gly Arg Lys Arg Gly Phe Cys Trp
            20                  25                  30

<210> SEQ ID NO 18
<211> LENGTH: 32
<212> TYPE: PRT
<213> ORGANISM: Artificial Sequence
<220> FEATURE:
<223> OTHER INFORMATION: Synthetic construct

<400> SEQUENCE: 18

Glu Thr Phe Ser Asp Ile Trp Lys Leu Leu Lys Lys Gly Phe Tyr Lys
 1               5                  10                  15

Lys Lys Gln Cys Arg Pro Ser Lys Gly Arg Lys Arg Gly Phe Cys Trp
            20                  25                  30
```

<210> SEQ ID NO 19
<211> LENGTH: 34
<212> TYPE: PRT
<213> ORGANISM: Artificial Sequence
<220> FEATURE:
<223> OTHER INFORMATION: Synthetic construct

<400> SEQUENCE: 19

Lys Lys Gly Phe Tyr Lys Lys Lys Gln Cys Arg Pro Ser Lys Gly Arg
 1               5                  10                  15

Lys Arg Gly Phe Cys Trp Ala Pro Val Gln Arg Lys Arg Gln Lys Leu
            20                  25                  30
        Met Pro

<210> SEQ ID NO 20
<211> LENGTH: 32
<212> TYPE: PRT
<213> ORGANISM: Artificial Sequence
<220> FEATURE:
<223> OTHER INFORMATION: Synthetic construct

<400> SEQUENCE: 20

Lys Lys Gly Phe Tyr Lys Lys Lys Gln Cys Arg Pro Ser Lys Gly Arg
 1               5                  10                  15

Lys Arg Gly Phe Cys Trp Ala Ala Leu Asp Trp Ser Trp Leu Gln Thr
            20                  25                  30

<210> SEQ ID NO 21
<211> LENGTH: 34
<212> TYPE: PRT
<213> ORGANISM: Artificial Sequence
<220> FEATURE:
<223> OTHER INFORMATION: Synthetic construct

<400> SEQUENCE: 21

Lys Lys Gly Phe Tyr Lys Lys Lys Gln Cys Arg Pro Ser Lys Gly Arg
 1               5                  10                  15

Lys Arg Gly Phe Cys Trp Ala Val Ala Glu Tyr Ala Arg Val Gln Lys
            20                  25                  30

Arg Lys

<210> SEQ ID NO 22
<211> LENGTH: 28
<212> TYPE: PRT
<213> ORGANISM: Artificial Sequence
<220> FEATURE:
<223> OTHER INFORMATION: Synthetic construct

<400> SEQUENCE: 22

Leu Lys Ile Leu Leu Leu Arg Lys Gln Cys Arg Pro Ser Lys Gly Arg
 1               5                  10                  15

Lys Arg Gly Phe Cys Trp Ala Val Asp Lys Tyr Gly
            20                  25

<210> SEQ ID NO 23
<211> LENGTH: 35
<212> TYPE: PRT
<213> ORGANISM: Artificial Sequence
<220> FEATURE:
<223> OTHER INFORMATION: Synthetic construct -continued

```
<400> SEQUENCE: 23

Lys Lys Gly Phe Tyr Lys Lys Lys Gln Cys Arg Pro Ser Lys Gly Arg
1               5                   10                  15

Lys Arg Gly Phe Cys Trp Ala Thr Gly Val Tyr Val Lys Met Pro Pro
            20                  25                  30

Thr Glu Pro
        35

<210> SEQ ID NO 24
<211> LENGTH: 35
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: 27
<223> OTHER INFORMATION: Xaa = phosphorylated tyrosine

<400> SEQUENCE: 24

Lys Lys Gly Phe Tyr Lys Lys Lys Gln Cys Arg Pro Ser Lys Gly Arg
1               5                   10                  15

Lys Arg Gly Phe Cys Trp Ala His Ser Asp Xaa Met Asn Met Thr Pro
            20                  25                  30

Arg Arg Pro
        35

<210> SEQ ID NO 25
<211> LENGTH: 35
<212> TYPE: PRT
<213> ORGANISM: Artificial Sequence
<220> FEATURE:
<223> OTHER INFORMATION: Synthetic construct

<400> SEQUENCE: 25

Lys Lys Gly Phe Tyr Lys Lys Lys Gln Cys Arg Pro Ser Lys Gly Arg
1               5                   10                  15

Lys Arg Gly Phe Cys Trp Arg Phe Ala Arg Lys Gly Ala Leu Arg Gln
            20                  25                  30

Lys Asn Val
        35

<210> SEQ ID NO 26
<211> LENGTH: 35
<212> TYPE: PRT
<213> ORGANISM: Artificial Sequence
<220> FEATURE:
<223> OTHER INFORMATION: Synthetic construct

<400> SEQUENCE: 26

Lys Lys Gly Phe Tyr Lys Lys Lys Gln Cys Arg Pro Ser Lys Gly Arg
1               5                   10                  15

Lys Arg Gly Phe Cys Trp Gly Pro His Pro Val Ile Val Ile Thr Gly
            20                  25                  30

Pro His Glu
        35

<210> SEQ ID NO 27
<211> LENGTH: 37
<212> TYPE: PRT
<213> ORGANISM: Artificial Sequence
<220> FEATURE:
<223> OTHER INFORMATION: Synthetic construct
```

```
<400> SEQUENCE: 27

Lys Lys Gly Phe Tyr Lys Lys Gln Cys Arg Pro Ser Lys Gly Arg
  1               5                  10                  15

Lys Arg Gly Phe Cys Trp Ala Glu Tyr Ala Arg Val Gln Arg Lys Arg
             20                  25                  30

Gln Lys Leu Met Pro
         35

<210> SEQ ID NO 28
<211> LENGTH: 37
<212> TYPE: PRT
<213> ORGANISM: Artificial Sequence
<220> FEATURE:
<223> OTHER INFORMATION: Synthetic construct

<400> SEQUENCE: 28

Lys Lys Gly Phe Tyr Lys Lys Gln Cys Arg Pro Ser Lys Gly Arg
  1               5                  10                  15

Lys Arg Gly Phe Cys Trp Ala Leu Asp Trp Ser Trp Leu Gln Arg Lys
             20                  25                  30

Arg Gln Lys Leu Met
         35

<210> SEQ ID NO 29
<211> LENGTH: 42
<212> TYPE: PRT
<213> ORGANISM: Artificial Sequence
<220> FEATURE:
<223> OTHER INFORMATION: Synthetic construct

<400> SEQUENCE: 29

Lys Lys Gly Phe Tyr Lys Lys Gln Cys Arg Pro Ser Lys Gly Arg
  1               5                  10                  15

Lys Arg Gly Phe Cys Trp Ala Arg Ile Asp Asp Met Ser Ser Arg Ile
             20                  25                  30

Asp Asp Leu Glu Lys Asn Ile Ala Asp Leu
         35                  40

<210> SEQ ID NO 30
<211> LENGTH: 42
<212> TYPE: PRT
<213> ORGANISM: Artificial Sequence
<220> FEATURE:
<223> OTHER INFORMATION: Synthetic construct

<400> SEQUENCE: 30

Lys Lys Gly Phe Tyr Lys Lys Gln Cys Arg Pro Ser Lys Gly Arg
  1               5                  10                  15

Lys Arg Gly Phe Cys Trp Ala Val Gln Thr Leu Leu Gln Gln Met Gln
             20                  25                  30

Asp Lys Phe Gln Thr Met Ser Asp Gln Ile
         35                  40

<210> SEQ ID NO 31
<211> LENGTH: 37
<212> TYPE: PRT
<213> ORGANISM: Artificial Sequence
<220> FEATURE:
<223> OTHER INFORMATION: Synthetic construct
```

```
<400> SEQUENCE: 31

Ala Lys Pro Phe Tyr Lys Lys Gln Cys Arg Pro Ser Lys Gly Arg
 1               5                  10                  15

Lys Arg Gly Phe Cys Trp Gly Ser Ser Gly Leu Gly Glu Phe Leu Lys
             20                  25                  30

Leu Asp Arg Glu Arg
         35

<210> SEQ ID NO 32
<211> LENGTH: 33
<212> TYPE: PRT
<213> ORGANISM: Artificial Sequence
<220> FEATURE:
<223> OTHER INFORMATION: Synthetic construct

<400> SEQUENCE: 32

Lys Lys Gly Phe Tyr Lys Lys Lys Gln Cys Arg Pro Ser Lys Gly Arg
 1               5                  10                  15

Lys Arg Gly Phe Cys Trp Pro Tyr Thr Leu Leu Arg Arg Tyr Gly Arg
             20                  25                  30

Asp

<210> SEQ ID NO 33
<211> LENGTH: 28
<212> TYPE: PRT
<213> ORGANISM: Artificial Sequence
<220> FEATURE:
<223> OTHER INFORMATION: Synthetic construct

<400> SEQUENCE: 33

Glu Tyr Arg Glu Ile Asp Lys Arg Gly Phe Tyr Lys Lys Gln Cys
 1               5                  10                  15

Arg Pro Ser Lys Gly Arg Lys Arg Gly Phe Cys Trp
             20                  25

<210> SEQ ID NO 34
<211> LENGTH: 31
<212> TYPE: PRT
<213> ORGANISM: Artificial Sequence
<220> FEATURE:
<223> OTHER INFORMATION: Synthetic construct

<400> SEQUENCE: 34

Lys Lys Gly Phe Tyr Lys Lys Lys Gln Cys Arg Pro Ser Lys Gly Arg
 1               5                  10                  15

Lys Arg Gly Phe Cys Trp Lys Pro Leu Tyr Trp Asp Leu Tyr Glu
             20                  25                  30

<210> SEQ ID NO 35
<211> LENGTH: 38
<212> TYPE: PRT
<213> ORGANISM: Artificial Sequence
<220> FEATURE:
<223> OTHER INFORMATION: Synthetic construct

<400> SEQUENCE: 35

His Asp Arg Lys Glu Phe Ala Lys Phe Glu Glu Glu Arg Ala Arg Ala
 1               5                  10                  15

Lys Lys Gly Phe Tyr Lys Lys Lys Gln Cys Arg Pro Ser Lys Gly Arg
             20                  25                  30

Lys Arg Gly Phe Cys Trp
         35
```

```
<210> SEQ ID NO 36
<211> LENGTH: 28
<212> TYPE: PRT
<213> ORGANISM: Artificial Sequence
<220> FEATURE:
<223> OTHER INFORMATION: Synthetic construct

<400> SEQUENCE: 36

Arg Glu Asn Leu Arg Ile Ala Leu Arg Tyr Tyr Lys Lys Gln Cys
 1               5                  10                  15

Arg Pro Ser Lys Gly Arg Lys Arg Gly Phe Cys Trp
            20                  25

<210> SEQ ID NO 37
<211> LENGTH: 28
<212> TYPE: PRT
<213> ORGANISM: Artificial Sequence
<220> FEATURE:
<223> OTHER INFORMATION: Synthetic construct

<400> SEQUENCE: 37

Arg Glu Ser Leu Arg Asn Leu Arg Gly Tyr Tyr Lys Lys Gln Cys
 1               5                  10                  15

Arg Pro Ser Lys Gly Arg Lys Arg Gly Phe Cys Trp
            20                  25

<210> SEQ ID NO 38
<211> LENGTH: 31
<212> TYPE: PRT
<213> ORGANISM: Artificial Sequence
<220> FEATURE:
<223> OTHER INFORMATION: Synthetic construct

<400> SEQUENCE: 38

Lys Lys Gly Phe Tyr Lys Lys Lys Gln Cys Arg Pro Ser Lys Gly Arg
 1               5                  10                  15

Lys Arg Gly Phe Cys Trp Lys Ala Leu Tyr Trp Asp Leu Tyr Glu
            20                  25                  30

<210> SEQ ID NO 39
<211> LENGTH: 30
<212> TYPE: PRT
<213> ORGANISM: Artificial Sequence
<220> FEATURE:
<223> OTHER INFORMATION: Synthetic construct

<400> SEQUENCE: 39

Lys Gly Phe Tyr Lys Lys Lys Gln Cys Arg Pro Ser Lys Gly Arg Lys
 1               5                  10                  15

Arg Gly Phe Cys Trp Lys Ala Leu Tyr Trp Asp Leu Tyr Glu
            20                  25                  30

<210> SEQ ID NO 40
<211> LENGTH: 31
<212> TYPE: PRT
<213> ORGANISM: Artificial Sequence
<220> FEATURE:
<223> OTHER INFORMATION: Synthetic construct

<400> SEQUENCE: 40

Lys Gly Phe Tyr Lys Lys Lys Gln Cys Arg Pro Ser Lys Gly Arg Lys
 1               5                  10                  15

Arg Gly Phe Cys Trp Lys Ala Leu Tyr Trp Asp Leu Tyr Glu Met
            20                  25                  30
```

```
<210> SEQ ID NO 41
<211> LENGTH: 31
<212> TYPE: PRT
<213> ORGANISM: Artificial Sequence
<220> FEATURE:
<223> OTHER INFORMATION: Synthetic construct

<400> SEQUENCE: 41

Lys Gly Phe Tyr Lys Lys Lys Gln Cys Arg Pro Ser Lys Gly Arg Lys
 1               5                   10                  15

Arg Gly Phe Cys Trp Ala Ala Leu Tyr Trp Asp Leu Tyr Glu Met
            20                  25                  30

<210> SEQ ID NO 42
<211> LENGTH: 30
<212> TYPE: PRT
<213> ORGANISM: Artificial Sequence
<220> FEATURE:
<223> OTHER INFORMATION: Synthetic construct

<400> SEQUENCE: 42

Lys Gly Phe Tyr Lys Lys Lys Gln Cys Arg Pro Ser Lys Gly Arg Lys
 1               5                   10                  15

Arg Gly Phe Cys Trp Ala Leu Tyr Trp Asp Leu Tyr Glu Met
            20                  25                  30

<210> SEQ ID NO 43
<211> LENGTH: 30
<212> TYPE: PRT
<213> ORGANISM: Artificial Sequence
<220> FEATURE:
<223> OTHER INFORMATION: Synthetic construct

<400> SEQUENCE: 43

Lys Gly Phe Tyr Lys Lys Lys Gln Cys Arg Pro Ser Lys Gly Arg Lys
 1               5                   10                  15

Arg Gly Phe Cys Trp Ala Leu Tyr Trp Ala Leu Tyr Glu Met
            20                  25                  30

<210> SEQ ID NO 44
<211> LENGTH: 33
<212> TYPE: PRT
<213> ORGANISM: Artificial Sequence
<220> FEATURE:
<223> OTHER INFORMATION: Synthetic construct

<400> SEQUENCE: 44

Lys Gly Phe Tyr Lys Lys Lys Gln Cys Arg Pro Ser Lys Gly Arg Lys
 1               5                   10                  15

Arg Gly Phe Cys Trp Ala Pro Val Gln Arg Lys Arg Gln Lys Leu Met
            20                  25                  30

Pro

<210> SEQ ID NO 45
<211> LENGTH: 33
<212> TYPE: PRT
<213> ORGANISM: Artificial Sequence
<220> FEATURE:
<223> OTHER INFORMATION: Synthetic construct
```

```
<400> SEQUENCE: 45

Lys Lys Gly Phe Tyr Lys Lys Gln Cys Arg Pro Ser Lys Gly Arg
1               5                   10                  15

Lys Arg Gly Phe Cys Trp Ala Val Gln Arg Lys Arg Gln Lys Leu Met
            20                  25                  30

Pro

<210> SEQ ID NO 46
<211> LENGTH: 33
<212> TYPE: PRT
<213> ORGANISM: Artificial Sequence
<220> FEATURE:
<223> OTHER INFORMATION: Synthetic construct

<400> SEQUENCE: 46

Lys Gly Phe Tyr Lys Lys Gln Cys Arg Pro Ser Lys Gly Arg Lys
1               5                   10                  15

Arg Gly Phe Cys Trp Ala Val Ala Glu Tyr Ala Arg Val Gln Lys Arg
            20                  25                  30

Lys

<210> SEQ ID NO 47
<211> LENGTH: 33
<212> TYPE: PRT
<213> ORGANISM: Artificial Sequence
<220> FEATURE:
<223> OTHER INFORMATION: Synthetic construct

<400> SEQUENCE: 47

Lys Gly Phe Tyr Lys Lys Gln Cys Arg Pro Ser Lys Gly Arg Lys
1               5                   10                  15

Arg Gly Phe Cys Trp Ala Val Ala Leu Tyr Ala Arg Val Gln Lys Arg
            20                  25                  30

Lys

<210> SEQ ID NO 48
<211> LENGTH: 31
<212> TYPE: PRT
<213> ORGANISM: Artificial Sequence
<220> FEATURE:
<223> OTHER INFORMATION: Synthetic construct

<400> SEQUENCE: 48

Val Ala Glu Tyr Ala Arg Val Gln Lys Arg Lys Gly Phe Tyr Lys Lys
1               5                   10                  15

Lys Gln Cys Arg Pro Ser Lys Gly Arg Lys Arg Gly Phe Cys Trp
            20                  25                  30

<210> SEQ ID NO 49
<211> LENGTH: 31
<212> TYPE: PRT
<213> ORGANISM: Artificial Sequence
<220> FEATURE:
<223> OTHER INFORMATION: Synthetic construct

<400> SEQUENCE: 49

Val Ala Leu Tyr Ala Arg Val Gln Lys Arg Lys Gly Phe Tyr Lys Lys
1               5                   10                  15

Lys Gln Cys Arg Pro Ser Lys Gly Arg Lys Arg Gly Phe Cys Trp
            20                  25                  30
```

```
<210> SEQ ID NO 50
<211> LENGTH: 36
<212> TYPE: PRT
<213> ORGANISM: Artificial Sequence
<220> FEATURE:
<223> OTHER INFORMATION: Synthetic construct

<400> SEQUENCE: 50

Ala Lys Pro Phe Tyr Lys Lys Lys Gln Cys Arg Pro Ser Lys Gly Arg
 1               5                  10                  15

Lys Arg Gly Phe Cys Trp Ala Ser Gly Leu Gly Glu Phe Leu Lys Leu
            20                  25                  30

Asp Arg Glu Arg
        35

<210> SEQ ID NO 51
<211> LENGTH: 35
<212> TYPE: PRT
<213> ORGANISM: Artificial Sequence
<220> FEATURE:
<223> OTHER INFORMATION: Synthetic construct

<400> SEQUENCE: 51

Ala Lys Pro Phe Tyr Lys Lys Lys Gln Cys Arg Pro Ser Lys Gly Arg
 1               5                  10                  15

Lys Arg Gly Phe Cys Trp Ala Gly Leu Gly Glu Phe Leu Lys Leu Asp
            20                  25                  30

Arg Glu Arg
        35

<210> SEQ ID NO 52
<211> LENGTH: 37
<212> TYPE: PRT
<213> ORGANISM: Artificial Sequence
<220> FEATURE:
<223> OTHER INFORMATION: Synthetic construct

<400> SEQUENCE: 52

Ala Lys Pro Phe Tyr Lys Lys Lys Gln Cys Arg Pro Ser Lys Gly Arg
 1               5                  10                  15

Lys Arg Gly Phe Cys Trp Gly Ser Ser Gly Leu Gly Glu Phe Leu Lys
            20                  25                  30

Leu Asp Arg Glu Ala
        35

<210> SEQ ID NO 53
<211> LENGTH: 37
<212> TYPE: PRT
<213> ORGANISM: Artificial Sequence
<220> FEATURE:
<223> OTHER INFORMATION: Synthetic construct

<400> SEQUENCE: 53

Ala Lys Pro Phe Tyr Lys Lys Lys Gln Cys Arg Pro Ser Lys Gly Arg
 1               5                  10                  15

Lys Arg Gly Phe Cys Trp Gly Ser Ser Gly Leu Gly Glu Phe Leu Lys
            20                  25                  30

Leu Asp Arg Ala Arg
        35
```

<210> SEQ ID NO 54
<211> LENGTH: 37
<212> TYPE: PRT
<213> ORGANISM: Artificial Sequence
<220> FEATURE:
<223> OTHER INFORMATION: Synthetic construct

<400> SEQUENCE: 54

Ala Lys Pro Phe Tyr Lys Lys Gln Cys Arg Pro Ser Lys Gly Arg
1               5                   10                  15

Lys Arg Gly Phe Cys Trp Gly Ser Ser Gly Leu Gly Glu Phe Leu Lys
            20                  25                  30

Leu Asp Ala Glu Arg
        35

<210> SEQ ID NO 55
<211> LENGTH: 37
<212> TYPE: PRT
<213> ORGANISM: Artificial Sequence
<220> FEATURE:
<223> OTHER INFORMATION: Synthetic construct

<400> SEQUENCE: 55

Ala Lys Pro Phe Tyr Lys Lys Gln Cys Arg Pro Ser Lys Gly Arg
1               5                   10                  15

Lys Arg Gly Phe Cys Trp Gly Ser Ser Gly Leu Gly Glu Phe Leu Lys
            20                  25                  30

Leu Ala Arg Glu Arg
        35

<210> SEQ ID NO 56
<211> LENGTH: 37
<212> TYPE: PRT
<213> ORGANISM: Artificial Sequence
<220> FEATURE:
<223> OTHER INFORMATION: Synthetic construct

<400> SEQUENCE: 56

Ala Lys Pro Phe Tyr Lys Lys Gln Cys Arg Pro Ser Lys Gly Arg
1               5                   10                  15

Lys Arg Gly Phe Cys Trp Gly Ser Ser Gly Leu Gly Glu Phe Leu Lys
            20                  25                  30

Ala Asp Arg Glu Arg
        35

<210> SEQ ID NO 57
<211> LENGTH: 37
<212> TYPE: PRT
<213> ORGANISM: Artificial Sequence
<220> FEATURE:
<223> OTHER INFORMATION: Synthetic construct

<400> SEQUENCE: 57

Ala Lys Pro Phe Tyr Lys Lys Gln Cys Arg Pro Ser Lys Gly Arg
1               5                   10                  15

Lys Arg Gly Phe Cys Trp Gly Ser Ser Gly Leu Gly Glu Phe Leu Ala
            20                  25                  30

Leu Asp Arg Glu Arg
        35

```
<210> SEQ ID NO 58
<211> LENGTH: 37
<212> TYPE: PRT
<213> ORGANISM: Artificial Sequence
<220> FEATURE:
<223> OTHER INFORMATION: Synthetic construct

<400> SEQUENCE: 58

Ala Lys Pro Phe Tyr Lys Lys Gln Cys Arg Pro Ser Lys Gly Arg
 1               5                  10                  15

Lys Arg Gly Phe Cys Trp Gly Ser Ser Gly Leu Gly Glu Phe Ala Lys
            20                  25                  30

Leu Asp Arg Glu Arg
        35

<210> SEQ ID NO 59
<211> LENGTH: 37
<212> TYPE: PRT
<213> ORGANISM: Artificial Sequence
<220> FEATURE:
<223> OTHER INFORMATION: Synthetic construct

<400> SEQUENCE: 59

Ala Lys Pro Phe Tyr Lys Lys Gln Cys Arg Pro Ser Lys Gly Arg
 1               5                  10                  15

Lys Arg Gly Phe Cys Trp Gly Ser Ser Gly Leu Gly Glu Ala Leu Lys
            20                  25                  30

Leu Asp Arg Glu Arg
        35

<210> SEQ ID NO 60
<211> LENGTH: 37
<212> TYPE: PRT
<213> ORGANISM: Artificial Sequence
<220> FEATURE:
<223> OTHER INFORMATION: Synthetic construct

<400> SEQUENCE: 60

Ala Lys Pro Phe Tyr Lys Lys Gln Cys Arg Pro Ser Lys Gly Arg
 1               5                  10                  15

Lys Arg Gly Phe Cys Trp Gly Ser Ser Gly Leu Gly Ala Phe Leu Lys
            20                  25                  30

Leu Asp Arg Glu Arg
        35

<210> SEQ ID NO 61
<211> LENGTH: 37
<212> TYPE: PRT
<213> ORGANISM: Artificial Sequence
<220> FEATURE:
<223> OTHER INFORMATION: Synthetic construct

<400> SEQUENCE: 61

Ala Lys Pro Phe Tyr Lys Lys Gln Cys Arg Pro Ser Lys Gly Arg
 1               5                  10                  15

Lys Arg Gly Phe Cys Trp Gly Ser Ser Gly Leu Ala Glu Phe Leu Lys
            20                  25                  30

Leu Asp Arg Glu Arg
        35
```

<210> SEQ ID NO 62
<211> LENGTH: 37
<212> TYPE: PRT
<213> ORGANISM: Artificial Sequence
<220> FEATURE:
<223> OTHER INFORMATION: Synthetic construct

<400> SEQUENCE: 62

Ala Lys Pro Phe Tyr Lys Lys Gln Cys Arg Pro Ser Lys Gly Arg
1               5                   10                  15
Lys Arg Gly Phe Cys Trp Gly Ser Ser Gly Ala Gly Glu Phe Leu Lys
            20                  25                  30
Leu Asp Arg Glu Arg
        35

<210> SEQ ID NO 63
<211> LENGTH: 38
<212> TYPE: PRT
<213> ORGANISM: Artificial Sequence
<220> FEATURE:
<223> OTHER INFORMATION: Synthetic construct

<400> SEQUENCE: 63

Lys Lys Gly Phe Tyr Lys Lys Gln Cys Arg Pro Ser Lys Gly Arg
1               5                   10                  15
Lys Arg Gly Phe Cys Trp Ala Ile Gly Leu His Asp Pro Ser His Gly
            20                  25                  30
Thr Leu Pro Asn Gly Ser
        35

<210> SEQ ID NO 64
<211> LENGTH: 38
<212> TYPE: PRT
<213> ORGANISM: Artificial Sequence
<220> FEATURE:
<223> OTHER INFORMATION: Synthetic construct

<400> SEQUENCE: 64

Lys Lys Gly Phe Tyr Lys Lys Gln Cys Arg Pro Ser Lys Gly Arg
1               5                   10                  15
Lys Arg Gly Phe Cys Trp Ala Ile Gly Leu His Ala Pro Ser His Gly
            20                  25                  30
Thr Leu Pro Asn Gly Ser
        35

<210> SEQ ID NO 65
<211> LENGTH: 37
<212> TYPE: PRT
<213> ORGANISM: Artificial Sequence
<220> FEATURE:
<223> OTHER INFORMATION: Synthetic construct

<400> SEQUENCE: 65

Lys Lys Gly Phe Tyr Lys Lys Gln Cys Arg Pro Ser Lys Gly Arg
1               5                   10                  15
Lys Arg Gly Phe Cys Trp Ala Ile Gly Leu His Asp Pro Ser His Gly
            20                  25                  30
Thr Leu Pro Asn Gly
        35

<210> SEQ ID NO 66
<211> LENGTH: 37
<212> TYPE: PRT
<213> ORGANISM: Artificial Sequence
<220> FEATURE:
<223> OTHER INFORMATION: Synthetic construct

<400> SEQUENCE: 66

Ile Gly Leu His Asp Pro Ser His Gly Thr Leu Pro Asn Gly Ser Lys
1               5                   10                  15

Lys Gly Phe Tyr Lys Lys Lys Gln Cys Arg Pro Ser Lys Gly Arg Lys
            20                  25                  30

Arg Gly Phe Cys Trp
        35

<210> SEQ ID NO 67
<211> LENGTH: 37
<212> TYPE: PRT
<213> ORGANISM: Artificial Sequence
<220> FEATURE:
<223> OTHER INFORMATION: Synthetic construct

<400> SEQUENCE: 67

Ile Gly Leu His Ala Pro Ser His Gly Thr Leu Pro Asn Gly Ser Lys
1               5                   10                  15

Lys Gly Phe Tyr Lys Lys Lys Gln Cys Arg Pro Ser Lys Gly Arg Lys
            20                  25                  30

Arg Gly Phe Cys Trp
        35

<210> SEQ ID NO 68
<211> LENGTH: 33
<212> TYPE: PRT
<213> ORGANISM: Artificial Sequence
<220> FEATURE:
<223> OTHER INFORMATION: Synthetic construct

<400> SEQUENCE: 68

Ile Gly Leu His Asp Pro Ser His Gly Thr Leu Pro Asn Gly Phe Tyr
1               5                   10                  15

Lys Lys Lys Gln Cys Arg Pro Ser Lys Gly Arg Lys Arg Gly Phe Cys
            20                  25                  30

Trp

<210> SEQ ID NO 69
<211> LENGTH: 21
<212> TYPE: PRT
<213> ORGANISM: Artificial Sequence
<220> FEATURE:
<223> OTHER INFORMATION: Synthetic construct

<400> SEQUENCE: 69

Lys Gly Phe Tyr Lys Lys Lys Gln Cys Arg Pro Ser Lys Gly Arg Lys
1               5                   10                  15

Arg Gly Phe Cys Trp
            20

<210> SEQ ID NO 70
<211> LENGTH: 41
<212> TYPE: PRT
<213> ORGANISM: Artificial Sequence
<220> FEATURE:
<223> OTHER INFORMATION: Synthetic construct

```
<400> SEQUENCE: 70

Lys Gly Phe Tyr Lys Lys Gln Cys Arg Pro Ser Lys Gly Arg Lys
1               5                   10                  15

Arg Gly Phe Cys Trp Ala Arg Ile Asp Asp Met Ser Ser Arg Ile Asp
            20                  25                  30

Asp Leu Glu Lys Asn Ile Ala Asp Leu
        35                  40

<210> SEQ ID NO 71
<211> LENGTH: 41
<212> TYPE: PRT
<213> ORGANISM: Artificial Sequence
<220> FEATURE:
<223> OTHER INFORMATION: Synthetic construct

<400> SEQUENCE: 71

Lys Gly Phe Tyr Lys Lys Gln Cys Arg Pro Ser Lys Gly Arg Lys
1               5                   10                  15

Arg Gly Phe Cys Trp Ala Ala Ile Asp Asp Met Ser Ser Arg Ile Asp
            20                  25                  30

Asp Leu Glu Lys Asn Ile Ala Asp Leu
        35                  40

<210> SEQ ID NO 72
<211> LENGTH: 41
<212> TYPE: PRT
<213> ORGANISM: Artificial Sequence
<220> FEATURE:
<223> OTHER INFORMATION: Synthetic construct

<400> SEQUENCE: 72

Lys Gly Phe Tyr Lys Lys Gln Cys Arg Pro Ser Lys Gly Arg Lys
1               5                   10                  15

Arg Gly Phe Cys Trp Ala Arg Ala Asp Asp Met Ser Ser Arg Ile Asp
            20                  25                  30

Asp Leu Glu Lys Asn Ile Ala Asp Leu
        35                  40

<210> SEQ ID NO 73
<211> LENGTH: 41
<212> TYPE: PRT
<213> ORGANISM: Artificial Sequence
<220> FEATURE:
<223> OTHER INFORMATION: Synthetic construct

<400> SEQUENCE: 73

Lys Gly Phe Tyr Lys Lys Gln Cys Arg Pro Ser Lys Gly Arg Lys
1               5                   10                  15

Arg Gly Phe Cys Trp Ala Arg Ile Ala Asp Met Ser Ser Arg Ile Asp
            20                  25                  30

Asp Leu Glu Lys Asn Ile Ala Asp Leu
        35                  40

<210> SEQ ID NO 74
<211> LENGTH: 41
<212> TYPE: PRT
<213> ORGANISM: Artificial Sequence
<220> FEATURE:
<223> OTHER INFORMATION: Synthetic construct
```

```
<400> SEQUENCE: 74

Lys Gly Phe Tyr Lys Lys Gln Cys Arg Pro Ser Lys Gly Arg Lys
 1               5                  10                  15

Arg Gly Phe Cys Trp Ala Arg Ile Asp Ala Met Ser Ser Arg Ile Asp
            20                  25                  30

Asp Leu Glu Lys Asn Ile Ala Asp Leu
        35                  40

<210> SEQ ID NO 75
<211> LENGTH: 41
<212> TYPE: PRT
<213> ORGANISM: Artificial Sequence
<220> FEATURE:
<223> OTHER INFORMATION: Synthetic construct

<400> SEQUENCE: 75

Lys Gly Phe Tyr Lys Lys Gln Cys Arg Pro Ser Lys Gly Arg Lys
 1               5                  10                  15

Arg Gly Phe Cys Trp Ala Arg Ile Asp Asp Ala Ser Ser Arg Ile Asp
            20                  25                  30

Asp Leu Glu Lys Asn Ile Ala Asp Leu
        35                  40

<210> SEQ ID NO 76
<211> LENGTH: 41
<212> TYPE: PRT
<213> ORGANISM: Artificial Sequence
<220> FEATURE:
<223> OTHER INFORMATION: Synthetic construct

<400> SEQUENCE: 76

Lys Gly Phe Tyr Lys Lys Gln Cys Arg Pro Ser Lys Gly Arg Lys
 1               5                  10                  15

Arg Gly Phe Cys Trp Ala Arg Ile Asp Asp Met Ala Ser Arg Ile Asp
            20                  25                  30

Asp Leu Glu Lys Asn Ile Ala Asp Leu
        35                  40

<210> SEQ ID NO 77
<211> LENGTH: 41
<212> TYPE: PRT
<213> ORGANISM: Artificial Sequence
<220> FEATURE:
<223> OTHER INFORMATION: Synthetic construct

<400> SEQUENCE: 77

Lys Gly Phe Tyr Lys Lys Gln Cys Arg Pro Ser Lys Gly Arg Lys
 1               5                  10                  15

Arg Gly Phe Cys Trp Ala Arg Ile Asp Asp Met Ser Ala Arg Ile Asp
            20                  25                  30

Asp Leu Glu Lys Asn Ile Ala Asp Leu
        35                  40

<210> SEQ ID NO 78
<211> LENGTH: 41
<212> TYPE: PRT
<213> ORGANISM: Artificial Sequence
<220> FEATURE:
<223> OTHER INFORMATION: Synthetic construct
```

<400> SEQUENCE: 78

Lys Gly Phe Tyr Lys Lys Gln Cys Arg Pro Ser Lys Gly Arg Lys
1               5                   10                  15

Arg Gly Phe Cys Trp Ala Arg Ile Asp Asp Met Ser Ser Arg Ile Asp
            20                  25                  30

Asp Leu Ala Lys Asn Ile Ala Asp Leu
        35                  40

<210> SEQ ID NO 79
<211> LENGTH: 41
<212> TYPE: PRT
<213> ORGANISM: Artificial Sequence
<220> FEATURE:
<223> OTHER INFORMATION: Synthetic construct

<400> SEQUENCE: 79

Lys Gly Phe Tyr Lys Lys Gln Cys Arg Pro Ser Lys Gly Arg Lys
1               5                   10                  15

Arg Gly Phe Cys Trp Ala Arg Ile Asp Asp Met Ser Ser Arg Ile Asp
            20                  25                  30

Asp Leu Glu Ala Asn Ile Ala Asp Leu
        35                  40

<210> SEQ ID NO 80
<211> LENGTH: 41
<212> TYPE: PRT
<213> ORGANISM: Artificial Sequence
<220> FEATURE:
<223> OTHER INFORMATION: Synthetic construct

<400> SEQUENCE: 80

Lys Gly Phe Tyr Lys Lys Gln Cys Arg Pro Ser Lys Gly Arg Lys
1               5                   10                  15

Arg Gly Phe Cys Trp Ala Arg Ile Asp Asp Met Ser Ser Arg Ile Asp
            20                  25                  30

Asp Leu Glu Lys Ala Ile Ala Asp Leu
        35                  40

<210> SEQ ID NO 81
<211> LENGTH: 40
<212> TYPE: PRT
<213> ORGANISM: Artificial Sequence
<220> FEATURE:
<223> OTHER INFORMATION: Synthetic construct

<400> SEQUENCE: 81

Lys Gly Phe Tyr Lys Lys Gln Cys Arg Pro Ser Lys Gly Arg Lys
1               5                   10                  15

Arg Gly Phe Cys Trp Ala Arg Ile Asp Asp Met Ser Ser Arg Ile Asp
            20                  25                  30

Asp Leu Glu Lys Asn Ile Ala Asp
        35                  40

<210> SEQ ID NO 82
<211> LENGTH: 39
<212> TYPE: PRT
<213> ORGANISM: Artificial Sequence
<220> FEATURE:
<223> OTHER INFORMATION: Synthetic construct -continued

<400> SEQUENCE: 82

Lys Gly Phe Tyr Lys Lys Gln Cys Arg Pro Ser Lys Gly Arg Lys
1               5                   10                  15

Arg Gly Phe Cys Trp Ala Arg Ile Asp Asp Met Ser Ser Arg Ile Asp
            20                  25                  30

Asp Leu Glu Lys Asn Ile Ala
        35

<210> SEQ ID NO 83
<211> LENGTH: 38
<212> TYPE: PRT
<213> ORGANISM: Artificial Sequence
<220> FEATURE:
<223> OTHER INFORMATION: Synthetic construct

<400> SEQUENCE: 83

Lys Gly Phe Tyr Lys Lys Gln Cys Arg Pro Ser Lys Gly Arg Lys
1               5                   10                  15

Arg Gly Phe Cys Trp Ala Arg Ile Asp Asp Met Ser Ser Arg Ile Asp
            20                  25                  30

Asp Leu Glu Lys Asn Ile
        35

<210> SEQ ID NO 84
<211> LENGTH: 37
<212> TYPE: PRT
<213> ORGANISM: Artificial Sequence
<220> FEATURE:
<223> OTHER INFORMATION: Synthetic construct

<400> SEQUENCE: 84

Lys Gly Phe Tyr Lys Lys Gln Cys Arg Pro Ser Lys Gly Arg Lys
1               5                   10                  15

Arg Gly Phe Cys Trp Ala Arg Ile Asp Asp Met Ser Ser Arg Ile Asp
            20                  25                  30

Asp Leu Glu Lys Asn
        35

<210> SEQ ID NO 85
<211> LENGTH: 40
<212> TYPE: PRT
<213> ORGANISM: Artificial Sequence
<220> FEATURE:
<223> OTHER INFORMATION: Synthetic construct

<400> SEQUENCE: 85

Lys Gly Phe Tyr Lys Lys Gln Cys Arg Pro Ser Lys Gly Arg Lys
1               5                   10                  15

Arg Gly Phe Cys Trp Ala Ile Asp Asp Met Ser Ser Arg Ile Asp Asp
            20                  25                  30

Leu Glu Lys Asn Ile Ala Asp Leu
        35                  40

<210> SEQ ID NO 86
<211> LENGTH: 37
<212> TYPE: PRT
<213> ORGANISM: Artificial Sequence
<220> FEATURE:
<223> OTHER INFORMATION: Synthetic construct

```
<400> SEQUENCE: 86

Lys Gly Phe Tyr Lys Lys Gln Cys Arg Pro Ser Lys Gly Arg Lys
1               5                   10                  15

Arg Gly Phe Cys Trp Ala Ile Asp Asp Met Ser Ser Arg Ile Asp Asp
            20                  25                  30

Leu Glu Lys Asn Ile
        35

<210> SEQ ID NO 87
<211> LENGTH: 31
<212> TYPE: PRT
<213> ORGANISM: Artificial Sequence
<220> FEATURE:
<223> OTHER INFORMATION: Synthetic construct

<400> SEQUENCE: 87

Glu Thr Phe Ser Asp Ile Trp Lys Leu Leu Lys Gly Phe Tyr Lys Lys
1               5                   10                  15

Lys Gln Cys Arg Pro Ser Lys Gly Arg Lys Arg Gly Phe Cys Trp
            20                  25                  30

<210> SEQ ID NO 88
<211> LENGTH: 32
<212> TYPE: PRT
<213> ORGANISM: Artificial Sequence
<220> FEATURE:
<223> OTHER INFORMATION: Synthetic construct

<400> SEQUENCE: 88

Glu Thr Phe Ser Asp Ile Trp Lys Leu Leu Ala Lys Gly Phe Tyr Lys
1               5                   10                  15

Lys Lys Gln Cys Arg Pro Ser Lys Gly Arg Lys Arg Gly Phe Cys Trp
            20                  25                  30

<210> SEQ ID NO 89
<211> LENGTH: 32
<212> TYPE: PRT
<213> ORGANISM: Artificial Sequence
<220> FEATURE:
<223> OTHER INFORMATION: Synthetic construct

<400> SEQUENCE: 89

Glu Thr Phe Ser Asp Ile Trp Lys Leu Ala Lys Lys Gly Phe Tyr Lys
1               5                   10                  15

Lys Lys Gln Cys Arg Pro Ser Lys Gly Arg Lys Arg Gly Phe Cys Trp
            20                  25                  30

<210> SEQ ID NO 90
<211> LENGTH: 32
<212> TYPE: PRT
<213> ORGANISM: Artificial Sequence
<220> FEATURE:
<223> OTHER INFORMATION: Synthetic construct

<400> SEQUENCE: 90

Glu Thr Phe Ser Asp Ile Trp Lys Ala Leu Lys Lys Gly Phe Tyr Lys
1               5                   10                  15

Lys Lys Gln Cys Arg Pro Ser Lys Gly Arg Lys Arg Gly Phe Cys Trp
            20                  25                  30
```

<210> SEQ ID NO 91
<211> LENGTH: 32
<212> TYPE: PRT
<213> ORGANISM: Artificial Sequence
<220> FEATURE:
<223> OTHER INFORMATION: Synthetic construct

<400> SEQUENCE: 91

Glu Thr Phe Ser Asp Ile Trp Ala Leu Leu Lys Lys Gly Phe Tyr Lys
1               5                   10                  15

Lys Lys Gln Cys Arg Pro Ser Lys Gly Arg Lys Arg Gly Phe Cys Trp
            20                  25                  30

<210> SEQ ID NO 92
<211> LENGTH: 32
<212> TYPE: PRT
<213> ORGANISM: Artificial Sequence
<220> FEATURE:
<223> OTHER INFORMATION: Synthetic construct

<400> SEQUENCE: 92

Glu Thr Phe Ser Asp Ile Ala Lys Leu Leu Lys Lys Gly Phe Tyr Lys
1               5                   10                  15

Lys Lys Gln Cys Arg Pro Ser Lys Gly Arg Lys Arg Gly Phe Cys Trp
            20                  25                  30

<210> SEQ ID NO 93
<211> LENGTH: 32
<212> TYPE: PRT
<213> ORGANISM: Artificial Sequence
<220> FEATURE:
<223> OTHER INFORMATION: Synthetic construct

<400> SEQUENCE: 93

Glu Thr Phe Ser Asp Ala Trp Lys Leu Leu Lys Lys Gly Phe Tyr Lys
1               5                   10                  15

Lys Lys Gln Cys Arg Pro Ser Lys Gly Arg Lys Arg Gly Phe Cys Trp
            20                  25                  30

<210> SEQ ID NO 94
<211> LENGTH: 32
<212> TYPE: PRT
<213> ORGANISM: Artificial Sequence
<220> FEATURE:
<223> OTHER INFORMATION: Synthetic construct

<400> SEQUENCE: 94

Glu Thr Phe Ser Ala Ile Trp Lys Leu Leu Lys Lys Gly Phe Tyr Lys
1               5                   10                  15

Lys Lys Gln Cys Arg Pro Ser Lys Gly Arg Lys Arg Gly Phe Cys Trp
            20                  25                  30

<210> SEQ ID NO 95
<211> LENGTH: 32
<212> TYPE: PRT
<213> ORGANISM: Artificial Sequence
<220> FEATURE:
<223> OTHER INFORMATION: Synthetic construct

<400> SEQUENCE: 95

Glu Thr Phe Ala Asp Ile Trp Lys Leu Leu Lys Lys Gly Phe Tyr Lys
1               5                   10                  15

Lys Lys Gln Cys Arg Pro Ser Lys Gly Arg Lys Arg Gly Phe Cys Trp
            20                  25                  30

<210> SEQ ID NO 96
<211> LENGTH: 32
<212> TYPE: PRT
<213> ORGANISM: Artificial Sequence
<220> FEATURE:
<223> OTHER INFORMATION: Synthetic construct

<400> SEQUENCE: 96

Glu Thr Ala Ser Asp Ile Trp Lys Leu Leu Lys Lys Gly Phe Tyr Lys
 1               5                  10                  15

Lys Lys Gln Cys Arg Pro Ser Lys Gly Arg Lys Arg Gly Phe Cys Trp
            20                  25                  30

<210> SEQ ID NO 97
<211> LENGTH: 32
<212> TYPE: PRT
<213> ORGANISM: Artificial Sequence
<220> FEATURE:
<223> OTHER INFORMATION: Synthetic construct

<400> SEQUENCE: 97

Glu Ala Phe Ser Asp Ile Trp Lys Leu Leu Lys Lys Gly Phe Tyr Lys
 1               5                  10                  15

Lys Lys Gln Cys Arg Pro Ser Lys Gly Arg Lys Arg Gly Phe Cys Trp
            20                  25                  30

<210> SEQ ID NO 98
<211> LENGTH: 32
<212> TYPE: PRT
<213> ORGANISM: Artificial Sequence
<220> FEATURE:
<223> OTHER INFORMATION: Synthetic construct

<400> SEQUENCE: 98

Ala Thr Phe Ser Asp Ile Trp Lys Leu Leu Lys Lys Gly Phe Tyr Lys
 1               5                  10                  15

Lys Lys Gln Cys Arg Pro Ser Lys Gly Arg Lys Arg Gly Phe Cys Trp
            20                  25                  30

<210> SEQ ID NO 99
<211> LENGTH: 33
<212> TYPE: PRT
<213> ORGANISM: Artificial Sequence
<220> FEATURE:
<223> OTHER INFORMATION: Synthetic construct

<400> SEQUENCE: 99

Asp Glu Thr Phe Ser Asp Ile Trp Lys Leu Leu Lys Lys Gly Phe Tyr
 1               5                  10                  15

Lys Lys Lys Gln Cys Arg Pro Ser Lys Gly Arg Lys Arg Gly Phe Cys
            20                  25                  30

Trp

<210> SEQ ID NO 100
<211> LENGTH: 33
<212> TYPE: PRT
<213> ORGANISM: Artificial Sequence
<220> FEATURE:
<223> OTHER INFORMATION: Synthetic construct

```
<400> SEQUENCE: 100

Phe Glu Thr Phe Ser Asp Ile Trp Lys Leu Leu Lys Lys Gly Phe Tyr
1               5                   10                  15

Lys Lys Lys Gln Cys Arg Pro Ser Lys Gly Arg Lys Arg Gly Phe Cys
            20                  25                  30

Trp

<210> SEQ ID NO 101
<211> LENGTH: 33
<212> TYPE: PRT
<213> ORGANISM: Artificial Sequence
<220> FEATURE:
<223> OTHER INFORMATION: Synthetic construct

<400> SEQUENCE: 101

Gly Glu Thr Phe Ser Asp Ile Trp Lys Leu Leu Lys Lys Gly Phe Tyr
1               5                   10                  15

Lys Lys Lys Gln Cys Arg Pro Ser Lys Gly Arg Lys Arg Gly Phe Cys
            20                  25                  30

Trp

<210> SEQ ID NO 102
<211> LENGTH: 33
<212> TYPE: PRT
<213> ORGANISM: Artificial Sequence
<220> FEATURE:
<223> OTHER INFORMATION: Synthetic construct

<400> SEQUENCE: 102

His Glu Thr Phe Ser Asp Ile Trp Lys Leu Leu Lys Lys Gly Phe Tyr
1               5                   10                  15

Lys Lys Lys Gln Cys Arg Pro Ser Lys Gly Arg Lys Arg Gly Phe Cys
            20                  25                  30

Trp

<210> SEQ ID NO 103
<211> LENGTH: 33
<212> TYPE: PRT
<213> ORGANISM: Artificial Sequence
<220> FEATURE:
<223> OTHER INFORMATION: Synthetic construct

<400> SEQUENCE: 103

Ile Glu Thr Phe Ser Asp Ile Trp Lys Leu Leu Lys Lys Gly Phe Tyr
1               5                   10                  15

Lys Lys Lys Gln Cys Arg Pro Ser Lys Gly Arg Lys Arg Gly Phe Cys
            20                  25                  30

Trp

<210> SEQ ID NO 104
<211> LENGTH: 33
<212> TYPE: PRT
<213> ORGANISM: Artificial Sequence
<220> FEATURE:
<223> OTHER INFORMATION: Synthetic construct
```

<400> SEQUENCE: 104

Lys Glu Thr Phe Ser Asp Ile Trp Lys Leu Leu Lys Lys Gly Phe Tyr
1               5                   10                  15

Lys Lys Lys Gln Cys Arg Pro Ser Lys Gly Arg Lys Arg Gly Phe Cys
            20                  25                  30

Trp

<210> SEQ ID NO 105
<211> LENGTH: 33
<212> TYPE: PRT
<213> ORGANISM: Artificial Sequence
<220> FEATURE:
<223> OTHER INFORMATION: Synthetic construct

<400> SEQUENCE: 105

Leu Glu Thr Phe Ser Asp Ile Trp Lys Leu Leu Lys Lys Gly Phe Tyr
1               5                   10                  15

Lys Lys Lys Gln Cys Arg Pro Ser Lys Gly Arg Lys Arg Gly Phe Cys
            20                  25                  30

Trp

<210> SEQ ID NO 106
<211> LENGTH: 33
<212> TYPE: PRT
<213> ORGANISM: Artificial Sequence
<220> FEATURE:
<223> OTHER INFORMATION: Synthetic construct

<400> SEQUENCE: 106

Met Glu Thr Phe Ser Asp Ile Trp Lys Leu Leu Lys Lys Gly Phe Tyr
1               5                   10                  15

Lys Lys Lys Gln Cys Arg Pro Ser Lys Gly Arg Lys Arg Gly Phe Cys
            20                  25                  30

Trp

<210> SEQ ID NO 107
<211> LENGTH: 33
<212> TYPE: PRT
<213> ORGANISM: Artificial Sequence
<220> FEATURE:
<223> OTHER INFORMATION: Synthetic construct

<400> SEQUENCE: 107

Asn Glu Thr Phe Ser Asp Ile Trp Lys Leu Leu Lys Lys Gly Phe Tyr
1               5                   10                  15

Lys Lys Lys Gln Cys Arg Pro Ser Lys Gly Arg Lys Arg Gly Phe Cys
            20                  25                  30

Trp

<210> SEQ ID NO 108
<211> LENGTH: 33
<212> TYPE: PRT
<213> ORGANISM: Artificial Sequence
<220> FEATURE:
<223> OTHER INFORMATION: Synthetic construct -continued

<400> SEQUENCE: 108

Pro Glu Thr Phe Ser Asp Ile Trp Lys Leu Leu Lys Lys Gly Phe Tyr
1               5                   10                  15

Lys Lys Lys Gln Cys Arg Pro Ser Lys Gly Arg Lys Arg Gly Phe Cys
            20                  25                  30

Trp

<210> SEQ ID NO 109
<211> LENGTH: 33
<212> TYPE: PRT
<213> ORGANISM: Artificial Sequence
<220> FEATURE:
<223> OTHER INFORMATION: Synthetic construct

<400> SEQUENCE: 109

Gln Glu Thr Phe Ser Asp Ile Trp Lys Leu Leu Lys Lys Gly Phe Tyr
1               5                   10                  15

Lys Lys Lys Gln Cys Arg Pro Ser Lys Gly Arg Lys Arg Gly Phe Cys
            20                  25                  30

Trp

<210> SEQ ID NO 110
<211> LENGTH: 33
<212> TYPE: PRT
<213> ORGANISM: Artificial Sequence
<220> FEATURE:
<223> OTHER INFORMATION: Synthetic construct

<400> SEQUENCE: 110

Arg Glu Thr Phe Ser Asp Ile Trp Lys Leu Leu Lys Lys Gly Phe Tyr
1               5                   10                  15

Lys Lys Lys Gln Cys Arg Pro Ser Lys Gly Arg Lys Arg Gly Phe Cys
            20                  25                  30

Trp

<210> SEQ ID NO 111
<211> LENGTH: 33
<212> TYPE: PRT
<213> ORGANISM: Artificial Sequence
<220> FEATURE:
<223> OTHER INFORMATION: Synthetic construct

<400> SEQUENCE: 111

Ser Glu Thr Phe Ser Asp Ile Trp Lys Leu Leu Lys Lys Gly Phe Tyr
1               5                   10                  15

Lys Lys Lys Gln Cys Arg Pro Ser Lys Gly Arg Lys Arg Gly Phe Cys
            20                  25                  30

Trp

<210> SEQ ID NO 112
<211> LENGTH: 33
<212> TYPE: PRT
<213> ORGANISM: Artificial Sequence
<220> FEATURE:
<223> OTHER INFORMATION: Synthetic construct

```
<400> SEQUENCE: 112

Thr Glu Thr Phe Ser Asp Ile Trp Lys Leu Leu Lys Lys Gly Phe Tyr
1               5                   10                  15

Lys Lys Lys Gln Cys Arg Pro Ser Lys Gly Arg Lys Arg Gly Phe Cys
                20                  25                  30

Trp

<210> SEQ ID NO 113
<211> LENGTH: 33
<212> TYPE: PRT
<213> ORGANISM: Artificial Sequence
<220> FEATURE:
<223> OTHER INFORMATION: Synthetic construct

<400> SEQUENCE: 113

Val Glu Thr Phe Ser Asp Ile Trp Lys Leu Leu Lys Lys Gly Phe Tyr
1               5                   10                  15

Lys Lys Lys Gln Cys Arg Pro Ser Lys Gly Arg Lys Arg Gly Phe Cys
                20                  25                  30

Trp

<210> SEQ ID NO 114
<211> LENGTH: 33
<212> TYPE: PRT
<213> ORGANISM: Artificial Sequence
<220> FEATURE:
<223> OTHER INFORMATION: Synthetic construct

<400> SEQUENCE: 114

Trp Glu Thr Phe Ser Asp Ile Trp Lys Leu Leu Lys Lys Gly Phe Tyr
1               5                   10                  15

Lys Lys Lys Gln Cys Arg Pro Ser Lys Gly Arg Lys Arg Gly Phe Cys
                20                  25                  30

Trp

<210> SEQ ID NO 115
<211> LENGTH: 33
<212> TYPE: PRT
<213> ORGANISM: Artificial Sequence
<220> FEATURE:
<223> OTHER INFORMATION: Synthetic construct

<400> SEQUENCE: 115

Tyr Glu Thr Phe Ser Asp Ile Trp Lys Leu Leu Lys Lys Gly Phe Tyr
1               5                   10                  15

Lys Lys Lys Gln Cys Arg Pro Ser Lys Gly Arg Lys Arg Gly Phe Cys
                20                  25                  30

Trp

<210> SEQ ID NO 116
<211> LENGTH: 41
<212> TYPE: PRT
<213> ORGANISM: Artificial Sequence
<220> FEATURE:
<223> OTHER INFORMATION: Synthetic construct
```

-continued

```
<400> SEQUENCE: 116

Lys Gly Phe Tyr Lys Lys Gln Cys Arg Pro Ser Lys Gly Arg Lys
1               5                   10                  15

Arg Gly Phe Cys Trp Ala Val Gln Thr Leu Leu Gln Gln Met Gln Asp
            20                  25                  30

Lys Phe Gln Thr Met Ser Asp Gln Ile
        35                  40

<210> SEQ ID NO 117
<211> LENGTH: 40
<212> TYPE: PRT
<213> ORGANISM: Artificial Sequence
<220> FEATURE:
<223> OTHER INFORMATION: Synthetic construct

<400> SEQUENCE: 117

Lys Gly Phe Tyr Lys Lys Gln Cys Arg Pro Ser Lys Gly Arg Lys
1               5                   10                  15

Arg Gly Phe Cys Trp Ala Val Gln Thr Leu Leu Gln Gln Met Gln Asp
            20                  25                  30

Lys Phe Gln Thr Met Ser Asp Gln
        35                  40

<210> SEQ ID NO 118
<211> LENGTH: 39
<212> TYPE: PRT
<213> ORGANISM: Artificial Sequence
<220> FEATURE:
<223> OTHER INFORMATION: Synthetic construct

<400> SEQUENCE: 118

Lys Gly Phe Tyr Lys Lys Gln Cys Arg Pro Ser Lys Gly Arg Lys
1               5                   10                  15

Arg Gly Phe Cys Trp Ala Val Gln Thr Leu Leu Gln Gln Met Gln Asp
            20                  25                  30

Lys Phe Gln Thr Met Ser Asp
        35

<210> SEQ ID NO 119
<211> LENGTH: 38
<212> TYPE: PRT
<213> ORGANISM: Artificial Sequence
<220> FEATURE:
<223> OTHER INFORMATION: Synthetic construct

<400> SEQUENCE: 119

Lys Gly Phe Tyr Lys Lys Gln Cys Arg Pro Ser Lys Gly Arg Lys
1               5                   10                  15

Arg Gly Phe Cys Trp Ala Val Gln Thr Leu Leu Gln Gln Met Gln Asp
            20                  25                  30

Lys Phe Gln Thr Met Ser
        35

<210> SEQ ID NO 120
<211> LENGTH: 40
<212> TYPE: PRT
<213> ORGANISM: Artificial Sequence
<220> FEATURE:
<223> OTHER INFORMATION: Synthetic construct
```

-continued

<400> SEQUENCE: 120

Lys Gly Phe Tyr Lys Lys Gln Cys Arg Pro Ser Lys Gly Arg Lys
1               5                   10                  15

Arg Gly Phe Cys Trp Ala Gln Thr Leu Leu Gln Gln Met Gln Asp Lys
            20                  25                  30

Phe Gln Thr Met Ser Asp Gln Ile
        35                  40

<210> SEQ ID NO 121
<211> LENGTH: 39
<212> TYPE: PRT
<213> ORGANISM: Artificial Sequence
<220> FEATURE:
<223> OTHER INFORMATION: Synthetic construct

<400> SEQUENCE: 121

Lys Gly Phe Tyr Lys Lys Gln Cys Arg Pro Ser Lys Gly Arg Lys
1               5                   10                  15

Arg Gly Phe Cys Trp Ala Thr Leu Leu Gln Gln Met Gln Asp Lys Phe
            20                  25                  30

Gln Thr Met Ser Asp Gln Ile
        35

<210> SEQ ID NO 122
<211> LENGTH: 38
<212> TYPE: PRT
<213> ORGANISM: Artificial Sequence
<220> FEATURE:
<223> OTHER INFORMATION: Synthetic construct

<400> SEQUENCE: 122

Lys Gly Phe Tyr Lys Lys Gln Cys Arg Pro Ser Lys Gly Arg Lys
1               5                   10                  15

Arg Gly Phe Cys Trp Ala Leu Leu Gln Gln Met Gln Asp Lys Phe Gln
            20                  25                  30

Thr Met Ser Asp Gln Ile
        35

<210> SEQ ID NO 123
<211> LENGTH: 41
<212> TYPE: PRT
<213> ORGANISM: Artificial Sequence
<220> FEATURE:
<223> OTHER INFORMATION: Synthetic construct

<400> SEQUENCE: 123

Lys Gly Phe Tyr Lys Lys Gln Cys Arg Pro Ser Lys Gly Arg Lys
1               5                   10                  15

Arg Gly Phe Cys Trp Ala Val Gln Thr Leu Leu Gln Gln Met Gln Ala
            20                  25                  30

Lys Phe Gln Thr Met Ser Asp Gln Ile
        35                  40

<210> SEQ ID NO 124
<211> LENGTH: 41
<212> TYPE: PRT
<213> ORGANISM: Artificial Sequence
<220> FEATURE:
<223> OTHER INFORMATION: Synthetic construct

```
<400> SEQUENCE: 124

Lys Gly Phe Tyr Lys Lys Gln Cys Arg Pro Ser Lys Gly Arg Lys
1               5                   10                  15

Arg Gly Phe Cys Trp Ala Val Gln Thr Leu Leu Gln Gln Met Gln Asp
            20                  25                  30

Lys Phe Gln Thr Met Ser Ala Gln Ile
        35                  40

<210> SEQ ID NO 125
<211> LENGTH: 35
<212> TYPE: PRT
<213> ORGANISM: Artificial Sequence
<220> FEATURE:
<223> OTHER INFORMATION: Synthetic construct

<400> SEQUENCE: 125

Lys Gly Phe Tyr Lys Lys Gln Cys Arg Pro Ser Lys Gly Arg Lys
1               5                   10                  15

Arg Gly Phe Cys Trp Ala Leu Leu Gln Gln Met Gln Asp Lys Phe Gln
            20                  25                  30

Thr Met Ser
        35

<210> SEQ ID NO 126
<211> LENGTH: 40
<212> TYPE: PRT
<213> ORGANISM: Artificial Sequence
<220> FEATURE:
<223> OTHER INFORMATION: Synthetic construct

<400> SEQUENCE: 126

Arg Glu Ser Leu Arg Asn Leu Arg Gly Tyr Tyr Lys Lys Gln Cys
1               5                   10                  15

Arg Pro Ser Lys Gly Arg Lys Arg Gly Phe Cys Trp Ala Val Ala Glu
            20                  25                  30

Tyr Ala Arg Val Gln Lys Arg Lys
        35                  40

<210> SEQ ID NO 127
<211> LENGTH: 35
<212> TYPE: PRT
<213> ORGANISM: Artificial Sequence
<220> FEATURE:
<223> OTHER INFORMATION: Synthetic construct

<400> SEQUENCE: 127

Arg Glu Ser Leu Arg Asn Leu Arg Gly Tyr Tyr Lys Cys Asn Trp Ala
1               5                   10                  15

Pro Pro Phe Lys Ala Arg Cys Ala Val Ala Glu Tyr Ala Arg Val Gln
            20                  25                  30

Lys Arg Lys
        35

<210> SEQ ID NO 128
<211> LENGTH: 41
<212> TYPE: PRT
<213> ORGANISM: Artificial Sequence
<220> FEATURE:
<223> OTHER INFORMATION: Synthetic construct
```

```
<400> SEQUENCE: 128

Leu Glu Thr Phe Ser Asp Ile Trp Lys Leu Leu Lys Gly Phe Tyr Lys
1               5                   10                  15

Lys Lys Gln Cys Arg Pro Ser Lys Gly Arg Lys Arg Gly Phe Cys Trp
            20                  25                  30

Ala Leu Tyr Trp Asp Leu Tyr Glu Met
        35                  40

<210> SEQ ID NO 129
<211> LENGTH: 41
<212> TYPE: PRT
<213> ORGANISM: Artificial Sequence
<220> FEATURE:
<223> OTHER INFORMATION: Synthetic construct

<400> SEQUENCE: 129

Leu Leu Gln Gln Met Gln Asp Lys Phe Gln Thr Met Ser Cys Asn Trp
1               5                   10                  15

Ala Pro Pro Phe Lys Ala Val Cys Gly Arg Ile Asp Ala Met Ser Ser
            20                  25                  30

Arg Ile Asp Asp Leu Glu Lys Asn Ile
        35                  40

<210> SEQ ID NO 130
<211> LENGTH: 34
<212> TYPE: PRT
<213> ORGANISM: Artificial Sequence
<220> FEATURE:
<223> OTHER INFORMATION: Synthetic construct

<400> SEQUENCE: 130

Ile Arg Leu Lys Val Phe Val Leu Gly Gly Ser Arg His Lys Gly Phe
1               5                   10                  15

Tyr Lys Lys Lys Gln Cys Arg Pro Ser Lys Gly Arg Lys Arg Gly Phe
            20                  25                  30

Cys Trp

<210> SEQ ID NO 131
<211> LENGTH: 32
<212> TYPE: PRT
<213> ORGANISM: Artificial Sequence
<220> FEATURE:
<223> OTHER INFORMATION: Synthetic construct

<400> SEQUENCE: 131

Lys Lys Gly Phe Tyr Lys Lys Lys Gln Cys Arg Pro Ser Lys Gly Arg
1               5                   10                  15

Lys Arg Gly Phe Cys Trp Lys Pro Leu Tyr Trp Asp Leu Tyr Glu Ile
            20                  25                  30

<210> SEQ ID NO 132
<211> LENGTH: 32
<212> TYPE: PRT
<213> ORGANISM: Artificial Sequence
<220> FEATURE:
<223> OTHER INFORMATION: Synthetic construct

<400> SEQUENCE: 132

Lys Lys Gly Phe Tyr Lys Lys Lys Gln Cys Arg Pro Ser Lys Gly Arg
1               5                   10                  15

Lys Arg Gly Phe Cys Trp Lys Pro Leu Tyr Trp Asp Leu Tyr Glu Met
            20                  25                  30
```

```
<210> SEQ ID NO 133
<211> LENGTH: 32
<212> TYPE: PRT
<213> ORGANISM: Artificial Sequence
<220> FEATURE:
<223> OTHER INFORMATION: Synthetic construct

<400> SEQUENCE: 133

Lys Lys Gly Phe Tyr Lys Lys Lys Gln Cys Arg Pro Ser Lys Gly Arg
1               5                   10                  15

Lys Arg Gly Phe Cys Trp Lys Pro Leu Tyr Trp Asp Leu Tyr Glu Pro
            20                  25                  30

<210> SEQ ID NO 134
<211> LENGTH: 31
<212> TYPE: PRT
<213> ORGANISM: Artificial Sequence
<220> FEATURE:
<223> OTHER INFORMATION: Synthetic construct

<400> SEQUENCE: 134

Lys Lys Gly Phe Tyr Lys Lys Lys Gln Cys Arg Pro Ser Lys Gly Arg
1               5                   10                  15

Lys Arg Gly Phe Cys Trp Lys Pro Leu Tyr Trp Ala Leu Tyr Glu
            20                  25                  30

<210> SEQ ID NO 135
<211> LENGTH: 31
<212> TYPE: PRT
<213> ORGANISM: Artificial Sequence
<220> FEATURE:
<223> OTHER INFORMATION: Synthetic construct

<400> SEQUENCE: 135

Lys Lys Gly Phe Tyr Lys Lys Lys Gln Cys Arg Pro Ser Lys Gly Arg
1               5                   10                  15

Lys Arg Gly Phe Cys Trp Ala Pro Leu Tyr Trp Asp Leu Tyr Glu
            20                  25                  30

<210> SEQ ID NO 136
<211> LENGTH: 31
<212> TYPE: PRT
<213> ORGANISM: Artificial Sequence
<220> FEATURE:
<223> OTHER INFORMATION: Synthetic construct

<400> SEQUENCE: 136

Ala Lys Gly Phe Tyr Lys Lys Lys Gln Cys Arg Pro Ser Lys Gly Arg
1               5                   10                  15

Lys Arg Gly Phe Cys Trp Lys Pro Leu Tyr Trp Asp Leu Tyr Glu
            20                  25                  30

<210> SEQ ID NO 137
<211> LENGTH: 31
<212> TYPE: PRT
<213> ORGANISM: Artificial Sequence
<220> FEATURE:
<223> OTHER INFORMATION: Synthetic construct

<400> SEQUENCE: 137

Lys Ala Gly Phe Tyr Lys Lys Lys Gln Cys Arg Pro Ser Lys Gly Arg
1               5                   10                  15

Lys Arg Gly Phe Cys Trp Lys Pro Leu Tyr Trp Asp Leu Tyr Glu
            20                  25                  30
```

```
<210> SEQ ID NO 138
<211> LENGTH: 31
<212> TYPE: PRT
<213> ORGANISM: Artificial Sequence
<220> FEATURE:
<223> OTHER INFORMATION: Synthetic construct

<400> SEQUENCE: 138

Lys Lys Ala Phe Tyr Lys Lys Lys Gln Cys Arg Pro Ser Lys Gly Arg
1               5                   10                  15

Lys Arg Gly Phe Cys Trp Lys Pro Leu Tyr Trp Asp Leu Tyr Glu
            20                  25                  30

<210> SEQ ID NO 139
<211> LENGTH: 31
<212> TYPE: PRT
<213> ORGANISM: Artificial Sequence
<220> FEATURE:
<223> OTHER INFORMATION: Synthetic construct

<400> SEQUENCE: 139

Lys Lys Gly Ala Tyr Lys Lys Lys Gln Cys Arg Pro Ser Lys Gly Arg
1               5                   10                  15

Lys Arg Gly Phe Cys Trp Lys Pro Leu Tyr Trp Asp Leu Tyr Glu
            20                  25                  30

<210> SEQ ID NO 140
<211> LENGTH: 31
<212> TYPE: PRT
<213> ORGANISM: Artificial Sequence
<220> FEATURE:
<223> OTHER INFORMATION: Synthetic construct

<400> SEQUENCE: 140

Lys Lys Gly Phe Ala Lys Lys Lys Gln Cys Arg Pro Ser Lys Gly Arg
1               5                   10                  15

Lys Arg Gly Phe Cys Trp Lys Pro Leu Tyr Trp Asp Leu Tyr Glu
            20                  25                  30

<210> SEQ ID NO 141
<211> LENGTH: 31
<212> TYPE: PRT
<213> ORGANISM: Artificial Sequence
<220> FEATURE:
<223> OTHER INFORMATION: Synthetic construct

<400> SEQUENCE: 141

Lys Lys Gly Phe Tyr Ala Lys Lys Gln Cys Arg Pro Ser Lys Gly Arg
1               5                   10                  15

Lys Arg Gly Phe Cys Trp Lys Pro Leu Tyr Trp Asp Leu Tyr Glu
            20                  25                  30

<210> SEQ ID NO 142
<211> LENGTH: 31
<212> TYPE: PRT
<213> ORGANISM: Artificial Sequence
<220> FEATURE:
<223> OTHER INFORMATION: Synthetic construct

<400> SEQUENCE: 142

Lys Lys Gly Phe Tyr Lys Ala Lys Gln Cys Arg Pro Ser Lys Gly Arg
1               5                   10                  15

Lys Arg Gly Phe Cys Trp Lys Pro Leu Tyr Trp Asp Leu Tyr Glu
            20                  25                  30
```

```
<210> SEQ ID NO 143
<211> LENGTH: 31
<212> TYPE: PRT
<213> ORGANISM: Artificial Sequence
<220> FEATURE:
<223> OTHER INFORMATION: Synthetic construct

<400> SEQUENCE: 143

Lys Gly Phe Tyr Lys Lys Ala Gln Cys Arg Pro Ser Lys Gly Arg
 1               5                  10                  15

Lys Arg Gly Phe Cys Trp Lys Pro Leu Tyr Trp Asp Leu Tyr Glu
            20                  25                  30

<210> SEQ ID NO 144
<211> LENGTH: 31
<212> TYPE: PRT
<213> ORGANISM: Artificial Sequence
<220> FEATURE:
<223> OTHER INFORMATION: Synthetic construct

<400> SEQUENCE: 144

Lys Lys Gly Phe Tyr Lys Lys Ala Cys Arg Pro Ser Lys Gly Arg
 1               5                  10                  15

Lys Arg Gly Phe Cys Trp Lys Pro Leu Tyr Trp Asp Leu Tyr Glu
            20                  25                  30

<210> SEQ ID NO 145
<211> LENGTH: 31
<212> TYPE: PRT
<213> ORGANISM: Artificial Sequence
<220> FEATURE:
<223> OTHER INFORMATION: Synthetic construct

<400> SEQUENCE: 145

Lys Lys Gly Phe Tyr Lys Lys Gln Cys Ala Pro Ser Lys Gly Arg
 1               5                  10                  15

Lys Arg Gly Phe Cys Trp Lys Pro Leu Tyr Trp Asp Leu Tyr Glu
            20                  25                  30

<210> SEQ ID NO 146
<211> LENGTH: 31
<212> TYPE: PRT
<213> ORGANISM: Artificial Sequence
<220> FEATURE:
<223> OTHER INFORMATION: Synthetic construct

<400> SEQUENCE: 146

Lys Lys Gly Phe Tyr Lys Lys Gln Cys Arg Ala Ser Lys Gly Arg
 1               5                  10                  15

Lys Arg Gly Phe Cys Trp Lys Pro Leu Tyr Trp Asp Leu Tyr Glu
            20                  25                  30

<210> SEQ ID NO 147
<211> LENGTH: 31
<212> TYPE: PRT
<213> ORGANISM: Artificial Sequence
<220> FEATURE:
<223> OTHER INFORMATION: Synthetic construct

<400> SEQUENCE: 147

Lys Lys Gly Phe Tyr Lys Lys Gln Cys Arg Pro Ala Lys Gly Arg
 1               5                  10                  15

Lys Arg Gly Phe Cys Trp Lys Pro Leu Tyr Trp Asp Leu Tyr Glu
            20                  25                  30
```

```
<210> SEQ ID NO 148
<211> LENGTH: 31
<212> TYPE: PRT
<213> ORGANISM: Artificial Sequence
<220> FEATURE:
<223> OTHER INFORMATION: Synthetic construct

<400> SEQUENCE: 148

Lys Lys Gly Phe Tyr Lys Lys Lys Gln Cys Arg Pro Ser Ala Gly Arg
 1               5                  10                  15

Lys Arg Gly Phe Cys Trp Lys Pro Leu Tyr Trp Asp Leu Tyr Glu
            20                  25                  30

<210> SEQ ID NO 149
<211> LENGTH: 31
<212> TYPE: PRT
<213> ORGANISM: Artificial Sequence
<220> FEATURE:
<223> OTHER INFORMATION: Synthetic construct

<400> SEQUENCE: 149

Lys Lys Gly Phe Tyr Lys Lys Lys Gln Cys Arg Pro Ser Lys Ala Arg
 1               5                  10                  15

Lys Arg Gly Phe Cys Trp Lys Pro Leu Tyr Trp Asp Leu Tyr Glu
            20                  25                  30

<210> SEQ ID NO 150
<211> LENGTH: 31
<212> TYPE: PRT
<213> ORGANISM: Artificial Sequence
<220> FEATURE:
<223> OTHER INFORMATION: Synthetic construct

<400> SEQUENCE: 150

Lys Lys Gly Phe Tyr Lys Lys Lys Gln Cys Arg Pro Ser Lys Gly Ala
 1               5                  10                  15

Lys Arg Gly Phe Cys Trp Lys Pro Leu Tyr Trp Asp Leu Tyr Glu
            20                  25                  30

<210> SEQ ID NO 151
<211> LENGTH: 31
<212> TYPE: PRT
<213> ORGANISM: Artificial Sequence
<220> FEATURE:
<223> OTHER INFORMATION: Synthetic construct

<400> SEQUENCE: 151

Lys Lys Gly Phe Tyr Lys Lys Lys Gln Cys Arg Pro Ser Lys Gly Arg
 1               5                  10                  15

Ala Arg Gly Phe Cys Trp Lys Pro Leu Tyr Trp Asp Leu Tyr Glu
            20                  25                  30

<210> SEQ ID NO 152
<211> LENGTH: 31
<212> TYPE: PRT
<213> ORGANISM: Artificial Sequence
<220> FEATURE:
<223> OTHER INFORMATION: Synthetic construct

<400> SEQUENCE: 152

Lys Lys Gly Phe Tyr Lys Lys Lys Gln Cys Arg Pro Ser Lys Gly Arg
 1               5                  10                  15

Lys Ala Gly Phe Cys Trp Lys Pro Leu Tyr Trp Asp Leu Tyr Glu
            20                  25                  30
```

```
<210> SEQ ID NO 153
<211> LENGTH: 31
<212> TYPE: PRT
<213> ORGANISM: Artificial Sequence
<220> FEATURE:
<223> OTHER INFORMATION: Synthetic construct

<400> SEQUENCE: 153

Lys Lys Gly Phe Tyr Lys Lys Lys Gln Cys Arg Pro Ser Lys Gly Arg
1               5                   10                  15

Lys Arg Ala Phe Cys Trp Lys Pro Leu Tyr Trp Asp Leu Tyr Glu
            20                  25                  30

<210> SEQ ID NO 154
<211> LENGTH: 31
<212> TYPE: PRT
<213> ORGANISM: Artificial Sequence
<220> FEATURE:
<223> OTHER INFORMATION: Synthetic construct

<400> SEQUENCE: 154

Lys Lys Gly Phe Tyr Lys Lys Lys Gln Cys Arg Pro Ser Lys Gly Arg
1               5                   10                  15

Lys Arg Gly Ala Cys Trp Lys Pro Leu Tyr Trp Asp Leu Tyr Glu
            20                  25                  30

<210> SEQ ID NO 155
<211> LENGTH: 31
<212> TYPE: PRT
<213> ORGANISM: Artificial Sequence
<220> FEATURE:
<223> OTHER INFORMATION: Synthetic construct

<400> SEQUENCE: 155

Lys Lys Gly Phe Tyr Lys Lys Lys Gln Cys Arg Pro Ser Lys Gly Arg
1               5                   10                  15

Lys Arg Gly Phe Cys Ala Lys Pro Leu Tyr Trp Asp Leu Tyr Glu
            20                  25                  30

<210> SEQ ID NO 156
<211> LENGTH: 31
<212> TYPE: PRT
<213> ORGANISM: Artificial Sequence
<220> FEATURE:
<223> OTHER INFORMATION: Synthetic construct

<400> SEQUENCE: 156

Lys Lys Gly Phe Tyr Lys Lys Lys Gln Cys Arg Pro Ser Lys Gly Arg
1               5                   10                  15

Lys Arg Gly Phe Cys Trp Lys Pro Ala Tyr Trp Asp Leu Tyr Glu
            20                  25                  30

<210> SEQ ID NO 157
<211> LENGTH: 31
<212> TYPE: PRT
<213> ORGANISM: Artificial Sequence
<220> FEATURE:
<223> OTHER INFORMATION: Synthetic construct

<400> SEQUENCE: 157

Lys Lys Gly Phe Tyr Lys Lys Lys Gln Cys Arg Pro Ser Lys Gly Arg
1               5                   10                  15

Lys Arg Gly Phe Cys Trp Lys Pro Leu Ala Trp Asp Leu Tyr Glu
            20                  25                  30
```

```
<210> SEQ ID NO 158
<211> LENGTH: 31
<212> TYPE: PRT
<213> ORGANISM: Artificial Sequence
<220> FEATURE:
<223> OTHER INFORMATION: Synthetic construct

<400> SEQUENCE: 158

Lys Lys Gly Phe Tyr Lys Lys Lys Gln Cys Arg Pro Ser Lys Gly Arg
1               5                   10                  15

Lys Arg Gly Phe Cys Trp Lys Pro Leu Tyr Ala Asp Leu Tyr Glu
            20                  25                  30

<210> SEQ ID NO 159
<211> LENGTH: 31
<212> TYPE: PRT
<213> ORGANISM: Artificial Sequence
<220> FEATURE:
<223> OTHER INFORMATION: Synthetic construct

<400> SEQUENCE: 159

Lys Lys Gly Phe Tyr Lys Lys Lys Gln Cys Arg Pro Ser Lys Gly Arg
1               5                   10                  15

Lys Arg Gly Phe Cys Trp Lys Pro Leu Tyr Trp Asp Ala Tyr Glu
            20                  25                  30

<210> SEQ ID NO 160
<211> LENGTH: 31
<212> TYPE: PRT
<213> ORGANISM: Artificial Sequence
<220> FEATURE:
<223> OTHER INFORMATION: Synthetic construct

<400> SEQUENCE: 160

Lys Lys Gly Phe Tyr Lys Lys Lys Gln Cys Arg Pro Ser Lys Gly Arg
1               5                   10                  15

Lys Arg Gly Phe Cys Trp Lys Pro Leu Tyr Trp Asp Leu Ala Glu
            20                  25                  30

<210> SEQ ID NO 161
<211> LENGTH: 31
<212> TYPE: PRT
<213> ORGANISM: Artificial Sequence
<220> FEATURE:
<223> OTHER INFORMATION: Synthetic construct

<400> SEQUENCE: 161

Lys Lys Gly Phe Tyr Lys Lys Lys Gln Cys Arg Pro Ser Lys Gly Arg
1               5                   10                  15

Lys Arg Gly Phe Cys Trp Lys Pro Leu Tyr Trp Asp Leu Tyr Ala
            20                  25                  30

<210> SEQ ID NO 162
<211> LENGTH: 32
<212> TYPE: PRT
<213> ORGANISM: Artificial Sequence
<220> FEATURE:
<223> OTHER INFORMATION: Synthetic construct

<400> SEQUENCE: 162

Lys Lys Gly Phe Tyr Lys Lys Lys Gln Cys Arg Pro Ser Lys Gly Arg
1               5                   10                  15

Lys Arg Gly Phe Cys Trp Lys Pro Leu Tyr Trp Asp Leu Tyr Glu Ala
            20                  25                  30
```

```
<210> SEQ ID NO 163
<211> LENGTH: 32
<212> TYPE: PRT
<213> ORGANISM: Artificial Sequence
<220> FEATURE:
<223> OTHER INFORMATION: Synthetic construct

<400> SEQUENCE: 163

Lys Lys Gly Phe Tyr Lys Lys Lys Gln Cys Arg Pro Ser Lys Gly Arg
1               5                   10                  15

Lys Arg Gly Phe Cys Trp Lys Pro Leu Tyr Trp Asp Leu Tyr Glu Asp
            20                  25                  30

<210> SEQ ID NO 164
<211> LENGTH: 32
<212> TYPE: PRT
<213> ORGANISM: Artificial Sequence
<220> FEATURE:
<223> OTHER INFORMATION: Synthetic construct

<400> SEQUENCE: 164

Lys Lys Gly Phe Tyr Lys Lys Lys Gln Cys Arg Pro Ser Lys Gly Arg
1               5                   10                  15

Lys Arg Gly Phe Cys Trp Lys Pro Leu Tyr Trp Asp Leu Tyr Glu Phe
            20                  25                  30

<210> SEQ ID NO 165
<211> LENGTH: 32
<212> TYPE: PRT
<213> ORGANISM: Artificial Sequence
<220> FEATURE:
<223> OTHER INFORMATION: Synthetic construct

<400> SEQUENCE: 165

Lys Lys Gly Phe Tyr Lys Lys Lys Gln Cys Arg Pro Ser Lys Gly Arg
1               5                   10                  15

Lys Arg Gly Phe Cys Trp Lys Pro Leu Tyr Trp Asp Leu Tyr Glu Gly
            20                  25                  30

<210> SEQ ID NO 166
<211> LENGTH: 32
<212> TYPE: PRT
<213> ORGANISM: Artificial Sequence
<220> FEATURE:
<223> OTHER INFORMATION: Synthetic construct

<400> SEQUENCE: 166

Lys Lys Gly Phe Tyr Lys Lys Lys Gln Cys Arg Pro Ser Lys Gly Arg
1               5                   10                  15

Lys Arg Gly Phe Cys Trp Lys Pro Leu Tyr Trp Asp Leu Tyr Glu His
            20                  25                  30

<210> SEQ ID NO 167
<211> LENGTH: 32
<212> TYPE: PRT
<213> ORGANISM: Artificial Sequence
<220> FEATURE:
<223> OTHER INFORMATION: Synthetic construct

<400> SEQUENCE: 167

Lys Lys Gly Phe Tyr Lys Lys Lys Gln Cys Arg Pro Ser Lys Gly Arg
1               5                   10                  15

Lys Arg Gly Phe Cys Trp Lys Pro Leu Tyr Trp Asp Leu Tyr Glu Trp
            20                  25                  30
```

```
<210> SEQ ID NO 168
<211> LENGTH: 32
<212> TYPE: PRT
<213> ORGANISM: Artificial Sequence
<220> FEATURE:
<223> OTHER INFORMATION: Synthetic construct

<400> SEQUENCE: 168

Lys Lys Gly Phe Tyr Lys Lys Lys Gln Cys Arg Pro Ser Lys Gly Arg
 1               5                  10                  15

Lys Arg Gly Phe Cys Trp Lys Pro Leu Tyr Trp Asp Leu Tyr Glu Lys
            20                  25                  30

<210> SEQ ID NO 169
<211> LENGTH: 32
<212> TYPE: PRT
<213> ORGANISM: Artificial Sequence
<220> FEATURE:
<223> OTHER INFORMATION: Synthetic construct

<400> SEQUENCE: 169

Lys Lys Gly Phe Tyr Lys Lys Lys Gln Cys Arg Pro Ser Lys Gly Arg
 1               5                  10                  15

Lys Arg Gly Phe Cys Trp Lys Pro Leu Tyr Trp Asp Leu Tyr Glu Leu
            20                  25                  30

<210> SEQ ID NO 170
<211> LENGTH: 32
<212> TYPE: PRT
<213> ORGANISM: Artificial Sequence
<220> FEATURE:
<223> OTHER INFORMATION: Synthetic construct

<400> SEQUENCE: 170

Lys Lys Gly Phe Tyr Lys Lys Lys Gln Cys Arg Pro Ser Lys Gly Arg
 1               5                  10                  15

Lys Arg Gly Phe Cys Trp Lys Pro Leu Tyr Trp Asp Leu Tyr Glu Asn
            20                  25                  30

<210> SEQ ID NO 171
<211> LENGTH: 32
<212> TYPE: PRT
<213> ORGANISM: Artificial Sequence
<220> FEATURE:
<223> OTHER INFORMATION: Synthetic construct

<400> SEQUENCE: 171

Lys Lys Gly Phe Tyr Lys Lys Lys Gln Cys Arg Pro Ser Lys Gly Arg
 1               5                  10                  15

Lys Arg Gly Phe Cys Trp Lys Pro Leu Tyr Trp Asp Leu Tyr Glu Gln
            20                  25                  30

<210> SEQ ID NO 172
<211> LENGTH: 32
<212> TYPE: PRT
<213> ORGANISM: Artificial Sequence
<220> FEATURE:
<223> OTHER INFORMATION: Synthetic construct

<400> SEQUENCE: 172

Lys Lys Gly Phe Tyr Lys Lys Lys Gln Cys Arg Pro Ser Lys Gly Arg
 1               5                  10                  15

Lys Arg Gly Phe Cys Trp Lys Pro Leu Tyr Trp Asp Leu Tyr Glu Arg
            20                  25                  30
```

```
<210> SEQ ID NO 173
<211> LENGTH: 32
<212> TYPE: PRT
<213> ORGANISM: Artificial Sequence
<220> FEATURE:
<223> OTHER INFORMATION: Synthetic construct

<400> SEQUENCE: 173

Lys Lys Gly Phe Tyr Lys Lys Lys Gln Cys Arg Pro Ser Lys Gly Arg
 1               5                  10                  15

Lys Arg Gly Phe Cys Trp Lys Pro Leu Tyr Trp Asp Leu Tyr Glu Ser
             20                  25                  30

<210> SEQ ID NO 174
<211> LENGTH: 32
<212> TYPE: PRT
<213> ORGANISM: Artificial Sequence
<220> FEATURE:
<223> OTHER INFORMATION: Synthetic construct

<400> SEQUENCE: 174

Lys Lys Gly Phe Tyr Lys Lys Lys Gln Cys Arg Pro Ser Lys Gly Arg
 1               5                  10                  15

Lys Arg Gly Phe Cys Trp Lys Pro Leu Tyr Trp Asp Leu Tyr Glu Thr
             20                  25                  30

<210> SEQ ID NO 175
<211> LENGTH: 32
<212> TYPE: PRT
<213> ORGANISM: Artificial Sequence
<220> FEATURE:
<223> OTHER INFORMATION: Synthetic construct

<400> SEQUENCE: 175

Lys Lys Gly Phe Tyr Lys Lys Lys Gln Cys Arg Pro Ser Lys Gly Arg
 1               5                  10                  15

Lys Arg Gly Phe Cys Trp Lys Pro Leu Tyr Trp Asp Leu Tyr Glu Val
             20                  25                  30

<210> SEQ ID NO 176
<211> LENGTH: 27
<212> TYPE: PRT
<213> ORGANISM: Artificial Sequence
<220> FEATURE:
<223> OTHER INFORMATION: Synthetic construct

<400> SEQUENCE: 176

Lys Lys Gly Phe Tyr Lys Lys Lys Gln Cys Arg Pro Ser Lys Gly Arg
 1               5                  10                  15

Lys Arg Gly Phe Cys Trp Cys Val Asp Lys Tyr
             20                  25

<210> SEQ ID NO 177
<211> LENGTH: 18
<212> TYPE: PRT
<213> ORGANISM: Artificial Sequence
<220> FEATURE:
<223> OTHER INFORMATION: Synthetic construct

<400> SEQUENCE: 177

Lys Lys Gly His Ala Lys Asp Ser Gln Arg Tyr Lys Val Asp Glu Ser
 1               5                  10                  15

Gln Ser
```

```
<210> SEQ ID NO 178
<211> LENGTH: 9
<212> TYPE: PRT
<213> ORGANISM: Artificial Sequence
<220> FEATURE:
<223> OTHER INFORMATION: Synthetic construct

<400> SEQUENCE: 178

Lys Lys Gly Phe Tyr Lys Lys Lys Gln
 1               5

<210> SEQ ID NO 179
<211> LENGTH: 18
<212> TYPE: PRT
<213> ORGANISM: Artificial Sequence
<220> FEATURE:
<223> OTHER INFORMATION: Synthetic construct

<400> SEQUENCE: 179

Lys Lys Gly Phe Tyr Lys Lys Lys Gln Cys Arg Pro Ser Lys Gly Arg
 1               5                  10                  15

Lys Arg

<210> SEQ ID NO 180
<211> LENGTH: 11
<212> TYPE: PRT
<213> ORGANISM: Artificial Sequence
<220> FEATURE:
<223> OTHER INFORMATION: Synthetic construct

<400> SEQUENCE: 180

Pro Val Gln Arg Lys Arg Gln Lys Leu Met Pro
 1               5                  10

<210> SEQ ID NO 181
<211> LENGTH: 14
<212> TYPE: PRT
<213> ORGANISM: Artificial Sequence
<220> FEATURE:
<223> OTHER INFORMATION: Synthetic construct

<400> SEQUENCE: 181

Gln Thr Leu Leu Gln Gln Met Gln Asp Lys Phe Gln Thr Met
 1               5                  10

<210> SEQ ID NO 182
<211> LENGTH: 10
<212> TYPE: PRT
<213> ORGANISM: Artificial Sequence
<220> FEATURE:
<223> OTHER INFORMATION: Synthetic construct

<400> SEQUENCE: 182

Glu Thr Phe Ser Asp Ile Trp Lys Leu Leu
 1               5                  10

<210> SEQ ID NO 183
<211> LENGTH: 14
<212> TYPE: PRT
<213> ORGANISM: Artificial Sequence
<220> FEATURE:
<223> OTHER INFORMATION: Synthetic construct
```

```
<400> SEQUENCE: 183

Ile Arg Leu Lys Val Phe Val Leu Gly Gly Ser Arg His Lys
1               5                   10

<210> SEQ ID NO 184
<211> LENGTH: 9
<212> TYPE: PRT
<213> ORGANISM: Artificial Sequence
<220> FEATURE:
<223> OTHER INFORMATION: Synthetic construct

<400> SEQUENCE: 184

Lys Ala Leu Tyr Trp Asp Leu Tyr Glu
1               5

<210> SEQ ID NO 185
<211> LENGTH: 12
<212> TYPE: PRT
<213> ORGANISM: Artificial Sequence
<220> FEATURE:
<223> OTHER INFORMATION: Synthetic construct

<400> SEQUENCE: 185

Gly Leu Gly Glu Phe Leu Lys Leu Asp Arg Glu Arg
1               5                   10

<210> SEQ ID NO 186
<211> LENGTH: 9
<212> TYPE: PRT
<213> ORGANISM: Artificial Sequence
<220> FEATURE:
<223> OTHER INFORMATION: Synthetic construct

<400> SEQUENCE: 186

Ala Leu Asp Trp Ser Trp Leu Gln Thr
1               5

<210> SEQ ID NO 187
<211> LENGTH: 11
<212> TYPE: PRT
<213> ORGANISM: Artificial Sequence
<220> FEATURE:
<223> OTHER INFORMATION: Synthetic construct

<400> SEQUENCE: 187

Val Ala Glu Tyr Ala Arg Val Gln Lys Arg Lys
1               5                   10
```

METAL-BINDING THERAPEUTIC PEPTIDES

CROSS-REFERENCE TO RELATED APPLICATIONS

This application claims the benefit of U.S. Provisional Application 60/735,529, filed Nov. 9, 2005, and U.S. Provisional Application 60/789,100 filed Apr. 3, 2006, each application is hereby incorporated by reference in its entirety.

TECHNICAL FIELD

The invention relates to the field of medical diagnostics and therapeutics, and more particularly to therapeutic peptides selectively active on human disease. The invention also relates to methods of delivering MBD peptide-linked agents into live cells.

BACKGROUND ART

The so-called diseases of western civilization (chronic conditions such as arthritis, asthma, osteoporosis, and atherosclerosis, other cardiovascular diseases, cancers of the breast, prostate and colon, metabolic syndrome-related conditions such as diabetes and polycystic ovary syndrome (PCOS), neurodegenerative conditions such as Parkinson's and Alzheimer's, and ophthalmic diseases such as macular degeneration) are now increasingly being viewed as secondary to chronic inflammatory conditions and adiposity. A direct link between adiposity and inflammation has recently been demonstrated. Macrophages, potent donors of pro-inflammatory signals, are nominally responsible for this link: Obesity is marked by macrophage accumulation in adipose tissue (Weisberg S P et al [2003] J. Clin Invest 112: 1796-1808) and chronic inflammation in fat plays a crucial role in the development of obesity-related insulin resistance (Xu H, et al [2003] J. Clin Invest. 112: 1821-1830). Inflammatory cytokine IL-18 is associated with PCOS, insulin resistance and adiposity (Escobar-Morreale H F, et al [2004] J. Clin Endo Metab 89: 806-811). Systemic inflammatory markers such as CRP are associated with unstable carotid plaque, specifically, the presence of macrophages in plaque, which is associated with instability can lead to the development of an ischemic event (Alvarez Garcia B et al [2003] J Vasc Surg 38: 1018-1024). There are documented cross-relationships between these risk factors. For example, there is higher than normal cardiovascular risk in patients with rheumatoid arthritis (RA) (Dessein P H et al [2003] Arthritis Res. 4: R5) and elevated C-peptide (insulin resistance) is associated with increased risk of colorectal cancer (Ma J et al [2004] J. Natl Cancer Inst 96:546-553) and breast cancer (Malin A. et al [2004] Cancer 100: 694-700).

The genesis of macrophage involvement with diseased tissues is not yet fully understood, though various theories postulating the "triggering" effect of some secondary challenge (such as viral infection) have been advanced. What is observed is vigorous crosstalk between macrophages, T-cells, and resident cell types at the sites of disease. For example, the direct relationship of macrophages to tumor progression has been documented. In many solid tumor types, the abundance of macrophages is correlated with prognosis (Lin E Y and Pollard J W [2004] Novartis Found Symp 256: 158-168). Reduced macrophage population levels are associated with prostate tumor progression (Yang G et al [2004] Cancer Res 64:2076-2082) and the "tumor-like behavior of rheumatoid synovium" has also been noted (Firestein G S [2003] Nature 423: 356-361). At sites of inflammation, macrophages elaborate cytokines such as interleukin-1-beta and interleukin-6.

A ubiquitous observation in chronic inflammatory stress is the up-regulation of heat shock proteins (HSP) at the site of inflammation, followed by macrophage infiltration, oxidative stress and the elaboration of cytokines leading to stimulation of growth of local cell types. For example, this has been observed with unilateral obstructed kidneys, where the sequence results in tubulointerstitial fibrosis and is related to increases in HSP70 in human patients (Valles, P. et al [2003] Pediatr Nephrol. 18: 527-535). HSP70 is required for the survival of cancer cells (Nylandsted J et al [2000] Ann NY Acad Sci 926: 122-125). Eradication of glioblastoma, breast and colon xenografts by HSP70 depletion has been demonstrated (Nylansted J et al [2002] Cancer Res 62:7139-7142; Rashmi R et al [2004] Carcinogenesis 25: 179-187) and blocking HSF1 by expressing a dominant-negative mutant suppresses growth of a breast cancer cell line (Wang J H et al [2002] BBRC 290: 1454-1461). It is hypothesized that stress-induced extracellular HSP72 promotes immune responses and host defense systems. In vitro, rat macrophages are stimulated by HSP72, elevating NO, TNF-alpha, IL-1-beta and IL-6 (Campisi J et al [2003] Cell Stress Chaperones 8: 272-86). Significantly higher levels of (presumably secreted) HSP70 were found in the sera of patients with acute infection compared to healthy subjects and these levels correlated with levels of IL-6, TNF-alpha, IL-10 (Njemini R et al [2003] Scand. J. Immunol 58: 664-669). HSP70 is postulated to maintain the inflammatory state in asthma by stimulating pro-inflammatory cytokine production from macrophages (Harkins M S et al [2003] Ann Allergy Asthma Immunol 91: 567-574). In esophageal carcinoma, lymph node metastasis is associated with reduction in both macrophage populations and HSP70 expression (Noguchi T. et al [2003] Oncol. 10: 1161-1164). HSPs are a possible trigger for autoimmunity (Purcell A W et al [2003] Clin Exp Immunol. 132: 193-200). There is aberrant extracellular expression of HSP70 in rheumatoid joints (Martin C A et al [2003] J. Immunol 171: 5736-5742). Even heterologous HSPs can modulate macrophage behavior: *H. pylori* HSP60 mediates IL-6 production by macrophages in chronically inflamed gastric tissues (Gobert A P et al [2004] J. Biol. Chem 279: 245-250).

In addition to immunological stress, a variety of environmental conditions can trigger cellular stress programs. For example, heat shock (thermal stress), anoxia, high osmotic conditions, hyperglycemia, nutritional stress, endoplasmic reticulum (ER) stress and oxidative stress each can generate cellular responses, often involving the induction of stress proteins such as HSP70.

About 40,000 women will die from metastatic breast cancer in the U.S. this year. Current interventions focus on the use of chemotherapeutic and biological agents to treat disseminated disease, but these treatments almost invariably fail in time. At earlier stages of the disease, treatment is demonstrably more successful: systemic adjuvant therapy has been studied in more than 400 randomized clinical trials, and has proven to reduce rates of recurrence and death more than 15 years after treatment (Hortobagyi G N. (1998) *N Engl J Med*. 339 (14): 974-984). The same studies have shown that combinations of drugs are more effective than just one drug alone for breast cancer treatment. However, such treatments significantly lower the patient's quality of life, and have limited efficacy. Moreover, they may not address slow-replicating tumor reservoirs that could serve as the source of subsequent disease recurrence and metastasis. A successful approach to the treatment of recurrent metastatic disease must address the genetic heterogeneity of the diseased cell population by simultaneously targeting multiple mechanisms of the disease such as dysregulated growth rates and enhanced survival from (a) up-regulated stress-coping and anti-apoptotic mechanisms, and (b) dispersion to sequestered and privileged sites such as spleen and bone marrow. Cellular diversification, which leads to metastasis, produces both rapid and slow growing cells. Slow-growing disseminated cancer cells may differ from normal cells in that they are located outside their 'normal' tissue context and may up-regulate both anti-apoptotic and stress-coping survival mechanisms. Global comparison of cancer cells to their normal counterparts reveals underlying distinctions in system logic. Cancer cells display up-regulated stress-coping and anti-apoptotic mechanisms (e.g. NF-kappa-B, Hsp-70, MDM2, survivin etc.) to successfully evade cell death (Chong Y P, et al. (2005) *Growth Factors*. September; 23 (3): 233-44; Rao R D, et al (2005) *Neoplasia*. October; 7 (10): 921-9; Nebbioso A, et al (2005) *Nat Med*. January; 11 (1): 77-84). Many tumor types contain high concentrations of heat-shock proteins (HSP) of the HSP27, HSP70, and HSP90 families compared with adjacent normal tissues (Ciocca at al 1993; Yano et al 1999; Cornford at al 2000; Strik et al 2000; Ricaniadis et al 2001; Ciocca and Vargas-Roig 2002). The role of HSPs in tumor development may be related to their function in the development of tolerance to stress (Li and Hahn 1981) and high levels of HSP expression seem to be a factor in tumor pathogenesis. Among other mechanisms individual HSPs can block pathways of apoptosis (Volloch and Sherman 1999). Studies show HSP70 is required for the survival of cancer cells (Nylandsted J, Brand K, Jaattela M. (2000) *Ann NY Acad Sci*. 926: 122-125). Eradication of glioblastoma, breast and colon xenografts by HSP70 depletion has been demonstrated, but the same treatment had no effect on the survival or growth of fetal fibroblasts or non-tumorigenic epithelial cells of breast (Nylandsted J, et al (2002) *Cancer Res*. 62 (24): 7139-7142; Rashmi R, Kumar S, Karunagaran D. (2004) *Carcinogenesis*. 25 (2): 179-187; Barnes J A, et al. (2001) *Cell Stress Chaperones*. 6 (4): 316-325) and blocking HSF1 by expressing a dominant-negative mutant suppresses growth of a breast cancer cell line (Wang J H, et al. (2002) *Biochem Biophys Res Commun*. 290 (5): 1454-1461). Stress can also activate the nuclear factor kappa B (NF-kappa B) transcription factor family. NF-kappa-B is a central regulator of the inflammation response that regulates the expression of anti-apoptotic genes, such as cyclooxygenases (COX) and metalloproteinases (MMPs), thereby favoring tumor cell proliferation and dissemination. NF-kappa-B can be successfully inhibited by peptides interfering with its intracellular transport and/or stability (Butt A J, et al. (2005) *Endocrinology*. July; 146 (7): 3113-22). Human survivin, an inhibitor of apoptosis, is highly expressed in various tumors (Ambrosini G, Adida C, Altieri D C. (1997) *Nat. Med*. 3 (8): 917-921) aberrantly prolonging cell viability and contributing to cancer. It has been shown that ectopic expression of survivin can protect cells against apoptosis (Li F, et al. (1999) *Nat. Cell Biol*. 1 (8): 461-466). Tumor suppressor p53 is a transcription factor that induces growth arrest and/or apoptosis in response to cellular stress. Peptides modeled on the MDM2-binding pocket of p53 can inhibit the negative feedback of MDM2 on p53 commonly observed in cancer cells (Midgley C A, et al. (2000) *Oncogene*. May 4; 19 (19): 2312-23; Zhang R, et al. (2004) *Anal Biochem*. August 1; 331 (1): 138-46). The role of protein degradation rates and the proteasome in disease has recently come to light. Inhibitors of HSP90 (a key component of protein degradation complexes) such as bortezomib are in clinical testing and show promise as cancer therapeutics (Mitsiades C S, et al. 2006 *Curr Drug Targets*. 7(10):1341-1347).

A C-terminal metal-binding domain (MBD) of insulin-like growth factor binding protein-3 (IGFBP-3) can rapidly (<10 min) mobilize large proteins from the extracellular milieu into the nuclei of target cells (Singh B K, et al. (2004) *J Biol Chem*. 279: 477-487). Here we extend these observations to show that MBD is a systemic 'guidance system' that attaches to the surface of red blood cells and can mediate rapid intracellular transport of its 'payload' into the cytoplasm and nucleus of target cells at privileged sites such as spleen and bone marrow in vivo. The amino acid sequence of these MBD peptides can be extended to include domains known to inhibit HSP, survivin, NF-kappa-B, proteasome and other intracellular mechanisms. The MBD mediates transport to privileged tissues and intracellular locations (such as the nucleus) in the target tissue. In this study we ask whether such MBD-tagged peptides might act as biological modifiers to selectively enhance the efficacy of existing treatment modalities against cancer cells. Patients presenting with metastatic disease generally face a poor prognosis. The median survival from the time of initial diagnosis of bone metastasis is 2 years with only 20% surviving 5 years (Antman et al. (1999) *JAMA*.; 282: 1701-1703; Lipton A. (2005) North American Pharmacotherapy: 109-112). A successful systemic treatment for recurrent metastatic disease is the primary unmet medical need in cancer.

Diabetes is a rapidly expanding epidemic in industrial societies. The disease is caused by the body's progressive inability to manage glucose metabolism appropriately. Insulin production by pancreatic islet cells is a highly regulated process that is essential for the body's management of carbohydrate metabolism. In diabetes, these cells are lost or impaired, and efforts to stimulate the body's ability to generate new islet cells have met with limited success. The INGAP peptide IGLHDPSHGTLPNGS (SEQ ID NO: 1) has been used to stimulate differentiation of islet cell precursors in cell culture and animal models (Petropavlovskaia M., et al (2006) J Endocrinol. 191(1): 65-81; Yamaoka T, Itakura M. (1999) Int J Mol Med. 3(3): 247-61; Rosenberg L. (1998) Microsc Res Tech. 43(4): 337-46), however delivery of the peptide in vivo is complicated, possibly for lack of a suitable delivery mechanism. The INGAP protein, from which the peptide sequence is derived, works primarily at an intracellular location. There is thus a need for suitable delivery technologies to deliver the INGAP peptide or protein therapeutically to the appropriate cellular locations in the body.

Familial mutations in parkin gene are associated with early-onset PD. Parkinson's disease (PD) is characterized by the selective degeneration of dopaminergic (DA) neurons in the substantia nigra pars compacta (SNpc). A combination of genetic and environmental factors contributes to such a specific loss, which is characterized by the accumulation of misfolded protein within dopaminergic neurons. Among the five PD-linked genes identified so far, parkin, a 52 kD protein-ubiquitin E3 ligase, appears to be the most prevalent genetic factor in PD. Mutations in parkin cause autosomal recessive juvenile parkinsonism (AR-JP). The current therapy for Parkinson's disease is aimed to replace the lost transmitter, dopamine. But the ultimate objective in neurodegenerative therapy is the functional restoration and/or cessation of progression of neuronal loss (Jiang H, et al [2004] *Hum Mol Genet*. 13 (16): 1745-54; Muqit M M, et al [2004] *Hum Mol Genet*. 13 (1): 117-135; Goldberg M S, et al [2003] *J Biol Chem*. 278 (44): 43628-43635). Over-expressed parkin protein alleviates PD pathology in experimental systems. Recent molecular dissection of the genetic requirements for hypoxia, excitotoxicity and death in models of Alzheimer disease, polyglutamine-expansion disorders, Parkinson disease and more, is providing mechanistic insights into neurotoxicity and suggesting new therapeutic interventions. An emerging theme is that neuronal crises of distinct origins might converge to disrupt common cellular functions, such as protein folding and turnover (Driscoll M, and Gerstbrein B. [2003] *Nat Rev Genet*. 4(3): 181-194). In PC12 cells, neuronally differentiated by nerve growth factor, parkin overproduction protected against cell death mediated by ceramide Protection was abrogated by the proteasome inhibitor epoxomicin and disease-causing variants, indicating that it was mediated by the E3 ubiquitin ligase activity of parkin. (Darios F. et al [2003] *Hum Mol Genet*. 12 (5): 517-526). Overexpressed parkin suppresses toxicity induced by mutant (A53T) and wt alpha-synuclein in SHSY-5Y cells (Oluwatosin-Chigbu Y. et al [2003] *Biochem Biophys Res Commun*. 309 (3): 679-684) and also reverses synucleinopathies in invertebrates (Haywood A F and Staveley B E. [2004] *BMC Neurosci*. 5(1): 14) and rodents (Yamada M, Mizuno Y, Mochizuki H. (2005) Parkin gene therapy for alpha-synucleinopathy: a rat model of Parkinson's disease. *Hum Gene Ther*. 16(2): 262-270; Lo Bianco C. et al [2004] *Proc Natl Acad Sci USA*. 101(50): 17510-17515). On the other hand, a recent report claims that parkin-deficient mice are not themselves a robust model for the disease (Perez F A and Palmiter R D [2005] *Proc Natl Acad Sci USA*. 102 (6): 2174-2179). Nevertheless, parkin therapy has been suggested for PD (Butcher J. [2005] *Lancet Neurol*. 4(2): 82).

Variability within patient populations creates numerous problems for medical treatment. Without reliable means for determining which individuals will respond to a given treatment, physicians are forced to resort to trial and error. Because not all patients will respond to a given therapy, the trial and error approach means that some portion of the patients must suffer the side effects (as well as the economic costs) of a treatment that is not effective in that patient.

For some therapeutics targeted to specific molecules within the body, screening to determine eligibility for the treatment is routinely performed. For example, the estrogen antagonist tamoxifen targets the estrogen receptor, so it is normal practice to only administer tamoxifen to those patients whose tumors express the estrogen receptor. Likewise, the anti-tumor agent trastuzumab (HERCEPTIN®) acts by binding to a cell surface molecule known as HER2/neu; patients with HER2/neu negative tumors are not normally eligible for treatment with trastuzumab. Methods for predicting whether a patient will respond to treatment with IGF-I/IGFBP-3 complex have also been disclosed (U.S. Pat. No. 5,824,467), as well as methods for creating predictive models of responsiveness to a particular treatment (U.S. Pat. No. 6,087,090).

IGFBP-3 is a master regulator of cellular function and viability. As the primary carrier of IGFs in the circulation, it plays a central role in sequestering, delivering and releasing IGFs to target tissues in response to physiological parameters such as nutrition, trauma, and pregnancy. IGFs, in turn, modulate cell growth, survival and differentiation, Additionally, IGFBP-3 can sensitize selected target cells to apoptosis in an IGF-independent manner. The mechanisms by which it accomplishes the latter class of effects is not well understood but appears to involve selective cell internalization mechanisms and vesicular transport to specific cellular compartments (such as the nucleus, where it may interact with transcriptional elements) that is at least partially dependent on transferrin receptor, integrins and caveolin.

The inventor has previously disclosed certain IGFBP-derived peptides known as "MBD" peptides (U.S. patent application publication nos. 2003/0059430, 2003/0161829, and 2003/0224990). These peptides have a number of properties, which are distinct from the IGF-binding properties of IGFBPs, that make them useful as therapeutic agents. MBD peptides are internalized some cells, and the peptides can be used as cell internalization signals to direct the uptake of molecules joined to the MBD peptides (such as proteins fused to the MBD peptide).

All references cited herein, including patent applications and publications, are incorporated by reference in their entirety.

SUMMARY OF THE INVENTION

The present invention provides compositions comprising a polypeptide having an amino acid sequence QCRPSKGRKRGFCW (SEQ ID NO: 2) linked to a second polypeptide which exhibits binding affinity to a substantially purified intracellular molecular target. Administration of said composition to a mammal causes a clinically useful outcome.

In preferred embodiments of the invention the intracellular molecular target of the second polypeptide is selected from but is not limited to NF-kappa-B regulator domain, P53 regulator domain, IGF-signaling regulator domain, survivin dimerization domain, proteasome subunit regulator domain, RAS active site domain, MYC regulator domain, HSP regulator domain and HIF1-alpha oxygen-dependent regulator domain.

In some embodiments of the invention, the first polypeptide is fused to the second polypeptide and in other embodiments of the invention the first polypeptide is conjugated to the second polypeptide.

In a preferred embodiment of the invention, the second polypeptide is an antibody or a fragment thereof.

The present invention provides methods of treating inflammatory disease conditions by administering an effective amount of the composition of the invention to a mammal. Inflammatory disease conditions include but are not limited to cancer, diabetes, cardiovascular disease, obesity, metabolic disease, neurodegenerative disease, gastrointestinal disease, autoimmune disease, rheumatological disease and infectious disease.

In embodiments of the invention, the composition can be administered via any route including but not limited to intravenous, oral, subcutaneous, intraarterial, intramuscular, intracardial, intraspinal, intrathoracic, intraperitoneal, intraventricular, sublingual, transdermal, and inhalation.

The present invention also provides nucleic acids encoding a fusion polypeptide which includes the amino acid sequence QCRPSKGRKRGFCW (SEQ ID NO: 2) and a second polypeptide which exhibits binding affinity to a substantially purified intracellular molecular target.

In an embodiment of the invention, nucleic acids encoding fusion proteins are used in methods of treating an inflammatory disease condition. Inflammatory disease conditions include but are not limited to cancer, diabetes, cardiovascular disease, obesity, metabolic disease, neurodegenerative disease, gastrointestinal disease, autoimmune disease, rheumatological disease and infectious disease.

The present invention provides the administration of dietary compounds curcumin and lycopene to treat subjects with an inflammatory disease condition including but not limited to cancer, diabetes, cardiovascular disease, obesity, metabolic disease, neurodegenerative disease, gastrointestinal disease, autoimmune disease, rheumatological disease and infectious disease.

In a preferred embodiment, compositions of the invention comprised of the amino acid sequence QCRPSKGRKRG- FCW (SEQ ID NO: 2) linked to a second polypeptide which exhibits binding affinity to a substantially purified intracellular molecular target is administered in conjunction with the dietary compounds curcumin and lycopene to treat subjects with an inflammatory disease condition.

DISCLOSURE OF THE INVENTION

The present invention provides a method for delivering an MBD peptide-linked agent into live cells, said method comprising contacting said MBD peptide-linked agent to live cells that are under a condition of cellular stress, whereby said contact results in cellular uptake of said MBD-peptide-linked agent.

The invention also provides a method for obtaining diagnostic information from live cells comprising the steps of: (a) administering an MBD peptide-linked agent to live cells that are under a condition of cellular stress; and (b) measuring a diagnostic readout. The diagnostic readout can be an enzymatic, a calorimetric, or a fluorimetric readout.

The invention also provides a method for modifying in a disease process or a cellular process, said method comprising the steps of: (a) administering an MBD peptide-linked agent to live cells that are under a condition of cellular stress, wherein the agent is capable of modifying the disease process or the cellular process within said live cells; and (b) delivering said MBD peptide-linked agent into said live cells, whereby said disease process or said cellular process in said live cells is modified. In some embodiments, the disease process is selected from the group consisting of neurodegenerative, cancer, autoimmune, inflammatory, cardiovascular, diabetes, osteoporosis and ophthalmic diseases. In some embodiments, the cellular process is selected from the group consisting of transcriptional, translational, protein folding, protein degradation and protein phosphorylation events.

In some embodiments, the condition of cellular stress is selected from the group consisting of thermal, immunological, cytokine, oxidative, metabolic, anoxic, endoplasmic reticulum, protein unfolding, nutritional, chemical, mechanical, osmotic and glycemic stress. In some embodiments, the condition of cellular stress is associated with upregulation of at least about 1.5-fold of at least one of the genes shown in FIG. 7. In some embodiments, at least two, at least three, at least four, at least five, at least ten, at least fifteen, at least twenty, or all of the genes shown in FIG. 7 are upregulated at least about 1.5-fold in the live cells under the condition of cellular stress compared to same type of live cells not under the condition of cellular stress.

In some embodiments, the methods described herein further comprise a step or steps for identifying the cells for delivering the MBD peptide-linked agent into the cells. Such steps may include comparing levels of gene expression of one or more of the genes shown in FIG. 7 in cells under the condition of cellular stress to levels of gene expression in the same type of cells not under the condition of cellular stress, and selecting cells that have at least one, at least two, at least three, at least four, at least five, at least ten, at least fifteen, at least twenty, or all of the genes shown in FIG. 7 upregulated at least about 1.5-fold under the condition of cellular stress for delivering the MBD peptide-linked agent into the cells.

The agent linked to the MBD peptide may be a diagnostic agent or a therapeutic agent. In some embodiments, the agent is a protein or a peptide. In some embodiments, the agent is a nucleic acid. In some embodiments, the agent is a small molecule.

In some embodiments, the live cells are in a subject, such as a mammal. For example, the live cells are in a human. In some embodiments, the live cells are in a tissue or in cell culture.

Any MBD peptide described in U.S. Patent Application Nos. 2003/0059430, 2003/0161829, and 2003/0224990 (which are incorporated by reference in their entirety) may be used. In some embodiments, the MBD peptide comprises the amino acid sequence QCRPSKGRKRGFCW (SEQ ID NO: 2), QCRPSKGRRRGFCWAVDKYG (SEQ ID NO: 3), or KKGFYKKKQCRPSKGRKRGFCWAVDKYG (SEQ ID NO: 4).

The invention provides methods for identifying individuals who are candidates for treatment with MBD peptide-based therapies. MBD peptide-based therapies have been previously described in U.S. patent application publication nos. 2003/0059430, 2003/0161829, and 2003/0224990. However, the inventor has noted that there is variability in cellular internalization of MBD peptides. The invention provides methods for identifying which patients would be candidates for treatment with MBD peptide-based therapies, by predicting whether the relevant tissue(s) in the individual will take up MBD peptides.

In this invention I show that the physiological cellular state for which up-regulation of HSPs is emblematic is also the preferred state recognized by the MBD for cellular uptake and nuclear localization. MBD-mediated transport of appropriate macromolecules into cell nuclei at the sites of disease could allow for fine-tuned control of the disease process and for the design of very specific interventions. The possibility of delivery to sites of injury is also attractive. Liver injury leads to transcription of HSPs (Schiaffonati L and Tiberio L [1997] Liver. 17: 183-191) as does ischemia in isolated hearts (Nitta-Komatsubara Y et al [2000] 66:1261-1270). HSF1 is cardioprotective for ischemia/reperfusion injury (Zou Y et al [2003] Circulation 108: 3024-3030). This invention also provides for treatment of disorders characterized by secreted HSP70 and macrophage co-localized at the site of disease.

Privileged sites in the body also up-regulate HSPs constitutively, though most other cell types only induce HSPs as a specific response to stress. HSFs are required for spermatogenesis (Wang G et al [2004] Genesis 38: 66-80). Neuronal cells also display altered regulation of HSPs (Kaarniranta K et al [2002] Mol Brain Res 101:136-140). Longevity in *C. elegans* is regulated by HSF and chaperones (Morley J F and Morimoto R I. [2004] Mol Biol Cell 15:657-664). MBD-mediated transport of regulatory macromolecules to such sites offers opportunities for interventions in neuroprotection and reproductive biology.

It is interesting that Kupffer cells (macrophage-like) are the major site of synthesis of IGFBP-3 in the liver (Scharf J et al [1996] Hepatology 23: 818-827; Zimmermann E M et al [2000] Am J. Physiol. Gastro. Liver Phys. 278: G447-457). Exogenously administered radiolabelled IGFBP-3 selectively accumulates in rat liver Kupffer cells (Arany E et al [1996] Growth Regul 6:32-41). Our earlier work suggested that caveolin and transferrin receptor were implicated in MBD-mediated cellular uptake. Caveolin is expressed in macrophages (Kiss A L et al [2002] Micron. 33: 75-93). Macrophage caveolin-1 is up-regulated in response to apoptotic stressors (Gargalovic P and Dory L [2003] J Lipid Res 44: 1622-1632). Macrophages express transferrin receptor (Mulero V and Brock J H [1999] Blood 94:2383-2389).

We are interested in elucidating the physiological and biochemical correlates of cellular receptivity to IGFBP-3, uptake and intracellular localization. We have recently localized and characterized the minimal sequence determinants of cellular recognition, uptake and intracellular localization to a C-terminal metal-binding domain in the IGFBP-3 molecule. This domain, when to covalently linked to unrelated protein molecules such as GFP, can mediate specific cellular uptake and intracellular localization of such markers in selected cell systems. As a surrogate for the homing mechanism of IGFBP-3 itself, MBD-linked marker proteins can serve to elucidate patterns of cellular receptivity that might otherwise be difficult or impossible to discern against a background of endogenous IGFBP-3.

Heat shock proteins are molecular chaperones, involved in many cellular functions such as protein folding, transport, maturation and degradation. Since they control the quality of newly synthesized proteins, HSP take part in cellular homeostasis. The Hsp70 family in particular exerts these functions in an adenosine triphosphate (ATP)-dependent manner. ATP is the main energy source used by cells to assume fundamental functions (respiration, proliferation, differentiation, apoptosis). Therefore, ATP levels have to be adapted to the requirements of the cells and ATP generation must constantly compensate ATP consumption. Nevertheless, under particular stress conditions, ATP levels decrease, threatening cell homeostasis and integrity. Cells have developed adaptive and protective mechanisms, among which Hsp70 synthesis and over-expression is one.

Transferrin serves as the iron source for hemoglobin-synthesizing immature red blood cells. A cell surface receptor, transferrin receptor 1, is required for iron delivery from transferrin to cells. Transferrin receptor 1 has been established as a gatekeeper for regulating iron uptake by most cells. Iron uptake is viewed as an indicator of cellular oxidative metabolism and ATP-dependent metabolic rates.

In this study, we have dissected the molecular signatures of cells that selectively take up MBD-tagged markers.

By gene array and cellular protein analysis we have demonstrated that MBD-mediated protein uptake is linked to target cell physiological states resembling cellular responses to stress or injury. Thermal stress dramatically up-regulates uptake of MBD-tagged proteins. In vivo, inflammatory stress in an adjuvant arthritis rat model did not change the biodistribution of systemically administered MBD-tagged proteins. We are currently evaluating other in vivo and in vitro models of cellular stress.

Therapeutic peptides incorporating the MBD motif can be created by making fusions of peptide sequences known to have appropriate intracellular biological activities with either the N- or C-terminus of the core MBD sequence. Based on prior studies, peptide sequences can be selected to target up-regulated stress proteins (such as hsp70) in cancer, as well as MDM2 interactions with P53, inflammation (NF-kappa-B, NEMO, CSK), and previously characterized cancer-specific targets such as survivin and bcl-2.

Metastasis is the primary cause of cancer-related mortality in the world. Our goal is to address this unmet need by enhancing existing chemotherapeutic cocktails with the addition of synergistic biological modifiers. We show that intracardiac injection of CCRF-CEM (T-cell leukemia), MDA-MB-435 or MDA-MB-231 (breast cancer) cells into Rag-2 mice establishes disseminated disease within a few days. The 22-amino acid MBD transporter, derived from IGFBP-3, targets malignant cancer cells via cell surface transferrin receptors and beta integrins. In vitro data show that MBD-linked peptides can inhibit stress-coping and anti-apoptotic mechanisms, commonly up-regulated in cancer (e.g. NF-kappa-B, Hsp-70, MDM2, survivin). The discriminant validity of these peptides as potential therapeutic agents was investigated by comparing their cytotoxicity to cancer cell lines versus normal human cell counterparts. In cell culture, synergies between these peptides as well as in combination with dietary supplements (lycopene and curcumin) and paclitaxel or 5-FU have been shown. 25-day intravenous administration of a 3-peptide cocktail (3 mg/kg) in combination with dietary lycopene and curcumin in Rag-2 mice with established CCRF-CEM leukemia significantly reduces splenomegaly from human cell burden, and improves survival. Similarly, 25-day administration of a 3-peptide cocktail and dietary supplement optimized for breast cancer reduces MDA-MB-231 human cell burden in bone marrow. Our data suggest that MBD-tagged peptides can be used to treat hematological and disseminated malignancies.

The human cancer and corresponding normal cell lines to be used in testing can be obtained from the American Type Culture Collection (ATCC). They are well characterized and have been extensively used in vitro and in vivo. Breast cancer cell lines (MCF7, MDA-MB-231, MX-1), leukemia cell lines (RPMI-8226, CCRF-CEM, MOLT-4), and prostate cancer cell lines (PC3, DU145, LNCAPs) were cultured in RPMI-1640 media supplemented with 10% FBS. Paired breast cancer and non-cancer cell lines (CRL7364/CRL7365, CRL7481/CRL7482, HTB-125/Hs578T) were cultured in DMEM media supplemented with 10% FBS. Normal cell lines such as MCF-10A, HMEC human T-cells were cultured in medias specified by the manufacturer.

Animal models of metastatic disease are described in this invention. Successful engraftment of both human hematopoietic and non-hematopoietic xenografts requires the use of severe combined immunodeficient (SCID) mice as neither bone marrow involvement nor disseminated growth are regularly observed using thymectomized, irradiated or nude mice. The mice used to establish a human-mouse xenograft model were purchased from Taconic. Mice were bred by crossing C57BL/6J gc KO mice to C57BL/10SgSnAi Rag-2 deficient mice. The gc KO is a deletion of the X-chromosome linked gc gene resulting in a loss of NK cells, a loss of the common g receptor unit shared by an array of cytokines that include IL-2, IL-4, IL-7, IL-9, and IL-15, and as a result only a residual number of T and B cells are produced. To eliminate this residual number of T and B cells, the gc mouse KO mouse was crossed with a C57BL/10SgSnAi recombinase activating-2 (Rag-2) deficient mouse (a loss of the Rag-2 gene results in an inability to initiate V(D)J lymphocyte receptor rearrangements, and mice will lack mature lymphocytes). CCRF-CEM, MDA-MB-231 or MDA-MB-435 xenograft-bearing Rag-2 mice (10 mice per group, 3 groups, approx. $5 \times 10^5$ to $1 \times 10^7$ cancer cells injected per animal per group) are established through intra-cardiac injection. MBD-tagged peptide cocktails ("enhancers") and paclitaxel combinations are intraperitoneally (IP) injected into the animals. The groups are divided as follows: saline (group 1), peptide (group 2), and peptide/paclitaxel combination (group 3). Treatment is started on Day 4 with a one-time IP dosage of paclitaxel (group 3). On Day 6, the paclitaxel dose (0.5 mg/kg) is followed by peptide treatment for 7 days (groups 2 and 3). On a daily basis, each mouse receives IP injection of MBD peptide cocktails (in one embodiment, 3 peptide sequences are combined in one cocktail, each peptide administered at a dose of 0.1-5.0 mg/kg). Blood sampling and PCR analysis are carried out at weekly intervals. Approximately 100 ul blood is collected from the saphenous vein. PCR analysis is used on peripheral blood (PB) on Days 3-7 post-injection to determine whether animals have successfully established leukemia/cancer. Cancer cell count levels are monitored during and after treatment as well as at termination. PCR analysis on PB, bone marrow, spleen, liver and lung is used to quantify the cancer cells. At Day 3, prior to treatment, high levels of cancer cells may be seen in PB in the case of leukemia models and low levels of human cancer cells in peripheral organs. Blood and peripheral organs are collected at termination and stored for further analysis (Day 18-45, depending on the experiment). If dietary compounds such as curcumin or lycopene are to be used in the experiment they may be included in the animal diet or force-fed daily or at other specified intervals. It has been shown that blood levels exceeding 20 nM can be achieved for these compounds when fed orally. Dietary supplements curcumin and lycopene were purchased from Sigma. Chemotherapeutics paclitaxel and 5-fluorouracil (5-Fm can be purchased from Sigma. Biphosphonates (Alendronate, Clodronate) have been obtained from EMD Biosciences. At termination of each animal experiment blood and organs are collected and stored at −80° C. To isolate genomic DNA (gDNA) from blood samples the blood & cell culture DNA kit (purchased from Qiagen Inc., Carlsbad, Calif.) can be used to isolate gDNA from tissue samples. gDNA concentrations are established based on spectrophotometer $OD_{260}$ readings. To determine human genomic DNA human-specific primers 5'-TAGCAATAATCCCCATCCTCCATATAT-3' (SEQ ID NO: 5) and 5'-ACTTGTCCAATGATGG-TAAAAGG-3' (SEQ ID NO: 6), which amplify a 157-bp portion of the human mitochondrial cytochrome b region can be used with 100-500 ng input genomic DNA per PCR reaction, depending on type of tissue. Good results can be achieved using the KOD hot start PCR kit (Novagen, Inc., Madison, Wis.). PCR is performed in a thermal cycler (Perkin Elmer) for 25 or 32 cycles of 30 s at 96° C., 40 s at 59° C., and 1 mm at 72° C. The program can be optimized for genomic DNA isolated from mouse tissue.

BRIEF DESCRIPTION OF THE DRAWINGS

FIG. 3 shows the nuclear uptake of conjugate of various MBD and GFP (SEQ ID NOS: 2, 9, 177, 178, and 179).

FIG. 4 shows the uptake of MBD-mobilized SA-HRP by tumor cell lines. A broad collection of anatomical sites was used in this survey.

FIG. 5 shows cell internalization of MBD-mobilized SA-HRP in tumor cell lines. For each of the selected anatomical sites, a pair of cell lines was chosen based on the results shown in Table 2.

FIG. 6 shows cell internalization of MBD-mobilized SA-HRP in tumor cell lines. Using pairwise comparison of gene array results from 7 pairs of cell lines (each pair from a different anatomical site, as shown in Table 3), the functional distribution of differentially regulated genes is shown.

FIG. 7 shows up-regulated genes correlated to MBD-mobilized HRP internalization in tumor cell lines. The vast majority of up-regulated genes associated with greater uptake are associated with cellular stress responses.

FIG. 8 shows down-regulated genes correlated to MBD-mobilized HRP internalization in tumor cell lines. The vast majority of down-regulated genes are associated with secreted gene products.

FIG. 9 shows examples of specific genes that are up- or down-regulated in association with cell internalization of MBD-mobilized SA-HRP in tumor cell lines.

FIG. 10 shows surface markers cross-linked in association with cell internalization of MBD-mobilized SA-HRP in tumor cell lines. Membrane Markers: Cross-linking to biotinylated MBD21 peptide was performed on chilled cells as previously described (Singh B. et al op. cit.). Cell extracts were captured on Ni-NTA-coated 96-well plates, washed, blocked with 3% BSA and probed with the relevant antibody to the surface markers indicated. Intracellular Markers: Extracts were measured using standard ELISAs.

FIG. 13 shows some candidates cellular stress response programs.

FIG. 14 shows cell internalization of MBD-mobilized SA-HRP in five tumor cell lines and the effect of heatshock pre-treatment.

FIG. 15 shows cell internalization of MBD-mobilized SA-HRP in UO-31 cell line after thapsigargin pretreatment for the indicated times (endoplasmic reticulum (ER) stress). Cellular fractionation of extracts from each time point reveal differences in partitioning at different times between nuclear and non-nuclear intracellular location of the MBD-mobilized proteins.

FIG. 16 shows biodistribution of MBD-tagged proteins systemically administered to rats in vivo. Male Lewis rats were sacrificed 2 hours after intravenous injection of the indicated tracer proteins at 1 mg/kg bolus. Tissues were analyzed for TK protein by ELISA.

FIG. 17 shows blood cell association of MBD-tagged proteins systemically administered in vivo in the same experiment described in FIG. 16. A strong MBD-specific association with red blood cells is observed.

FIG. 18 shows markers of disease progression in a rat adjuvant arthritis model.

FIG. 19 shows cell internalization of MBD-tagged GFP protein systemically administered in vivo as described in FIG. 16, but using the rat adjuvant arthritis model of FIG. 18. The effects of inflammatory stress (arthritis) on organ-specific uptake of MBD-mobilized GFP protein can be measured in this experiment.

FIG. 20 shows cell internalization of MBD-tagged SA::HRP protein systemically administered in vivo in the same inflammatory stress (arthritis) model of FIG. 19.

FIG. 21 shows stress-related cell internalization of MBD-tagged HRP protein by HEK293 cells.

FIG. 22 shows stress-related cell internalization of MBD-tagged HRP protein by PC-12 cells.

FIG. 23. All peptides showed significantly different effects from control on cells except for peptides 5 and 6 on Hst578T and MDA-MB435 cells.

FIG. 24. Peptides added to cells: 1: PEP-1; 2: PEP-2; 3: PEP-3; 4: PKCI; 5: CSK; 6: VIVIT; 7: NFKB; 8: CTLA4; 9: CD28; 10: NEMO; 11: MAN.

FIG. 25. Synergy with nutritional stress on MCF-7 breast cancer cells. PEP-3 was added at 25 ug/ml.

FIG. 26. Synergy with chemotherapeutic agents in MCF-7 breast cancer cells. Peptides were added at 25 ug/ml. Tamoxifen (1 mM; TAM) or paclitaxel (0.1 ug/ml; TAX) were added simultaneously.

FIG. 27A—Right graph. CCRF-CEM injection induces severe splenomegaly and death in Rag-2 mice at 21 days post injection. Three human leukemia lines induced splenomegaly in Rag-2 mice in proportion to cellular growth rates. CCRF-CEM is the fastest growing line and induces severe splenomegaly within three weeks.

FIG. 28. MBD-mediated antibody uptake. MBD-mediated cellular uptake of several proteins has been previously demonstrated. In this experiment, uptake of a monoclonal antibody into MCF7 cancer cells is efficiently driven by an MBD peptide (PEP3). A complex of streptavidin+anti-streptavidin monoclonal antibody was incubated for 10 minutes with either no peptide (left) or PEP3 (right). After washing of cells and trypsinization, cell extracts were fractionated as described above. Cytoplasmic and nuclear extracts were assayed for antibody using a rabbit anti-mouse secondary antibody conjugated to alkaline phosphatase.

FIG. 29. MBD-tagged horseradish peroxidase (HRP) is preferentially taken up by cancer cells. ATCC paired cell lines (normal, cancer) were compared for levels of MBD-mediated uptake of HRP. Uptake assays were performed as described above.

FIG. 30. Combinatorial power of therapeutic enhancers. TOP PANEL: Traditional chemotherapeutic regimens target proliferative mechanisms and therefore (a) cause side effects which are dose-limiting because of their action on the body's normal fast-growing cells (b) fail to kill cancer cells that grow slowly, and (c) are therefore dose-limited in their combinatorial power. CENTER PANEL: Tumor heterogeneity makes it highly likely that small numbers of tumor cells will survive the original treatment and that disease will recur. BOTTOM PANEL: Biological agents enhance the effect of low-dose chemotherapeutic regimens by selectively sensitizing cancer cells (based on inhibiting stress-coping mechanisms frequently deranged in cancer) and increasing the combinatorial power dramatically, making it more likely that the spectrum of activity of a chemotherapeutic regimen might be broadened.

FIG. 31. Configurations of peptide enhancers. Representative peptide sequences known to inhibit survival and growth mechanisms that are typically deranged in cancer are shown on the left. Possible structural configurations combining MBD with one or more such inhibitor peptide sequences are shown on the right (SEQ ID NOS: 180, 181, 182, 183, 184, 185, 186, and 187).

FIG. 32. Broad spectrum of intrinsic activity of peptide enhancers. Cytotoxicity of MBD-tagged peptides was tested on prostate cancer, breast cancer and leukemia cell lines.

FIG. 33. Enhancer effects are proportional to MBD-mediated uptake. The cytotoxicity of peptide enhancers on 6 breast cancer lines was tested, with or without added 5-fluorouracil (0.25 ng/ml). Results are plotted against the uptake of MBD-tagged HRP in each line.

FIG. 34. Broad spectrum of enhancement in breast cancer. Data is shown for enhancer effects on the sensitivity of 8 breast cancer cell lines to paclitaxel (taxol).

FIG. 35. Selective toxicity of enhancers to cancer cells. ATCC paired cell lines (normal, cancer) were compared for combined effects of either Taxol or 5-FU with peptide enhancers.

FIG. 36. Additive effects of curcumin, lycopene and peptide enhancers. LEFT: Additive effects of peptide enhancers and curcumin::lycopene mix (2:1). RIGHT: Additive effects of curcumin::lycopene (2:1) mixture on MDA-MB-231 cells.

FIG. 37. Effectiveness in CCRF-CEM Rag-2 mouse model of leukemia. TOP PANEL: Survival of mice intracardially implanted with $3\times10^6$ CCRF-CEM leukemia cells on Day 1 and treated (from Day 7) as indicated. BOTTOM PANEL: Average spleen size in the same treatment groups. Average n for groups was 8 animals.

FIG. 38. Effectiveness in MDA-MB-435 and MDA-MB-231 models of disseminated breast cancer. LEFT PANEL: MDA-MB-435 burden in bone marrow of animals treated with saline or peptide enhancer. RIGHT PANEL: Results of a similar experiment performed with MDA-MB-231, wherein treated animal received a mixture of peptide enhancer (intravenous bolus injection) and dietary curcumin/lycopene daily.

MODES FOR CARRYING OUT THE INVENTION

Methods of Identifying Candidates for Treatment

Figure 1A:
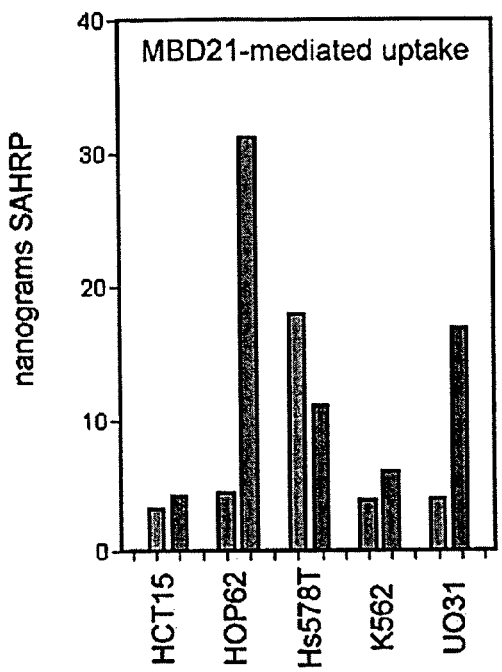
FIGS. 1A, 1B and 1C summarize the results of the experiment described in Example 3.

The invention provides methods for identifying candidates for treatment with MBD peptide-based therapies.

Candidates for treatment with MBD peptide-based therapies are individuals (a) for whom MBD peptide-based therapy has been proposed (such as individuals who have been diagnosed with a disorder treatable with an MBD peptide-based therapy) and whose relevant tissue is predicted to have relatively high uptake of MBD peptide(s).

MBD peptide based therapy has been previously disclosed for a number of different indications, including cancer (such as breast, prostate, colon, ovarian, pancreatic, gastric and lung cancer), autoimmune disease, cardiovascular indications, arthritis, asthma, allergy, reproductive indications, retinal proliferative disease, bone disease, inflammatory disease, inflammatory bowel disease, and fibrotic disease. MBD peptides and therapies based thereon are further described in U.S. patent application publication nos. 2003/0059430, 2003/0161829, and 2003/0224990.

The inventor has discovered a number of different genes which are differentially regulated between cells that have low uptake of MBD peptides and those that have high uptake of MBD peptides. These genes, referred to herein as "MBD uptake indicator genes", include GDF15, SRC, ATF3, HSPF3, FAPP2, PSMB9, PSMB10, c-JUN, JUN-B, HSPA1A, HSPA6, NFKB2, IRF1, WDR9A, MAZ, NSG-X, KIAA1856, BRF2, COL9A3, TPD52, TAX40, PTPN3, CREM, HCA58, TCFL5, CEBPB, IL6R, ABCP2, CTGF, LAMA4, LAMB3, IL6, IL1B, UPA, MMP2, LOX, SPARC, FBN1, LUM, PAI1, TGFB2, URB, TSP1, CSPG2, DCN, ITGA5, TKT, CAV1, CAV2, COL1A1, COL4A1, COL4A2, COL5A1, COL5A2, COL6A2, COL6A3, COL7A1, COL8A1, and IL7R. Of these genes, GDF15, SRC, ATF3, HSPF3, FAPP2, PSMB9, PSMB10, c-JUN, JUN-B, HSPA1A, HSPA6, NFKB2, IRF1, WDR9A, MAZ, NSG-X, KIAA1856, BRF2, COL9A3, TPD52, TAX40, PTPN3, CREM, HCA58, TCFL5, CEBPB, IL6R and ABCP2 are up-regulated in cells which have high uptake of MBD peptides. It should be noted that at least one third of these up-regulated genes have been previously associated with cellular responses to stress (e.g. GDF15, ATF3, HSPF3, PSMB9, PSMB10, c-JUN, JUN-B, HSPA1A, HSPA6, NFKB2, IRF1). Down-regulated genes include CTGF, LAMA4, LAMB3, IL6, IL1B, UPA, MMP2, LOX, SPARC, FBN1, LUM, PAI1, TGFB2, URB, TSP1, CSPG2, DCN, ITGA5, TKT, CAV1, CAV2, COL1A1, COL4A1, COL4A2, COL5A1, COL5A2, COL6A2, COL6A3, COL7A1, COL8A1, and IL7R. The inventor further notes that specific formulae for identifying candidates for MBD peptide therapy may be developed using the data and techniques described herein.

Accordingly, the invention provides methods of identifying candidates for MBD peptide-based therapy by obtaining a measured level for at least one MBD uptake indicator gene in a tissue sample from an individual and comparing that measured level with a reference level. For up-regulated genes, a comparison that indicates that the measured level is higher than the reference level identifies a candidate for MBD peptide-based therapy. Likewise, a comparison that indicates that the measured level is lower than a reference level for a down-regulated MBD uptake indicator gene is lower than the reference level identifies a candidate for MBD peptide-based therapy.

Levels of the particular genes which are differentially regulated may be measured using any technology known in the art. Generally, mRNA is extracted from a sample of the relevant tissue (e.g., where the individual has been diagnosed with cancer, a biopsy sample of the tumor will generally be the sample tested). Direct quantitation methods (methods which measure the level of transcripts from a particular gene without conversion of the RNA into DNA or any amplification) may be used, but it is believed that measurement will be more commonly performed using technology which utilizes an amplification step (thereby reducing the minimum size sample necessary for testing).

Amplification methods generally involve a preliminary step of conversion of the mRNA into cDNA by extension of a primer (commonly one including an oligo-dT portion) hybridized to the mRNA in the sample with a RNA-dependent DNA polymerase. Additionally, a second cDNA strand (complementary to the first synthesized strand) may be synthesized when desired or necessary. Second strand cDNA is normally synthesized by extension of a primer hybridized to the first cDNA strand using a DNA-dependent DNA polymerase. The primer for second strand synthesis may be a primer that is added to the reaction (such as random hexamers) or may be 'endogenous' to the reaction (i.e., provided by the original RNA template, such as by cleavage with an enzyme or agent that cleaves RNA in a RNA/DNA hybrid, such as RNase H).

Amplification may be carried out separately from quantitation (e.g., amplification by single primer isothermal amplification, followed by quantitation of the amplification product by probe hybridization), or may be part of the quantitation process, such as in real time PCR.

Measured levels may be obtained by the practitioner of the instant invention, or may be obtained by a third party (e.g., a clinical testing laboratory) who supplies the measured value(s) to the practitioner.

Reference levels are generally obtained from "normal" tissues. Normal tissues are those which are not afflicted with the particular disease or disorder which is the subject of the MBD peptide-based therapy. For example, when the disease to be treated with MBD peptide-based therapy is ductal breast carcinoma, the reference value is normally obtained from normal breast duct tissue. Likewise, for cardiovascular disorders, the "normal" tissue might be normal arterial wall tissue (e.g., when the disorder is atherosclerosis). Alternately, values from cells (which may be tissue culture cells or cell lines) which have low MBD peptide uptake may also be used to derive a reference value.

The process of comparing a measured value and a reference value can be carried out in any convenient manner appropriate to the type of measured value and reference value for the MBD uptake indicator gene at issue. It should be noted that the measured values obtained for the MBD uptake indicator gene(s) can be quantitative or qualitative measurement techniques, thus the mode of comparing a measured value and a reference value can vary depending on the measurement technology employed. For example, when a qualitative calorimetric assay is used to measure MBD uptake indicator gene levels, the levels may be compared by visually comparing the intensity of the colored reaction product, or by comparing data from densitometric or spectrometric measurements of the colored reaction product (e.g., comparing numerical data or graphical data, such as bar charts, derived from the measuring device). Quantitative values (e.g., transcripts/cell or transcripts/unit of RNA, or even arbitrary units) may also be used. As with qualitative measurements, the comparison can be made by inspecting the numerical data, by inspecting representations of the data (e.g., inspecting graphical representations such as bar or line graphs).

As will be understood by those of skill in the art, the mode of detection of the signal will depend on the exact detection system utilized in the assay. For example, if a radiolabeled detection reagent is utilized, the signal will be measured using a technology capable of quantitating the signal from the biological sample or of comparing the signal from the biological sample with the signal from a reference sample, such as scintillation counting, autoradiography (typically combined with scanning densitometry), and the like. If a chemiluminescent detection system is used, then the signal will typically be detected using a luminometer. Methods for detecting signal from detection systems are well known in the art and need not be further described here.

When more than one MBD uptake indicator gene is measured (i.e., measured values for two or more MBD uptake indicator genes are obtained), the sample may be divided into a number of aliquots, with separate aliquots used to measure different MBD uptake indicator gene (although division of the biological sample into multiple aliquots to allow multiple determinations of the levels of the MBD uptake indicator gene(s) in a particular sample are also contemplated). Alternately the sample (or an aliquot therefrom) may be tested to determine the levels of multiple MBD uptake indicator genes in a single reaction using an assay capable of measuring the individual levels of different MBD uptake indicator genes in a single assay, such as an array-type assay or assay utilizing multiplexed detection technology (e.g., an assay utilizing detection reagents labeled with different fluorescent dye markers).

As will be understood by those in the art, the exact identity of a reference value will depend on the tissue that is the target of treatment and the particular measuring technology used. In some embodiments, the comparison determines whether the measured value for the MBD uptake indicator gene is above or below the reference value. In some embodiments, the comparison is performed by finding the "fold difference" between the reference value and the measured value (i.e., dividing the measured value by the reference value). Table 1 lists certain exemplary fold differences for use in the instant invention.

TABLE 1

| GENE | Prostate | Colon | Lung | Kidney | Breast |
|---|---|---|---|---|---|
| GDF-15 | 50 | 4 | 7 | 8 | 1.4 |
| IRF1 | 3 | 3 | 1.05 | 1.6 | 1.15 |
| HSP1A1 | 1.7 | 1.15 | 2.4 | 2.8 | 5 |
| JUNB | 5 | 0.95 | 3 | 1.6 | 5 |
| TGFB2 | 0.6 | 0.92 | 0.5 | 0.85 | 0.5 |
| IL6 | 1.05 | 0.85 | 0.6 | 0.6 | 0.5 |
| SPARC | 5 | 0.85 | 0.5 | 0.6 | |

Candidates suitable for treatment with MBD peptide-based therapies are identified when at least a simple majority of the comparisons between the measured values and the reference values indicate that the cells in the sample (and thus the diseased cells in the individual) have relatively high uptake of MBD peptides. For up-regulated MBD uptake indicator genes (GDF15, SRC, ATF3, HSPF3, FAPP2, PSMB9, PSMB10, c-JUN, JUN-B, HSPA1A, HSPA6, NFKB2, IRF1, WDR9A, MAZ, NSG-X, KIAA1856, BRF2, COL9A3, TPD52, TAX40, PTPN3, CREM, HCA58, TCFL5, CEBPB, IL6R and ABCP2), a measured value that is greater than the reference value (which may be a simple "above or below" comparison or a comparison to find a minimum fold difference) indicates that the cells in the sample have relatively high uptake of MBD peptides. For down-regulated MBD uptake indicator genes (CTGF, LAMA4, LAMB3, IL6, IL1B, UPA, MMP2, LOX, SPARC, FBN1, LUM, PAI1, TGFB2, URB, TSP1, CSPG2, DCN, ITGA5, TKT, CAV1, CAV2, COL1A1, COL4A1, COL4A2, COL5A1, COL5A2, COL6A2, COL6A3, COL7A1, COL8A1, and IL7R), a measured value that is less than the reference value (which may be a simple "above or below" comparison or a comparison to find a minimum fold difference) indicates that the cells in the sample have relatively high uptake of MBD peptides.

Additionally, because certain of the MBD uptake indicator genes are found in serum (e.g. HSP70, GFP15), the invention also provides methods of identifying candidates for MBD peptide-based therapy by obtaining a measured level for at least one MBD uptake indicator gene in a biological fluid sample from an individual and comparing that measured level with a reference level. For up-regulated genes, a comparison that indicates that the measured level is higher than the reference level identifies a candidate for MBD peptide-based therapy. Likewise, a comparison that indicates that the measured level is lower than a reference level for a down-regulated MBD uptake indicator gene is lower than the reference level identifies a candidate for MBD peptide-based therapy.

A measured level is obtained for the relevant tissue for at least one MBD uptake indicator protein (i.e., the protein encoded by an MBD uptake marker gene), although multiple MBP uptake indicator proteins may be measured in the practice of the invention. Generally, it is preferred that measured levels are obtained for more than one MBD uptake indicator protein. Accordingly, the invention may be practiced using at least one, at least two, at least three, at least four, at least five, at least six, at least seven, at least eight, at least nine, at least ten, or more than ten MBD uptake indicator proteins. In certain embodiments, at least one of the measured values is obtained for a MBD uptake indicator protein that is up-regulated in cells which have high MBD peptide uptake levels and at least one of the measured values is obtained for a MBD uptake indicator protein that is down-regulated in cells which have high MBD peptide uptake levels. As will be apparent to those of skill in the art, the MBD uptake indicator proteins for which measured values are obtained are most commonly MBD uptake indicator proteins which may be secreted (e.g., HSP70, GDF15).

The MBD uptake indicator protein(s) may be measured using any available measurement technology that is capable of specifically determining the level of the MBD uptake indicator protein in a biological sample. In certain embodiments, the measurement may be either quantitative or qualitative, so long as the measurement is capable of indicating whether the level of the MBD uptake indicator protein in the biological sample is above or below the reference value.

Although some assay formats will allow testing of biological samples without prior processing of the sample, it is expected that most biological samples will be processed prior to testing. Processing generally takes the form of elimination of cells (nucleated and non-nucleated), such as erythrocytes, leukocytes, and platelets in blood samples, and may also include the elimination of certain proteins, such as certain clotting cascade proteins from blood.

Commonly, MBD uptake indicator protein levels will be measured using an affinity-based measurement technology. Affinity-based measurement technology utilizes a molecule that specifically binds to the MBD uptake indicator protein being measured (an "affinity reagent," such as an antibody or aptamer), although other technologies, such as spectroscopy-based technologies (e.g., matrix-assisted laser desorption ionization-time of flight, or MALDI-TOF, spectroscopy) or assays measuring bioactivity (e.g., assays measuring mitogenicity of growth factors) may be used.

Affinity-based technologies include antibody-based assays (immunoassays) and assays utilizing aptamers (nucleic acid molecules which specifically bind to other molecules), such as ELONA. Additionally, assays utilizing both antibodies and aptamers are also contemplated (e.g., a sandwich format assay utilizing an antibody for capture and an aptamer for detection).

If immunoassay technology is employed, any immunoassay technology which can quantitatively or qualitatively measure the level of a MBD uptake indicator protein in a biological sample may be used. Suitable immunoassay technology includes radioimmunoassay, immunofluorescent assay, enzyme immunoassay, chemiluminescent assay, ELISA, immuno-PCR, and western blot assay.

Likewise, aptamer-based assays which can quantitatively or qualitatively measure the level of a MBD uptake indicator protein in a biological sample may be used in the methods of the invention. Generally, aptamers may be substituted for antibodies in nearly all formats of immunoassay, although aptamers allow additional assay formats (such as amplification of bound aptamers using nucleic acid amplification technology such as PCR (U.S. Pat. No. 4,683,202) or isothermal amplification with composite primers (U.S. Pat. Nos. 6,251,639 and 6,692,918).

A wide variety of affinity-based assays are known in the art. Affinity-based assays will utilize at least one epitope derived from the MBD uptake indicator protein of interest, and many affinity-based assay formats utilize more than one epitope (e.g., two or more epitopes are involved in "sandwich" format assays; at least one epitope is used to capture the marker, and at least one different epitope is used to detect the marker).

Affinity-based assays may be in competition or direct reaction formats, utilize sandwich-type formats, and may further be heterogeneous (e.g., utilize solid supports) or homogenous (e.g., take place in a single phase) and/or utilize or immunoprecipitation. Most assays involve the use of labeled affinity reagent (e.g., antibody, polypeptide, or aptamer); the labels may be, for example, enzymatic, fluorescent, chemiluminescent, radioactive, or dye molecules. Assays which amplify the signals from the probe are also known; examples of which are assays which utilize biotin and avidin, and enzyme-labeled and mediated immunoassays, such as ELISA and ELONA assays.

In a heterogeneous format, the assay utilizes two phases (typically aqueous liquid and solid). Typically a MBD uptake indicator protein-specific affinity reagent is bound to a solid support to facilitate separation of the MBD uptake indicator protein from the bulk of the biological sample. After reaction for a time sufficient to allow for formation of affinity reagent/MBD uptake indicator protein complexes, the solid support containing the antibody is typically washed prior to detection of bound polypeptides. The affinity reagent in the assay for measurement of MBD uptake indicator proteins may be provided on a support (e.g., solid or semi-solid); alternatively, the polypeptides in the sample can be immobilized on a support. Examples of supports that can be used are nitrocellulose (e.g., in membrane or microtiter well form), polyvinyl chloride (e.g., in sheets or microtiter wells), polystyrene latex (e.g., in beads or microtiter plates), polyvinylidine fluoride, diazotized paper, nylon membranes, activated beads, and Protein A beads. Both standard and competitive formats for these assays are known in the art.

Array-type heterogeneous assays are suitable for measuring levels of MBD uptake indicator proteins when the methods of the invention are practiced utilizing multiple MBD uptake indicator proteins. Array-type assays used in the practice of the methods of the invention will commonly utilize a solid substrate with two or more capture reagents specific for different MBD uptake indicator proteins bound to the substrate a predetermined pattern (e.g., a grid). The biological sample is applied to the substrate and MBD uptake indicator proteins in the sample are bound by the capture reagents. After removal of the sample (and appropriate washing), the bound MBD uptake indicator proteins are detected using a mixture of appropriate detection reagents that specifically bind the various MBD uptake indicator proteins. Binding of the detection reagent is commonly accomplished using a visual system, such as a fluorescent dye-based system. Because the capture reagents are arranged on the substrate in a predetermined pattern, array-type assays provide the advantage of detection of multiple MBD uptake indicator proteins without the need for a multiplexed detection system.

In a homogeneous format the assay takes place in single phase (e.g., aqueous liquid phase). Typically, the biological sample is incubated with an affinity reagent specific for the MBD uptake indicator protein in solution. For example, it may be under conditions that will precipitate any affinity reagent/antibody complexes which are formed. Both standard and competitive formats for these assays are known in the art.

In a standard (direct reaction) format, the level of MBD uptake indicator protein/affinity reagent complex is directly monitored. This may be accomplished by, for example, determining the amount of a labeled detection reagent that forms is bound to MBD uptake indicator protein/affinity reagent complexes. In a competitive format, the amount of MBD uptake indicator protein in the sample is deduced by monitoring the competitive effect on the binding of a known amount of labeled MBD uptake indicator protein (or other competing ligand) in the complex. Amounts of binding or complex formation can be determined either qualitatively or quantitatively.

Complexes formed comprising MBD uptake indicator protein and an affinity reagent are detected by any of a number of known techniques known in the art, depending on the format of the assay and the preference of the user. For example, unlabelled affinity reagents may be detected with DNA amplification technology (e.g., for aptamers and DNA-labeled antibodies) or labeled "secondary" antibodies which bind the affinity reagent. Alternately, the affinity reagent may be labeled, and the amount of complex may be determined directly (as for dye-(fluorescent or visible), bead-, or enzyme-labeled affinity reagent) or indirectly (as for affinity reagents "tagged" with biotin, expression tags, and the like).

As will be understood by those of skill in the art, the mode of detection of the signal will depend on the exact detection system utilized in the assay. For example, if a radiolabeled detection reagent is utilized, the signal will be measured using a technology capable of quantitating the signal from the biological sample or of comparing the signal from the biological sample with the signal from a reference sample, such as scintillation counting, autoradiography (typically combined with scanning densitometry), and the like. If a chemiluminescent detection system is used, then the signal will typically be detected using a luminometer. Methods for detecting signal from detection systems are well known in the art and need not be further described here.

When more than one MBD uptake indicator protein is measured, the biological sample may be divided into a number of aliquots, with separate aliquots used to measure different MBD uptake indicator proteins (although division of the biological sample into multiple aliquots to allow multiple determinations of the levels of the MBD uptake indicator protein in a particular sample are also contemplated). Alternately the biological sample (or an aliquot therefrom) may be tested to determine the levels of multiple MBD uptake indicator proteins in a single reaction using an assay capable of measuring the individual levels of different MBD uptake indicator proteins in a single assay, such as an array-type assay or assay utilizing multiplexed detection technology (e.g., an assay utilizing detection reagents labeled with different fluorescent dye markers).

It is common in the art to perform 'replicate' measurements when measuring MBD uptake indicator proteins. Replicate measurements are ordinarily obtained by splitting a sample into multiple aliquots, and separately measuring the MBD uptake indicator protein (s) in separate reactions of the same assay system. Replicate measurements are not necessary to the methods of the invention, but many embodiments of the invention will utilize replicate testing, particularly duplicate and triplicate testing.

Kits for Identification of Candidates for MBD Peptide Therapy

The invention provides kits for carrying out the methods of the invention. Kits of the invention comprise at least one probe specific for a MBD uptake indicator gene (and/or at least one affinity reagent specific for a MBD uptake indicator protein) and instructions for carrying out a method of the invention. More commonly, kits of the invention comprise at least two different MBD uptake indicator gene probes (or at least two affinity reagents specific for MBD uptake indicator proteins), where each probe/reagent is specific for a different MBD uptake indicator gene.

Kits comprising a single probe for a MBD uptake indicator gene (or affinity reagent specific for a MBD uptake indicator protein) will generally have the probe/reagent enclosed in a container (e.g., a vial, ampoule, or other suitable storage container), although kits including the probe/reagent bound to a substrate (e.g., an inner surface of an assay reaction vessel) are also contemplated. Likewise, kits including more than one probe/reagent may also have the probes/reagents in containers (separately or in a mixture) or may have the probes/affinity reagents bound to a substrate (e.g., such as an array or microarray).

A modified substrate or other system for capture of MBD uptake indicator gene transcripts or MBD uptake indicator proteins may also be included in the kits of the invention, particularly when the kit is designed for use in an array format assay.

In certain embodiments, kits according to the invention include the probes/reagents in the form of an array. The array includes at least two different probes/reagents specific for a MBD uptake indicator gene/protein (each probe/reagent specific for a different MBD uptake indicator gene/protein) bound to a substrate in a predetermined pattern (e.g., a grid). The localization of the different probes/reagents allows measurement of levels of a number of different MBD uptake indicator genes/proteins in the same reaction.

The instructions relating to the use of the kit for carrying out the invention generally describe how the contents of the kit are used to carry out the methods of the invention. Instructions may include information as sample requirements (e.g., form, pre-assay processing, and size), steps necessary to measure the MBD uptake indicator gene(s), and interpretation of results.

Instructions supplied in the kits of the invention are typically written instructions on a label or package insert (e.g., a paper sheet included in the kit), but machine-readable instructions (e.g., instructions carried on a magnetic or optical storage disk) are also acceptable. In certain embodiments, machine-readable instructions comprise software for a programmable digital computer for comparing the measured values obtained using the reagents included in the kit.

Therapeutic Methods

The therapeutic methods of the invention utilize treatment of certain disorders (e.g., disorders characterized by secreted HSP70 and macrophage co-localized at the site of disease) with MBD peptide therapies. The invention provides methods of treating diseases characterized by measurable cellular stress responses (such as the induction of heat shock proteins) including, but not limited to, metabolic and oxidative stress, with MBD peptide therapies. MBD peptide therapies include treatment by administration of (a) MBD peptides, (b) MBD peptide fusions, and (c) MBD peptide conjugates.

The invention provides methods for delivering an MBD peptide-linked agent into live cells, said method comprising contacting said MBD peptide-linked agent to live cells that are under a condition of cellular stress, whereby said contact results in cellular uptake of said MBD-peptide-linked agent.

The condition of cellular stress can be any type of stress, such as thermal, immunological, cytokine, oxidative, metabolic, anoxic, endoplasmic reticulum, protein unfolding, nutritional, chemical, mechanical, osmotic and glycemic stress. In some embodiments, the condition of cellular stress is associated with upregulation of at least one, at least two, at least three, at least four, at least five, at least ten, at least fifteen, at least twenty, or all of the genes shown in FIG. 7 as compared to the cells not under the condition of cellular stress. Accordingly, the methods of invention may further include a step of comparing levels of gene expression of any one or more of the genes shown in FIG. 7 in cells under a condition of cellular stress to levels of gene expression of the same gene or genes in the cells not under the condition of cellular stress, whereby cells that are candidate targets for delivering MBD peptide-linked agents are identified. The upregulation may be at least about 1.5-fold, at least about 2-fold, at least about 3-fold, at least about 5-fold, or at least about 10-fold.

"Metal-binding domain peptide" or "MBD peptide" means an IGFBP-derived peptide or polypeptide from about 12 to about 60 amino acids long, preferably from about 13 to 40 amino acids long, comprising a segment of the CD-74-homology domain sequence in the carboxy-terminal 60-amino acids of IGFBP-3, comprising the sequence CRPSKGRKRGFC (SEQ ID NO: 7) and exhibiting metal-binding properties, but differing from intact IGFBP-3 by exhibiting distinct antigenic properties, lacking IGF-I-binding properties, and lacking the mid-region sequences (amino acids 88-148 of IGFBP-3 sequence). For example, the peptide GFYKKKQCRPSKGRKRGFCW (SEQ ID NO: 8) is an example of a metal-binding domain peptide. It binds metal ions but not IGF-I, and polyclonal antibodies raised to this peptide do not substantially cross-react with intact IGFBP-3, and vice versa. In certain embodiments, the MBD peptide includes a caveolin consensus binding sequence (#x#xxxx#, where '#' is an aromatic amino acid) in addition to, or overlapping with, the MBD peptide sequence. The caveolin consensus sequence may be at the amino terminal or carboxy terminal end of the peptide. In certain preferred embodiments, the caveolin consensus binding sequence is at the carboxy terminal end of the peptide, and overlaps with the MBD core 14-mer sequence. Exemplary MBD peptides with caveolin consensus binding sequences include peptides comprising the sequence QCRPSKGRKRGFCWAVDKYG (SEQ ID NO: 3) or KKGFYKKKQCRPSKGRKRGFC-WAVDKYG (SEQ ID NO: 4).

MBD peptides may be modified, such as by making conservative substitutions for the natural amino acid residue at any position in the sequence, altering phosphorylation, acetylation, glycosylation or other chemical status found to occur at the corresponding sequence position of IGFBP-3 in the natural context, substituting D- for L-amino acids in the sequence, or modifying the chain backbone chemistry, such as protein-nucleic-acid (PNA).

"Conjugates" of an MBD peptide and a second molecule include both covalent and noncovalent conjugates between a MBD peptide and a second molecule (such as a transcriptional modulator or a therapeutic molecule). Noncovalent conjugates may be created by using a binding pair, such as biotin and avidin or streptavidin or an antibody (including Fab fragments, scFv, and other antibody fragments/modifications) and its cognate antigen.

Sequence "identity" and "homology", as referred to herein, can be determined using BLAST (Altschul, et al., 1990, J. Mol. Biol. 215(3):403-410), particularly BLASTP 2 as implemented by the National Center for Biotechnology Information (NCBI), using default parameters (e.g., Matrix 0 BLOSUM62, gap open and extension penalties of 11 and 1, respectively, gap x_dropoff 50 and wordsize 3). Unless referred to as "consecutive" amino acids, a sequence optionally can contain a reasonable number of gaps or insertions that improve alignment.

An effective amount of the MBD therapy is administered to a subject having the disease. In some embodiments, the MBD therapy is administered at about 0.001 to about 40 milligrams per kilogram total body weight per day (mg/kg/day). In some embodiments the MBD therapy is administered at about 0.001 to about 40 mg/kg/day of MBD peptide (i.e., the MBD peptide portion of the therapy administered is about 0.001 to about 40 mg/kg/day).

The terms "subject" and "individual", as used herein, refer to a vertebrate individual, including avian and mammalian individuals, and more particularly to sport animals (e.g., dogs, cats, and the like), agricultural animals (e.g., cows, horses, sheep, and the like), and primates (e.g., humans).

The term "treatment" is used herein as equivalent to the term "alleviating", which, as used herein, refers to an improvement, lessening, stabilization, or diminution of a symptom of a disease. "Alleviating" also includes slowing or halting progression of a symptom.

For the purposes of this invention, a "clinically useful outcome" refers to a therapeutic or diagnostic outcome that leads to amelioration of the disease condition. "Inflammatory disease condition" means a disease condition that is typically accompanied by chronic elevation of transcriptionally active NF-kappa-B or other known intermediates of the cellular inflammatory response in diseased cells. The following intracellular molecular targets are suggested as examples:

"NF-kappa-B regulator domain" includes a binding domain that participates in transport of NF-kappa-B into the nucleus [Strnad J, et al. J Mol Recognit. 19(3):227-33, 2006; Takada Y, Singh S, Aggarwal B B. J Biol Chem. 279(15): 15096-104, 2004) and domains that participate in upstream signal transduction events to this transport. "P53 regulator domain" is the P53/MDM2 binding pocket for the regulatory protein MDM2 (Michl J, et al, Int J Cancer. 119(7): 1577-85, 2006). "IGF-signalling regulator domain" refers to the SH domain of Dok-1 which participates critically in IGF receptor signal transduction (Clemmons D and Maile L. Mol Endocrinol. 19(1): 1-11, 2005). "RAS active site domain" refers to the catalytic domain of the cellular Ras enzyme. "MYC regulator domain" refers to the amino-terminal regulatory region of c-myc or to its DNA-binding domain, both of which have been well-characterized (Luscher B and Larson L G. Oncogene. 18(19):2955-66, 1999). "HSP regulator domain" includes trimerization inhibitors of HSF-1 (Tai L J et al. J Biol Chem. 277(1):735-45, 2002). "Survivin dimerization domain" refers to well-characterized sequences at the dimer interface of Survivin (Sun C, et al. Biochemistry. 44(1): 11-7, 2005). "Proteasome subunit regulator domain" refers to the target for hepatitis B virus-derived proteasome inhibitor which competes with PA28 for binding to the proteasome alpha4/MC6 subunit (Stohwasser R, et al. Biol Chem. 384(1): 39-49, 2003). "HIF1-alpha oxygen-dependent regulator domain" refers to the oxygen-dependent degradation domain within the HIF-1 protein (Lee J W, et al. Exp Mol Med. 36(1): 1-12, 2004).

As used herein, "in conjunction with", "concurrent", or "concurrently", as used interchangeably herein, refers to administration of one treatment modality in addition to another treatment modality. As such, "in conjunction with" refers to administration of one treatment modality before, during or after delivery of the other treatment modality to the subject.

The MBD peptide is normally produced by recombinant methods, which allow the production of all possible variants in peptide sequence. Techniques for the manipulation of recombinant DNA are well known in the art, as are techniques for recombinant production of proteins (see, for example, in Sambrook et al., MOLECULAR CLONING: A LABORATORY MANUAL, Vols. 1-3 (Cold Spring Harbor Laboratory Press, 2 ed., (1989); or F. Ausubel et al., CURRENT PROTOCOLS IN MOLECULAR BIOLOGY (Green Publishing and Wiley-Interscience: New York, 1987) and periodic updates). Derivative peptides or small molecules of known composition may also be produced by chemical synthesis using methods well known in the art.

Preferably, the MBD peptide is produced using a bacterial cell strain as the recombinant host cell. An expression construct (i.e., a DNA sequence comprising a sequence encoding the desired MBD peptide operably linked to the necessary DNA sequences for proper expression in the host cell, such as a promoter and/or enhancer elements at the 5' end of the construct and terminator elements in the 3' end of the construct) is introduced into the host cell. The DNA sequence encoding the MBD peptide may optionally linked to a sequence coding another protein (a "fusion partner"), to form a fusion protein. Preferably, the DNA sequence encoding the MBD peptide is linked to a sequence encoding a fusion partner as described in U.S. Pat. No. 5,914,254. The expression construct may be an extrachromosomal construct, such as a plasmid or cosmid, or it may be integrated into the chromosome of the host cell, for example as described in U.S. Pat. No. 5,861,273.

Accordingly, the invention provides methods of treatment with fusions and/or conjugates of MBD peptides with molecules (such as agents) which are desired to be internalized into cells. The fusion partner molecules may be polypeptides, nucleic acids, or small molecules which are not normally internalized (e.g., because of large size, hydrophilicity, etc.). The fusion partner can also be an antibody or a fragment of an antibody. As will be apparent to one of skill in the art, such fusions/conjugates will be useful in a number of different areas, including pharmaceuticals (to promote internalization of therapeutic molecules which do not normally become internalized), gene therapy (to promote internalization of gene therapy constructs), and research (allowing 'marking' of cells with an internalized marker protein). Preferred MBD peptides are peptides comprising the sequence KKG-FYKKKQCRPSKGRKRGFCW (SEQ ID NO: 9) or a sequence having at least 80, 85, 90, 95, 98, or 99% homology to said sequence. Fusions of MBD peptides and polypeptides are preferably made by creation of a DNA construct encoding the fusion protein, but such fusions may also be made by chemical ligation of the MBD peptide and the polypeptide of interest. Conjugates of MBD peptides and nucleic acids or small molecules can be made using chemical crosslinking technology known in the art. Preferably, the conjugate is produced using a heterobifunctional crosslinker to avoid production of multimers of the MBD peptide.

Therapy in accordance with the invention may utilize MBD peptides and transcriptional modulators (e.g., transcription factors). For example, T-bet (Szabo et al., 2000, *Cell* 100(6):655-69), a transcription factor that appears to commit T lymphocytes to the $T_{h1}$ lineage, can be fused to a MBD peptide to create a molecule a useful therapeutic. Likewise, therapy in accordance with the invention using conjugates of MBD peptides and therapeutic molecules is also provided. MBD peptides may be conjugated with any therapeutic molecule which is desired to be delivered to the interior of a cell, including antisense oligonucleotides and polynucleotide constructs (e.g., encoding therapeutic molecules such as growth factors and the like).

Peptides comprising an MBD peptide which includes a caveolin consensus binding sequence (MBD/caveolin peptides) may also be incorporated into conjugates. MBD/caveolin peptides may be conjugated with any therapeutic molecule that is desired to be delivered to the interior of a cell, including antisense oligonucleotides and polynucleotide constructs (e.g., encoding therapeutic molecules such as growth factors and the like).

Molecules comprising an MBD peptide are preferably administered via oral or parenteral administration, including but not limited to intravenous (IV), intra-arterial (IA), intraperitoneal (IP), intramuscular (IM), intracardial, subcutaneous (SC), intrathoracic, intraspinal, intradermal (ID), transdermal, oral, sublingual, inhaled, and intranasal routes. IV, IP, IM, and ID administration may be by bolus or infusion administration. For SC administration, administration may be by bolus, infusion, or by implantable device, such as an implantable minipump (e.g., osmotic or mechanical minipump) or slow release implant. The MBD peptide may also be delivered in a slow release formulation adapted for IV, IP, IM, ID or SC administration. Inhaled MBD peptide is preferably delivered in discrete doses (e.g., via a metered dose inhaler adapted for protein delivery). Administration of a molecule comprising a MBD peptide via the transdermal route may be continuous or pulsatile. Administration of MBD peptides may also occur orally.

For parenteral administration, compositions comprising a MBD peptide may be in dry powder, semi-solid or liquid formulations. For parenteral administration by routes other than inhalation, the composition comprising a MBD peptide is preferably administered in a liquid formulation. Compositions comprising a MBD peptide formulation may contain additional components such as salts, buffers, bulking agents, osmolytes, antioxidants, detergents, surfactants, and other pharmaceutical excipients as are known in the art.

A composition comprising a MBD peptide is administered to subjects at a dose of about 0.001 to about 40 mg/kg/day, more preferably about 0.01 to about 10 mg/kg/day, more preferably 0.05 to about 4 mg/kg/day, even more preferably about 0.1 to about 1 mg/kg/day.

As will be understood by those of skill in the art, the symptoms of disease alleviated by the instant methods, as well as the methods used to measure the symptom(s) will vary, depending on the particular disease and the individual patient.

Patients treated in accordance with the methods of the instant invention may experience alleviation of any of the symptoms of their disease.

EXAMPLES

Example 1

HEK293 kidney cell line and 54 tumor cell lines obtained from the National Cancer Institute and passaged in RPMI1640 cell culture medium supplemented with 10% fetal bovine serum and 10 uM $FeCl_2$. Uptake of streptavidin-horseradish peroxidase (SA-HRP) conjugate and of various SA-HRP::MBD peptide complexes was determined as described (Singh et al. J Biol Chem. 279 (1):477-87 [2004]) using biotinylated MBD9 (KKG-FYKKKKQCRPSKGRKRGFCWNGRK) (SEQ ID NO: 10) and MBD21 (KKGFYKKKQCRPSKGRKRGFCWAVD-KYG) (SEQ ID NO: 4) peptides and SA-HRP. Nuclear and cytoplasmic localization of these proteins was also determined in each case. The results of this survey are summarized in Table 2. They show that the rate of MBD-mediated uptake is highly variable across cell lines. In order to establish the underlying molecular mechanism for this variability, we cross-linked MBD21 peptide to the following cell surface markers at 4 degrees Celsius as previously described (Singh et al. J Biol Chem. 279 (1):477-87 [2004]): transferrin receptor 1, caveolin 1, PCNA, integrins alpha v, 2, 5 and 6, integrins beta 1, 3 and 5. Significant correlations (positive or negative) between crosslinking rates and the previously measured rates of MBD-mediated SA-HRP uptake were observed in the case of transferrin receptor 1, caveolin 1, integrins beta 3, beta 5 and alpha v. Based on the strength of these correlations, it was possible to derive crude predictive formulae for MBD-mediated uptake based on the rate of cross-linking to surface markers. Such predictive formulas could form the basis for a diagnostic procedure to select appropriate targets for MBD-based therapies.

TABLE 2

| Cell Line | Histologic Type | MBD9 Cyt. (ng) | MBD9 Nuc. (ng) | MBD21 Cyt. (ng) | MBD21 Nuc. (ng) |
|---|---|---|---|---|---|
| SK-0V-3 | hu Ascites Adenocarcinoma | 2.0 | 0.4 | <0.04 | <0.04 |
| OVCAR-3 | hu Ascites Adenocarcinoma | 2.4 | 4.6 | <0.04 | 3.2 |
| HOP 92 | hu Lung Large Cell, Undifferentiated | 2.5 | 1.6 | 1.5 | 1.6 |
| NCI-H226 | hu Lung Sqamous Cell | 2.6 | 1.8 | 0.7 | 0.9 |
| K562 | Lymph Leukemia | 2.6 | 1.3 | 2.8 | 1.1 |
| CCRF-SB | Lymph Leukemia | 2.6 | 0.6 | 1.7 | 0.1 |
| OVCAR-5 | hu Adenocarcinoma | 2.7 | 1.2 | 1.3 | 1.5 |
| 786-O | hu Renal Adenocarcinoma | 2.9 | 3.9 | 1.8 | 4.8 |
| COLO 205 | hu Ascitic Fluid Adenocarcinoma | 2.9 | 0.9 | 2.1 | 0.9 |
| DU-145 | hu Prostate Carcinoma | 3.1 | <0.04 | 25.7 | 3.3 |
| SW-620 | hu Colon Adenocarcinoma | 3.2 | 0.7 | 6.3 | 2.3 |
| WIDR | hu Colon Adenocarcinoma | 3.4 | 0.7 | 2.8 | 1.0 |
| HS 913T | hu Lung Mixed Cell | 3.4 | 1.1 | 2.1 | 1.8 |
| KM12 | hu Adenocarcinoma | 3.6 | 1.0 | 2.1 | 0.7 |
| OVCAR-8 | hu Adenocarcinoma | 3.9 | 5.0 | 6.1 | 13.1 |
| HCT-15 | hu Colon Adenocarcinoma | 4.0 | 0.8 | 2.7 | 0.7 |
| TK-10 | hu Renal Carcinoma | 4.0 | 1.3 | 5.0 | 2.2 |
| UO-31 | hu Renal Carcinoma | 4.6 | 1.0 | 1.3 | 3.3 |
| HCC 2998 | hu Adenocarcinoma | 4.6 | 3.7 | 2.1 | 2.4 |
| NHI-H322M | hu Lung Bronchi Alveolar Carcinoma | 5.2 | 5.0 | 6.0 | 8.3 |
| HT-29 | hu Recto-Sigmoid Colon Adenocarcinoma | 6.1 | 7.7 | 3.5 | 9.5 |
| RPMI 8226 | Lymph Leukemia | 6.5 | 0.0 | 3.6 | 0.0 |
| HS-578T | hu Ductal Carcinoma | 6.8 | 2.3 | 2.8 | 2.3 |
| IGR-OV1 | hu R Ovary Cysto Adenocarcinoma | 7.0 | 2.6 | 1.9 | 1.0 |
| BT-549 | hu Lymph Node Infil. Ductal Carcinoma | 7.2 | 2.1 | 4.8 | 3.3 |
| EKVX | hu Lung Adenocarcinoma | 7.2 | 4.2 | 7.7 | 7.3 |
| CAKI-1 | hu Renal Adenocarcinoma | 7.4 | 1.8 | 2.8 | 1.0 |

TABLE 2-continued

| Cell Line | Histologic Type | MBD9 Cyt. (ng) | MBD9 Nuc. (ng) | MBD21 Cyt. (ng) | MBD21 Nuc. (ng) |
|---|---|---|---|---|---|
| Lewis Lung | hu Lung Carcinoma | 8.6 | 7.2 | 6.4 | 3.4 |
| 435 | Breast adenocarcinoma | 8.6 | 2.7 | 6.1 | 1.3 |
| NCI-H522 | hu Lung Adnocarcinoma | 9.1 | 3.7 | 5.1 | 1.7 |
| A549 | hu Lung Adenocarcinoma | 9.6 | 3.5 | 4.4 | 1.3 |
| ACHN | hu Renal Carcinoma | 9.6 | 2.9 | 8.0 | 3.1 |
| 231 | Breast adenocarcinoma | 9.6 | 2.6 | 3.4 | 1.1 |
| OVCAR-4 | hu Adenocarcinoma | 9.9 | 2.7 | 6.1 | 1.3 |
| SN12C | hu Renal Carcinoma | 10.6 | 3.5 | 6.7 | 6.4 |
| NCI-H23 | hu Lung Adenocarcinoma | 10.8 | 6.6 | 8.0 | 8.7 |
| MX-1 | hu Breast Mammary Carcinoma | 10.8 | 3.1 | 8.5 | 3.8 |
| A704 | hu Renal Adenocarcinoma | 10.9 | 1.8 | 4.5 | 1.2 |
| COLON 26 | Carcinoma | 11.3 | 2.3 | 8.9 | 2.2 |
| HOP 62 | hu Lung Adenocarcinoma | 12.0 | 0.9 | 4.1 | 0.2 |
| LOVO | hu Colon Adenocarcinoma | 12.6 | 5.4 | 8.7 | 3.8 |
| MOLT4 | Lymph Leukemia | 12.7 | 0.0 | 7.3 | 0.0 |
| SHP-77 | hu Lung Small Cell Carcinoma | 12.8 | 5.9 | 6.6 | 2.7 |
| HCT-116 | hu Colon Carcinoma | 14.1 | 4.4 | 12.4 | 9.5 |
| HOP 18 | hu Lung Large Cell | 16.6 | 8.1 | 10.3 | 3.1 |
| A2780 | hu Ovary Adenocarcinoma | 20.7 | 2.8 | 7.5 | 1.0 |
| PC-3 | hu Prostate Carcinoma | 23.2 | 8.5 | 44.2 | 13.2 |
| SR | Leukemia | 24.4 | 0.0 | 20.9 | 0.0 |
| CHA-59 | hu Bone Osteosarcoma | 24.7 | 9.7 | 8.2 | 2.1 |
| PAN 02 | Pancreatic Ductal Carcinoma | 25.8 | 7.0 | 9.3 | 2.2 |
| MCF 7 | Breast adenocarcinoma | 26.7 | 19.8 | 11.1 | 5.8 |
| A498 | hu Renal Carcinoma | 28.5 | 12.4 | 35.3 | 33.4 |
| NCI-H460 | hu Lung Large Cell Carcinoma | 30.3 | 5.6 | 11.6 | 5.8 |
| CCRF-CEM | Lymph Leukemia | 46.2 | 1.8 | 41.3 | 2.0 |
| Median | | 7.4 | 1.8 | 2.8 | 1.0 |
| HEK 293 | Kidney | 20.2 | 20.1 | 13.6 | 4.5 |

Example 2

Seven matched pairs of tumor cell lines (one MBD high-uptake and one MBD low-uptake line for each tissue) were selected for further study. Of these, six pairs (all except the leukemia lines) were selected for gene array analysis.

TABLE 3

| TISSUE | HIGH-UPTAKE | LOW-UPTAKE |
|---|---|---|
| Prostate | PC-3 | DU-145 |
| Colon | HT-29 | HCT-15 |
| Lung | NCI-H23 | HOP-62 |
| Kidney | A498 | UO-31 |
| Ovary | OVCAR-8 | OVCAR-5 |
| Breast | MCF-7 | HS-578T |
| Leukemia | CCRF-CEM | K562 |

Total RNA was isolated using standard RNA purification protocols (Nucleospin RNA II). The RNA was quantified by photometrical measurement and the integrity checked by the Bioanalyzer 2100 system (Agilent Technologies, Palo Alto, Calif.). Based on electropherogram profiles, the peak areas of 28S and 18S RNA were determined and the ratio of 28S/18S was calculated. In all samples this value was greater than 1.5, indicating qualitative integrity of the RNAs. 1 μg total RNA was used for linear amplification (PIQOR™ Instruction Manual). Amplified RNA (aRNAs) were subsequently checked with the Bioanalyzer 2100 system. Samples yielded in every case >20 μg aRNA and showed a Gaussian-like distribution of the aRNA transcript lengths as expected (average transcript length 1.5 kB). This indicates successful amplification of the total RNA samples and good quality of the obtained aRNAs. All aRNAs were used for fluorescent label in PIQOR™ (Parallel Identification and quantification of RNAs) cDNA microarrays (Memorec Biotec GmbH, Cologne, Germany). cDNA microarray production, hybridization and evaluation were carried out as previously described [Bosio, A., Knorr, C., Janssen, U., Gebel, S., Haussmann, H. J., Muller, T., 2002. Kinetics of gene expression profiling in Swiss 3T3 cells exposed to aqueous extracts of cigarette smoke. Carcinogenesis 23, 741-748.]. Samples were labeled with FluoroLink™ Cy3/Cy5-dCTP (Amersham Pharmacia Biotech, Freiburg, Germany). 1 μg of amplified RNA for validation experiments were labeled and hybridized. All hybridizations were performed in quadruplicate. Quality controls, external controls and hybridization procedures and parameters were performed according to the manufacturer's instructions and comply to the MIAME standards. The Cy3 (sample) and Cy5 (reference) fluorescent labeled probes were hybridized on customized PIQOR™ Microarrays and subjected to overnight hybridization using a hybridization station. The arrays are designed to query genes previously implicated in processes relevant to cancer. These include 110 transcription factors, 153 extracellular matrix-related, 207 enzymes, 120 cell-cycle-related, 171 ligands/surface markers, and 368 signal transduction genes. Equal amounts of aRNA from the 12 respective cell lines were pooled and served as a reference against which each of the individual cell lines were hybridized.

Correlation analysis was carried out to identify those genes that might be implicated in the cellular physiological state most permissive for MBD-mediated uptake. Briefly, genes were sorted based on the fold change in expression (up or down) when pairwise comparison of the selected high and low MBD-mediated uptake lines was performed by tissue. Based on an average of these-fold changes across all pairs, approximately the top (up-regulated) and bottom (down-regulated) 3% of the gene list was selected for further analysis. The functional distribution of genes in these two groups is highly non-random, as shown in Table 4.

TABLE 4

| GENE CATEGORY | % ARRAY (n = 1129) | HIGH vs LOW MBD UPTAKE | |
|---|---|---|---|
| | | UP-REG (n = 32) | DN-REG (n = 32) |
| TRANSCRIPTION FACTORS | 9.7 | 40.6 | 0 |
| INTRACELLULAR PROTEINS | 18.3 | 25.0 | 0 |
| SIGNAL TRANSDUCTION (I) | 32.6 | 9.4 | 0 |
| CELL-CYCLE, DNA REPAIR | 10.6 | 0 | 0 |
| ECM-RELATED | 13.6 | 3.1 | 68.8 |
| SURFACE MARKERS/LIGANDS | 15.2 | 9.4 | 31.2 |

There is a notable difference in the functional distribution of up- and down-regulated genes. The former primarily include transcription factors and other select intracellular proteins whereas the latter are exclusively extracellular. Using correlation of expression patterns across all cell lines to further sort the subsets of up- and down-regulated genes, it is possible to identify 2-3 major groupings in each set. Up-regulated genes include GDF15, SRC, ATF3, HSPF3, FAPP2, PSMB9, PSMB10, c-JUN, JUN-B, HSPA1A, HSPA6, NFKB2, IRF1, WDR9A, MAZ, NSG-X, KIAA1856, BRF2, COL9A3, TPD52, TAX40, PTPN3, CREM, HCA58, TCFL5, CEBPB, IL6R and ABCP2. It is remarkable that at least one third of these genes have been previously associated with cellular responses to stress (e.g. GDF15, ATF3, HSPF3, PSMB9, PSMB10, c-JUN, JUN-B, HSPA1A, HSPA6, NFKB2, IRF1). Down-regulated genes include CTGF, LAMA4, LAMB3, IL6, IL1B, UPA, MMP2, LOX, SPARC, FBN1, LUM, PAI1, TGFB2, URB, TSP1, CSPG2, DCN, ITGA5, TKT, CAV1, CAV2, COL1A1, COL4A1, COL4A2, COL5A1, COL5A2, COL6A2, COL6A3, COL7A1, COL8A1, and IL7R.

The patterns of up- or down-regulation of the following genes (shown in Table 5) serve as illustrations. Table 3 shows the fold expression difference in pairwise comparisons.

TABLE 5

| GENE | Prostate | Colon | Lung | Kidney | Breast |
|---|---|---|---|---|---|
| GDF-15 | 104.0 | 8.3 | 15.0 | 17.7 | 2.8 |
| IRF1 | 7.2 | 7.3 | 1.1 | 3.2 | 1.3 |
| HSP1A1 | 2.4 | 1.3 | 3.8 | 3.7 | 10.1 |
| JUNB | 9.0 | 0.9 | 6.1 | 3.2 | 10.0 |
| TGFB2 | 0.24 | 0.85 | 0.08 | 0.71 | 0.07 |
| IL6 | 1.05 | 0.67 | 0.26 | 0.21 | 0.04 |
| SPARC | 9.67 | 0.67 | 0.02 | 0.23 | 0.00 |

Example 3

Figure 1B:
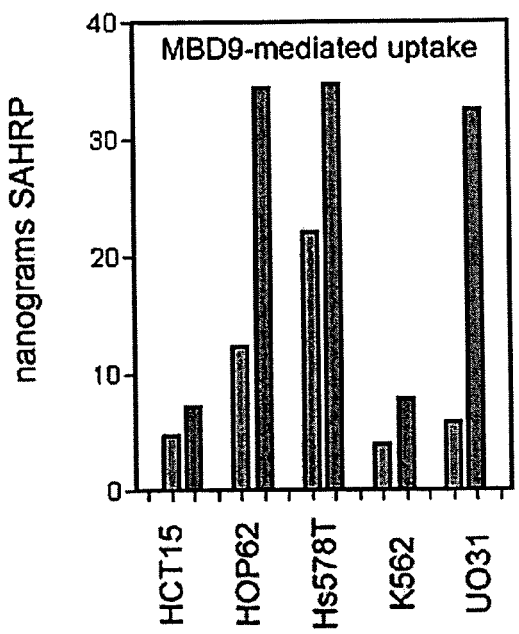
Figure 1C:
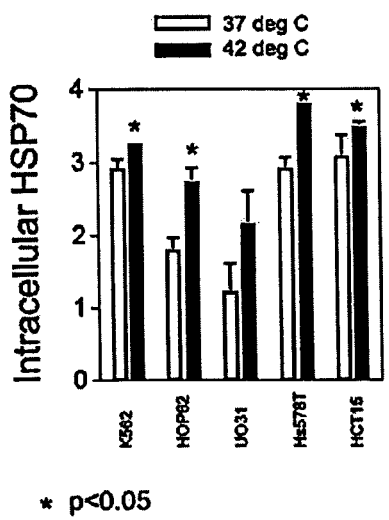
Figure 2:
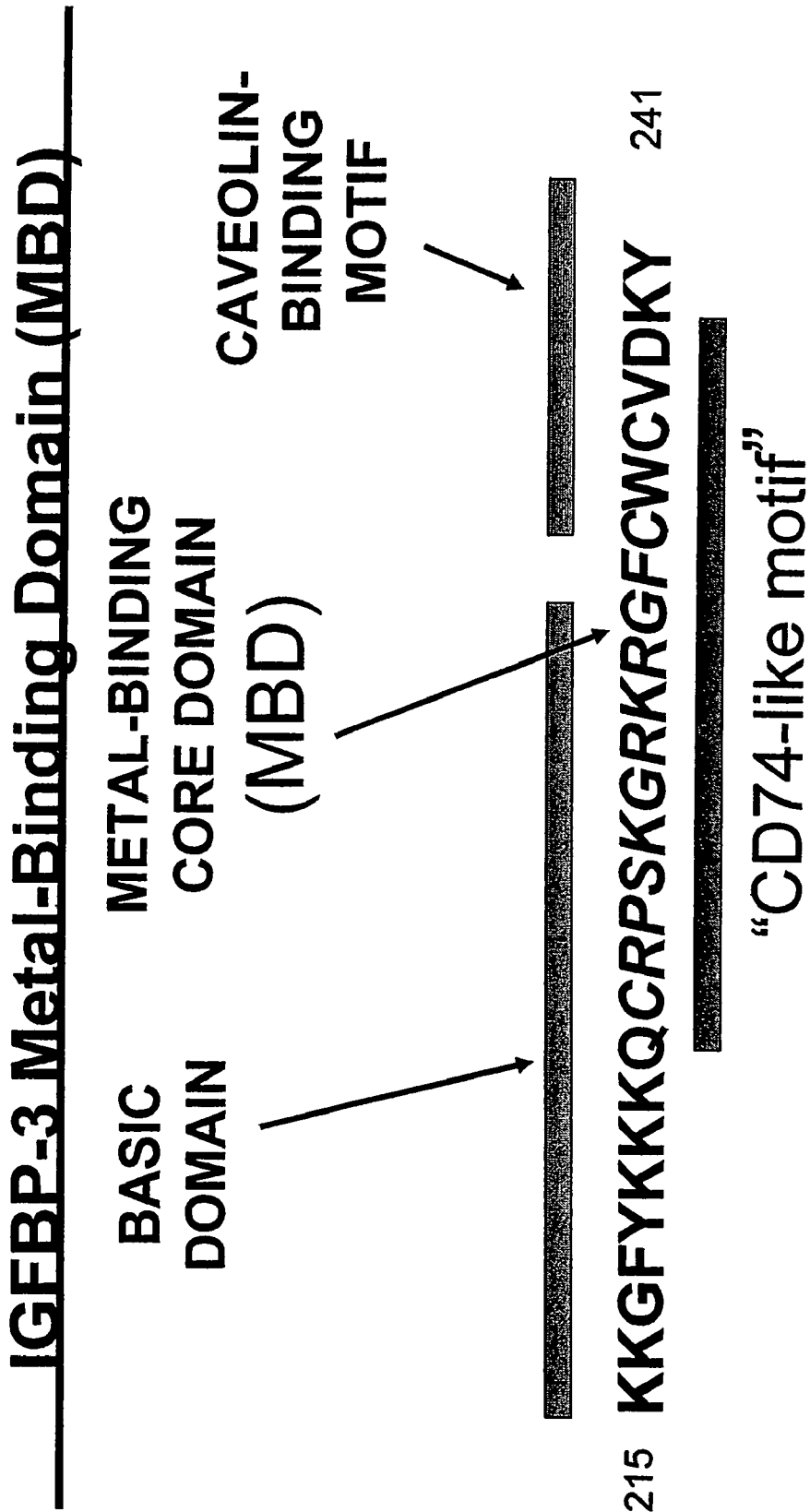
FIG. 2 shows the IGFBP-3 metal-binding domain (MBD) (SEQ ID NO: 176).
Figure 11:
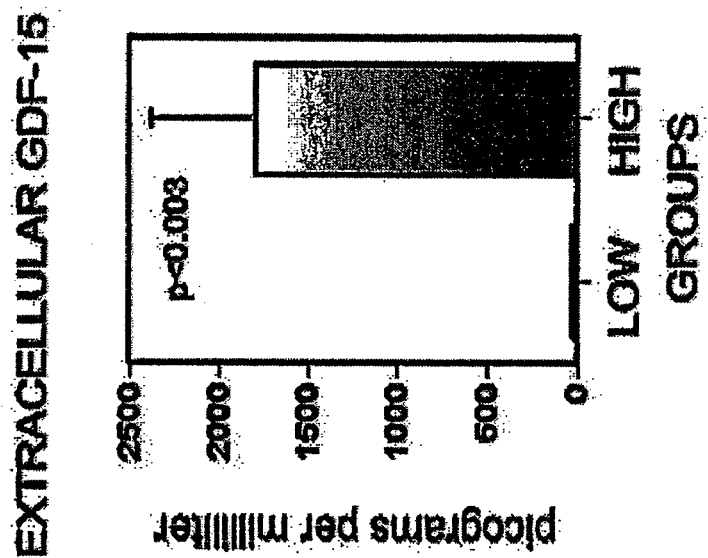
FIG. 11 shows average GDF-15/MIC-1/PLAB secretion by the high- and low-uptake cell lines of Table 3. There is a statistically significant difference between the high- and low-uptake cell line cohorts.
Figure 12:
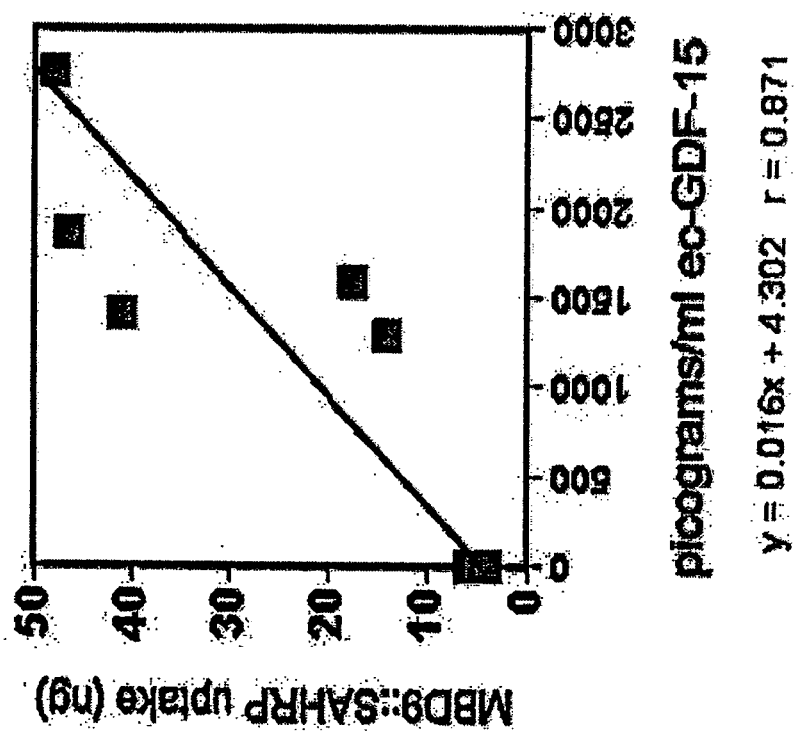
FIG. 12 shows GDF-15/MIC-1/PLAB levels are correlated (r=0.87) to MBD-mediated uptake in the same collection of cell lines reported in FIG. 11. Together with the results shown in FIG. 11, these results point to a potential usefulness of GDF15 as a diagnostic marker.
Figures 27A, 27B:
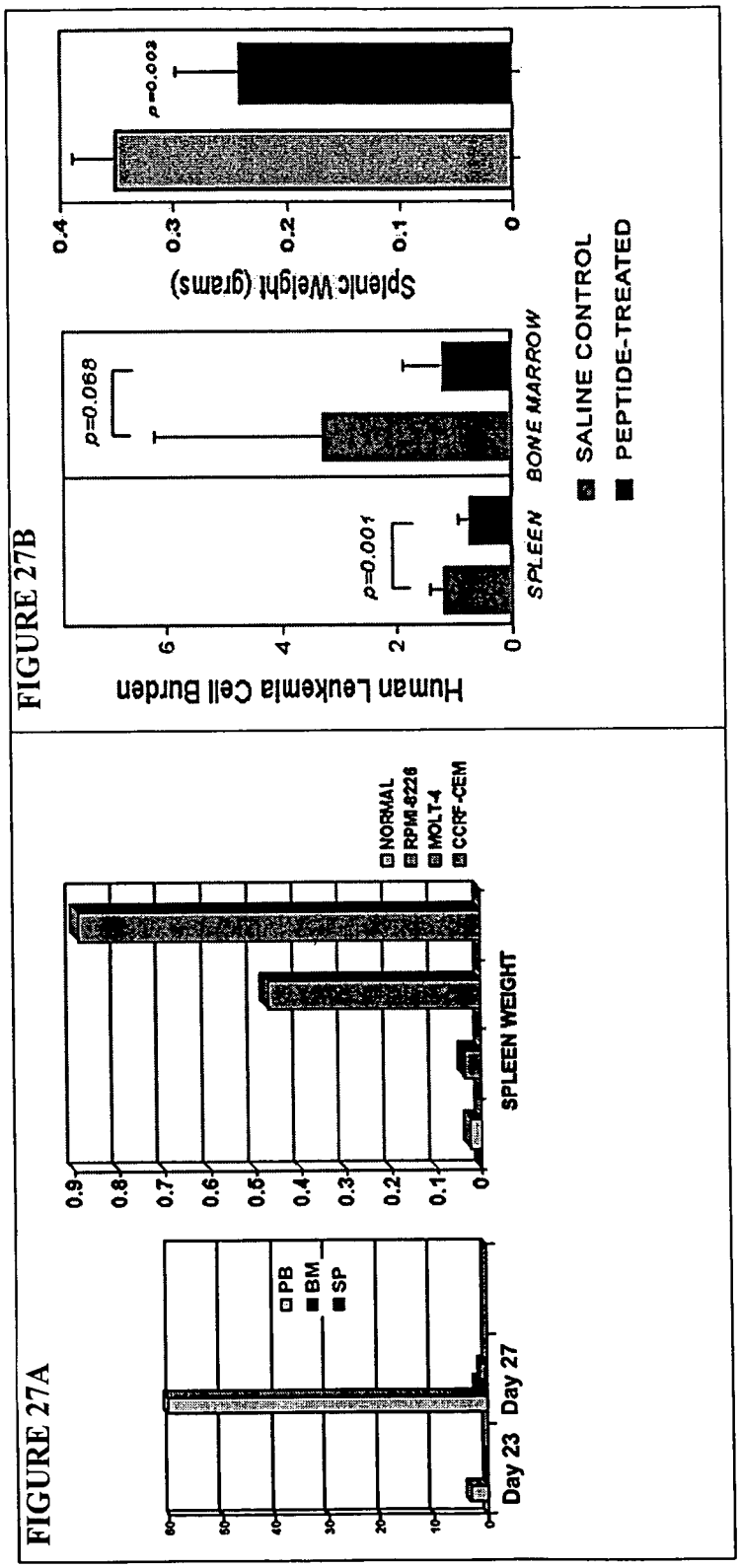
FIG. 27A—Left graph. Successful establishment of a leukemia model: Intracardial HL-60 cell injection into Rag-2 mice. Small but significant human cell-counts observed by day 23 post-inoculation. A 3% increase of human cells in PB was observed by FACS analysis and confirmed by anti-human HLA MAb staining. No increase of human cells was detected in BM or SP. At day 27 post HL-60 inoculation there were minimal levels of human cells in BM and SP, but an average increase of leukemia cells of about 60% compared to BM, SP or non-injected Rag-2 mice. Intracardial injection into Rag-2 mice with human leukemia cell lines (CCRF-CEM, MOLT-4, RPMI-8226) led to the establishment of an in vivo leukemia model appropriate for testing MBD-peptide cocktails.
FIG. 27B. PCR analysis of mouse tissues. Genomic DNA was extracted from bone marrow and spleens collected after a 7-day, once-a-day treatment with 4 mg/kg MBD-peptide cocktail injected IP. the peptide cocktail consisted of equal parts by weight of PEP2, NFCSK, MDOKB3 and MDOKSH peptides (16 days total). By hgDNA PCR (100 ng input genomic DNA/50 uL PCR amplification reaction, 25 cycles) a significant reduction in CCRF-CEM cell count was observed, compared to the negative control (saline injection). Splenomegaly was reduced in animals injected with MBD peptide versus animals injected with saline.

Low-uptake lines HCT-15, HOP-62, Hs578T, K562 and UO31 were heat-shocked at 42 degrees for 1 hour. HSP70 was induced by this treatment (FIG. 1C). Uptake of MBD-tagged peroxidase was measured in extracts from these cells (red bars, right) and from control cells at 37 degrees. Significantly higher uptake was seen in all cell lines upon heat shock, and this uptake was not due to increased permeability of cells as SAHRP control sample uptake was undetectable in all cases. Cells were grown in RPMI 1640 media +10% FBS+10 μm ferrous chloride until 85-90% confluency. They were trypsinized and removed from the plates. Cells were resuspended in the same media in 15 ml tubes and incubated at 42 degrees Celsius for one hour. There was a set of controls at 37 degrees Celsius for each cell line. Then 10 ul of each peptide complex was added to each tube (in duplicate) and incubated at 37 degrees Celsius for 20 minutes. After 20 minutes, the media was removed from the plates and the cells were washed with 1×PBS plus 1% calf serum twice. Extracts were made using NEPER Kit (Pierce Technology) and were assayed using the ELISA protocol for horseradish peroxidase. The cell extracts were prepared according to protocols provided with the nuclear extraction kits. Results are shown in FIGS. 1A and 1B. They show that heat shock increases uptake of MBD-mobilized SA-HRP.

Example 4

HEK293 cellular uptake of MBD9::SAHRP is stimulated by pre-treatment with stressors. Peroxidase activity was measured 20 minutes after addition of 100 ng/ml of MBD::SAHRP protein to the cell culture medium, as described in Example 1. All pretreatments were for 20 hours except for sample 5. The results of this experiment are shown in FIG. 21.

Sample Key: (1) 293 control (2) 293+30 ng/ml TNF-a (3) 293+25 mM D-glucose (4) 293+700 mM NaCl (5) 293+42 deg C., 1 hour (6) 293+200 uM Cobalt chloride (7) 293+200 uM hydrogen peroxide (8) 293+low (1%) serum (9) 293+300 nM thapsigargin (10) 293+100 uM ethanol.

Example 5

MBD-mediated protein mobilization into PC12 cells is stimulated by stressors used in models of PD. 6-OHDA or MPP+ treatment of PC12 cells dramatically stimulates uptake of MBD-mobilized horseradish peroxidase. PC12 cells cultured in RPMI 1640+FBS were pretreated with MPTP or 6-OHDA. Uptake of exogenously added MBD::SAHRP (100 ng/ml) was measured in nuclear and cytoplasmic extracts 20 minutes after addition of the protein to the cell culture medium. The results are shown in FIG. 22. They confirm that experimental stressors routinely used in experimental models of PD also stimulate cellular uptake of MBD-tagged proteins in PC12 cells.

Example 6

Combinations of stressors can have novel effects on cellular uptake of MBD-tagged proteins in HEK293 cells and can be modulated by IGF-I. HEK293 cells were grown in 1% serum (nutritional stress) and peroxidase activity was measured 20 minutes after addition of 100 ng/ml of MBD::SAHRP protein to the cell culture medium, as described in Example 1. All pretreatments with growth factors IGF-I or EGF (100 ng/ml) were for 2 hours, followed by the indicated stress treatment (heat shock at 42 degrees Celsius for 60 minutes or 200 uM Cobalt Chloride for 60 minutes to simulate anoxia). Uptake was measured at the end of the stress treatment. The results are shown in Table 6 below (p values shown are relative to the control without growth factor treatment; only significant p values are shown):

TABLE 6

| Secondary Stressor | Growth Factor | Uptake of MBD::SAHRP (ng) |
|---|---|---|
| NONE | NONE | 20.10 ± 1.22 |
| HEAT SHOCK | NONE | 4.71 ± 0.80 (p < 0.01) |

TABLE 6-continued

| Secondary Stressor | Growth Factor | Uptake of MBD::SAHRP (ng) |
|---|---|---|
| HEAT SHOCK | +IGF-I | 2.54 ± 0.54 (p = 0.023) |
| HEAT SHOCK | +EGF | 6.00 ± 0.56 |
| COBALT (ANOXIA) | NONE | 20.91 ± 1.22 |
| COBALT (ANOXIA) | +IGF-I | 25.29 ± 0.57 (p = 0.013) |
| COBALT (ANOXIA) | +EGF | 25.59 ± 1.02 (p = 0.008) |

Example 7

Combinations of stressors can have novel effects on cellular uptake of MBD-tagged proteins in MCF-7 cells and can be modulated by IGF-I. MCF-7 cells were grown in 1% serum (nutritional stress) and peroxidase activity was measured 20 minutes after addition of 100 ng/ml of MBD::SAHRP protein to the cell culture medium, as described in Example 1. All pretreatments with growth factors IGF-I or EGF (100 ng/ml) were for 2 hours, followed by the indicated stress treatment (heat shock at 42 degrees Celsius for 60 minutes or 200 uM Cobalt Chloride for 60 minutes to simulate anoxia). Uptake was measured at the end of the stress treatment. The results are shown in Table 7 below (p values shown are relative to the control without growth factor treatment in each group; only significant p values are shown):

TABLE 7

| Secondary Stressor | Growth Factor | Uptake of MBD::SAHRP (ng) |
|---|---|---|
| NONE | NONE | 20.63 ± 0.87 |
| HEAT SHOCK | NONE | 1.67 ± 1.11 (p < 0.01) |
| HEAT SHOCK | +IGF-I | 1.19 ± 0.21 |
| HEAT SHOCK | +EGF | 2.11 ± 1.50 |
| COBALT (ANOXIA) | NONE | 22.83 ± 0.73 (p = 0.030) |
| COBALT (ANOXIA) | +IGF-I | 20.71 ± 1.01 (p = 0.048) |
| COBALT (ANOXIA) | +EGF | 23.91 ± 0.72 |

Example 8

Peptide Bio-KGF binds shRNA: Bio-KGF peptide was synthesized by Genemed Synthesis, Inc. (S. San Francisco, Calif.) as a 40-mer containing an MBD sequence and an RNA-hairpin binding domain from the N-terminus of bacteriophage lambda N protein: Bio-KGF: ("N"-terminal biotin) . . . KGF YKK KQC RPS KGR KRG FCW AQT RRR ERR AEK QAQ WKA A . . . ("C" terminus) (SEQ ID NO: 11)

An shRNA designed to silence the human beclin gene was designed to include a hairpin sequence corresponding to the NutR box of bacteriophage lambda mRNA (the binding target for the Bio-KGF peptide) and was amplified using the Silencer™ siRNA
Construction Kit (Ambion) using conditions specified by the manufacturer. The sequence of the DNA oligonucleotide used for the kit transcription reaction was:

```
T7BECR:
5' . . . AG TTT GGC ACA ATC AAT AAC TTTTTC AGT TAT
TGA TTG TGC CAA ACT CCTGTCTC . . . 3' (SEQ ID NO:
12)
```

As a vector control for in vivo confirmation of siRNA efficacy, the following oligonucleotides were designed for cloning into the pGSU6 vector (BamHI-EcoRI)

```
BECF:
5' . . . GAT CGG CAG TTT GGC ACA ATC AAT AAC
TGAAAA AGT TAT TGA TTG TGC CAA ACT GTT TTT TGG AAG
. . . 3' (SEQ ID NO: 13)

BECR:
5' . . . AAT TCT TCC AAA AAA CAG TTT GGC ACA ATC
AAT AAC TTTTTC AGT TAT TGA TTG TGC CAA ACT GCG
. . . 3' (SEQ ID NO: 14)
```

Various molar excess amounts of Bio-KGF (ranging from 63 pg to 2 ug per well; similar results were obtained across this range) were attached to a Ni-NTA plate (Qiagen Inc., Carlsbad, Calif. for 1 hour and blocked overnight with 3% BSA at 4 degrees C. in the refrigerator, and washed with PBS/Tween and TE buffers. RNA dilutions were added in TE buffer, incubated for 30 min on shaker, then for 30 min on bench at room temperature. After one wash with TE buffer, Ribogreen reagent (Ribogreen RNA Quantitation Reagent and Kit from Molecular Probes/Invitrogen) was added to the wells, incubated 5 minutes, and fluorescence was read on a fluorescent plate reader. The results are listed in Table 8 (each number is a mean of eight readings):

TABLE 8

| ng shRNA per well | Ribogreen Fluorescence |
|---|---|
| 88 | 81819 ± 24656 |
| 44 | 42053 ± 12769 |
| 22 | 11924 ± 3650 |
| 11 | 6016 ± 2977 |
| 5.5 | 2058 ± 781 |
| 2.7 | 853 ± 600 |

The Bio-KGF peptide binds the shRNA containing the lambda nutR hairpin loop.

Example 9

Sequences of Therapeutic MBD Peptides

Therapeutic peptides incorporating the MBD motif can be created by making fusions of peptide sequences known to have appropriate intracellular biological activities with either the N- or C-terminus of the core MBD sequence. The following table (Table 9) lists peptides used in this study. Based on prior studies, peptide sequences were selected to target up-regulated stress proteins (such as hsp70) in cancer, as well as MDM2 interactions with P53, inflammation (NF-kappa-B, NEMO, CSK), and previously characterized cancer-specific targets such as survivin in and bcl-2.

TABLE 9

Amino acid sequences of therapeutic MBD peptides used in this study. MBD sequence is highlighted. All peptides have N-terminal biotin. Nuclear uptake of streptavidin-horseradish peroxidase into HEK293 cells was confirmed for every peptide.

| PEPTIDE | AMINO ACID SEQUENCE |
|---|---|
| PNC-28 | ETFSDLWKLLKKWKMRRNQFWVKVQRG (SEQ ID NO: 15) |
| PEP-1 | ETFSDLWKLLKKGFYKKKQCRPSKGRKRGFCW (SEQ ID NO: 16) |

TABLE 9-continued

Amino acid sequences of therapeutic MBD peptides used in this study. MBD sequence is highlighted. All peptides have N-terminal biotin. Nuclear uptake of streptavidin-horseradish peroxidase into HEK293 cells was confirmed for every peptide.

| PEPTIDE | AMINO ACID SEQUENCE |
|---|---|
| PEP-2 | ETFSDVWKLLKKGFYKKKQCRPSKGRKRGFCW (SEQ ID NO: 17) |
| PEP-3 | ETFSDIWKLLKKGFYKKKQCRPSKGRKRGFCW (SEQ ID NO: 18) |
| NFKB | KKGFYKKKQCRPSKGRKRGFCWAPVQRKRQKLMP (SEQ ID NO: 19) |
| NEMO | KKGFYKKKQCRPSKGRKRGFCWAALDWSWLQT (SEQ ID NO: 20) |
| CSK | KKGFYKKKQCRPSKGRKRGFCWAVAEYARVQKRK (SEQ ID NO: 21) |
| MAN | LKILLLRKQCRPSKGRKRGFCWAVDKYG (SEQ ID NO: 22) |
| CTLA4 | KKGFYKKKQCRPSKGRKRGFCWATGVYVKMPPTEP (SEQ ID NO: 23) |
| CD28 | KKGFYKKKQCRPSKGRKRGFCWAHSD(pY)MNMTPRRP (SEQ ID NO: 24) |
| PKCI | KKGFYKKKQCRPSKGRKRGFCWRFARKGALRQKNV (SEQ ID NO: 25) |
| VIVIT | KKGFYKKKQCRPSKGRKRGFCWGPHPVIVITGPHE (SEQ ID NO: 26) |
| NFCSK | KKGFYKKKQCRPSKGRKRGFCWAEYARVQRKRQKLMP (SEQ ID NO: 27) |
| NFNEMO | KKGFYKKKQCRPSKGRKRGFCWALDWSWLQRKRQKLM (SEQ ID NO: 28) |
| M9HSBP1 | KKGFYKKKQCRPSKGRKRGFCWARIDDMSSRIDDLEKNIADL (SEQ ID NO: 29) |
| M9HSBP2 | KKGFYKKKQCRPSKGRKRGFCWAVQTLLQQMQDKFQTMSDQI (SEQ ID NO: 30) |

Example 10

Effects of Exogenously Added Peptides on Cell Viability of Cultured Breast Cancer Cells Peptides were added at 24 and 48 hours of culture and results of cytotoxicity measured at 96 hours using XTT assay according to the manufacturer's instructions. All measurements were made in triplicate or quadruplicate. FIG. 23 shows the results obtained when 25 ug/ml of each peptide was added. Results are expressed in terms of cell viability relative to MBD9 peptide control.

Example 11

Effects of Exogenously Added Peptides on Cell Viability of Cultured Leukemia Cells Peptides were added at 24 and 48 hours of culture and results of cytotoxicity measured at 96 hours using XTT assay according to the manufacturer's instructions. All measurements were made in triplicate or quadruplicate. FIG. 24 shows the results obtained when 25 ug/ml of each peptide was added. Results are expressed in terms of cell viability relative to no peptide control.

Example 12

As shown in FIG. 25, there is demonstrable synergy of peptide PEP-3 with nutritional stress on MCF-7 breast cancer cells. PEP-3 was added at 25 ug/ml. Culture conditions were as described for Example 10 above.

Example 13

As shown in FIG. 26 additive effects can be shown for selected therapeutic peptides with some chemotherapeutic agents such as paclitaxel in MCF-7 breast cancer cells. Peptides were added at 25 ug/ml. Tamoxifen (1 mM; TAM) or paclitaxel (0.1 ug/ml; TAX) were added simultaneously. Culture conditions were as described for Example 10 above.

Example 14

Selective Action of Peptides on Cancer Cells Versus Normal Cells

Effects of peptides were compared using primary HMEC cells versus MCF-7 breast cancer cells or primary isolated CD4+ T-cells versus the CCRF-CEM leukemia line. All cells are human. Results of 48 hour cytotoxicity using 6.25 ug·ml added peptide are shown in Table 10 below:

TABLE 10

Selective cytotoxicity of therapeutic peptides on cancer cells.

| | BREAST | | | LEUKEMIA | |
|---|---|---|---|---|---|
| PEPTIDE ADDED | HMEC | MCF-7 | | T-CELLS | CCRF-CEM |
| | | Plate 1 | Plate 2 | | |
| NO PEPTIDE | | | | 100.0 ± 8.0 | 100.0 ± 5.2 |
| MBD9 CONTROL | 100.0 ± 11.4 | 100.0 ± 4.4 | 100.0 ± 5.4 | | |
| PEP-1 | 90.9 ± 4.5 | 84.1 ± 4.7** | 90.9 ± 5.1* | 106.4 ± 5.5 | 89.5 ± 4.2* |
| PEP-2 | 96.1 ± 2.3 | 86.8 ± 5.6* | 94.1 ± 6.8 | 103.8 ± 4.3 | 89.8 ± 5.4* |
| PEP-3 | 95.9 ± 9.9 | 83.9 ± 4.0** | 91.3 ± 2.1* | 102.1 ± 2.8 | 89.4 ± 7.9* |
| NFKB | 93.1 ± 5.6 | 75.9 ± 3.0** | 77.5 ± 4.8** | 100.3 ± 2.1 | 100.6 ± 4.5 |
| NEMO | 92.3 ± 9.2 | 67.5 ± 4.9** | 73.5 ± 4.0** | 100.1 ± 2.8 | 101.5 ± 14.4 |
| CSK | 94.4 ± 8.8 | 73.4 ± 5.3** | 79.9 ± 6.8** | 108.4 ± 4.9 | 94.5 ± 4.1 |
| NFCSK | 104.4 ± 7.4 | 78.4 ± 6.2** | 89.6 ± 4.3* | | |
| NFNEMO | 109.4 ± 8.5 | 77.8 ± 4.0** | 96.7 ± 4.2 | | |

TABLE 10-continued

Selective cytotoxicity of therapeutic peptides on cancer cells.

| PEPTIDE ADDED | BREAST | | | LEUKEMIA | |
| --- | --- | --- | --- | --- | --- |
| | HMEC | MCF-7 | | T-CELLS | CCRF-CEM |
| M9HSBP1 | 113.2 ± 6.1 | 78.6 ± 6.3** | 92.7 ± 3.6 | | |
| M9HSBP2 | 96.5 ± 2.8 | 65.5 ± 4.6** | 87.8 ± 5.0* | | |

*p < 0.05
**p < 0.01

Example 15

In order to test the hypothesis that cancer cells are specifically susceptible to targeted disruption of constitutively up-regulated stress-coping and anti-apoptotic mechanisms, MBD-tagged peptides were designed to inhibit either the synthesis, transport or action of inflammatory and heat-shock response proteins, as well as molecules involved in anti-apoptotic actions within cancer cells. Table 11A lists the sequences of synthesized peptides. Peptides were synthesized by Genemed Synthesis, Inc. with N-terminal biotin, and purified by HPLC.

TABLE 11A

Peptide sequences (all peptides have N-terminal biotin). For each peptide, the core MBD motif is shown in boldface type.

PEPTIDE #AA SEQUENCE

ANTI-INFLAMMATORY MECHANISMS

CSK      34  KKGFYKKKQCRPSKGRKRGFCWAVAEYARVQKRK
             (SEQ ID NO: 21)
NFKB     34  KKGFYKKKQCRPSKGRKRGFCWAPVQRKRQKLMP
             (SEQ ID NO: 19)
NEMO     34  KKGFYKKKQCRPSKGRKRGFCWAALDWSWLQT
             (SEQ ID NO: 20)
NFCSK    37  KKGFYKKKQCRPSKGRKRGFCWAEYARVQRKRQKLMP
             (SEQ ID NO: 27)
NFNEMO   37  KKGFYKKKQCRPSKGRKRGFCWALDWSWLQRKRQKLM
             (SEQ ID NO: 28)
VIVIT    35  KKGFYKKKQCRPSKGRKRGFCWGPHPVIVITGPHE
             (SEQ ID NO: 26)

ANTI-HEAT-SHOCK MECHANISMS

M9HSBP1  42  KKGFYKKKQCRPSKGRKRGFCWARIDDMSSRIDDLEKNI
             ADL (SEQ ID NO: 29)
M9HSBP2  42  KKGFYKKKQCRPSKGRKRGFCWAVQTLLQQMQDKFQTMS
             DQI (SEQ ID NO: 30)

ANTI-APOPTOTIC (PRO-SURVIVAL) MECHANISMS

PEP2     32  ETFSDVWKLLKKGFYKKKQCRPSKGRKRGFCW
             (SEQ ID NO: 17)
PEP3     32  ETFSDIWKLLKKGFYKKKQCRPSKGRKRGFCW
             (SEQ ID NO: 18)
MSURVN   37  AKPFYKKKQCRPSKGRKRGFCWGSSGLGEFLKLDRER
             (SEQ ID NO: 31)
MDOKB3   33  KKGFYKKKQCRPSKGRKRGFCWPYTLLRRYGRD
             (SEQ ID NO: 32)
MBDP85   28  EYREIDKRGFYKKKQCRPSKGRKRGFCW
             (SEQ ID NO: 33)
MDOKSH   31  KKGFYKKKQCRPSKGRKRGFCWKPLYWDLYE
             (SEQ ID NO: 34)
MTALB3   38  HDRKEFAKFEEERARAKKGFYKKKQCRPSKGRKRGFCW
             (SEQ ID NO: 35)

MBD-tagged peptides targeting stress-coping and anti-apoptotic mechanisms commonly upregulated in cancer exhibit selective cytoxicity to cancer cells without affecting their normal cell counterparts. Peptides shown to have a strong cytotoxic effect on cancer cells but not their human counterparts include PEP1, PEP2 and PEP3, which target the MDM2::P53 interface. Also, peptides such as NFKB and CSK are of interest, targeting stress-coping mechanisms such as inflammation. The breast cancer lines tested are HS578T, MX-1, MDA-MB231, MDA-MB435 and MCF7. Leukemia cell lines tested for cytotoxicity effects with these MBD-tagged peptides are CCRF-CEM, RPMI-8226 and MOLT-4. Overall, MCF-7 and CCRF-CEM yield the most consistent data and the strongest effect across the board (Table 12). In addition, elevated levels of cytotoxicity are observed when multiple peptides are combined while keeping the overall amount of peptide added constant. Cytotoxicity increases with the number of peptides added per cocktail and is further enhanced by combining peptide cocktail treatment with paclitaxel.

Additional peptides were synthesized by Pepscan Systems B.V. (Lelystad, Holland) for testing of mutant variations in the original peptide sequences, and new sequences. These peptides are listed in Table 11B.

TABLE 11B

Peptide sequences synthesized by Pepscan Systems BV. N-terminii were biotinylated.

ORIGINAL
PEPTIDE(S)    NEW PEPTIDE SEQUENCES

1. Anti-       RENLRIALRYYKKKQCRPSKGRKRGFCW
               (SEQ ID NO: 36)
   inflam-     RESLRNLRGYYKKKQCRPSKGRKRGFCW
   matory      (SEQ ID NO: 37)

2. MDOKSH      KKGFYKKKQCRPSKGRKRGFCWKPLYWDLYE
               (SEQ ID NO: 34)
               KKGFYKKKQCRPSKGRKRGFCWKALYWDLYE
               (SEQ ID NO: 38)
               KGFYKKKQCRPSKGRKRGFCWKALYWDLYE
               (SEQ ID NO: 39)
               KGFYKKKQCRPSKGRKRGFCWKALYWDLYEM
               (SEQ ID NO: 40)
               KGFYKKKQCRPSKGRKRGFCWAALYWDLYEM
               (SEQ ID NO: 41)
               KGFYKKKQCRPSKGRKRGFCWALYWDLYEM
               (SEQ ID NO: 42)
               KGFYKKKQCRPSKGRKRGFCWALYWALYEM
               (SEQ ID NO: 43)

3. NFKB        KGFYKKKQCRPSKGRKRGFCWAPVQRKRQKLMP
               (SEQ ID NO: 44)
               KKGFYKKKQCRPSKGRKRGFCWAPVQRKRQKLMP
               (SEQ ID NO: 19)
               KKGFYKKKQCRPSKGRKRGFCWAVQRKRQKLMP
               (SEQ ID NO: 45)

TABLE 11B-continued

Peptide sequences synthesized by Pepscan Systems BV. N-terminii were biotinylated.

| ORIGINAL PEPTIDE(S) | NEW PEPTIDE SEQUENCES |
| --- | --- |
| 4. CSK | KGFYKKKQCRPSKGRKRGFCWAVAEYARVQKRK (SEQ ID NO: 46) |
|  | KGFYKKKQCRPSKGRKRGFCWAVALYARVQKRK (SEQ ID NO: 47) |
|  | VAEYARVQKRKGFYKKKQCRPSKGRKRGFCW (SEQ ID NO: 48) |
|  | VALYARVQKRKGFYKKKQCRPSKGRKRGFCW (SEQ ID NO: 49) |
| 5. MSURV | AKPFYKKKQCRPSKGRKRGFCWGSSSGLGEFLKLDRER (SEQ ID NO: 31) |
|  | AKPFYKKKQCRPSKGRKRGFCWASGLGEFLKLDRER (SEQ ID NO: 50) |
|  | AKPFYKKKQCRPSKGRKRGFCWAGLGEFLKLDRER (SEQ ID NO: 51) |
|  | AKPFYKKKQCRPSKGRKRGFCWGSSSGLGEFLKLDREA (SEQ ID NO: 52) |
|  | AKPFYKKKQCRPSKGRKRGFCWGSSSGLGEFLKLDRAR (SEQ ID NO: 53) |
|  | AKPFYKKKQCRPSKGRKRGFCWGSSSGLGEFLKLDAER (SEQ ID NO: 54) |
|  | AKPFYKKKQCRPSKGRKRGFCWGSSSGLGEFLKLARER (SEQ ID NO: 55) |
|  | AKPFYKKKQCRPSKGRKRGFCWGSSSGLGEFLKADRER (SEQ ID NO: 56) |
|  | AKPFYKKKQCRPSKGRKRGFCWGSSSGLGEFLALDRER (SEQ ID NO: 57) |
|  | AKPFYKKKQCRPSKGRKRGFCWGSSSGLGEFAKLDRER (SEQ ID NO: 58) |
|  | AKPFYKKKQCRPSKGRKRGFCWGSSSGLGEALKLDRER (SEQ ID NO: 59) |
|  | AKPFYKKKQCRPSKGRKRGFCWGSSSGLGAFLKLDRER (SEQ ID NO: 60) |
|  | AKPFYKKKQCRPSKGRKRGFCWGSSSGLAEFLKLDRER (SEQ ID NO: 61) |
|  | AKPFYKKKQCRPSKGRKRGFCWGSSGAGEFLKLDRER (SEQ ID NO: 62) |
| 6. INGAP | KKGFYKKKQCRPSKGRKRGFCWAIGLHDPSHGTLPNGS (SEQ ID NO: 63) |
|  | KKGFYKKKQCRPSKGRKRGFCWAIGLHAPSHGTLPNGS (SEQ ID NO: 64) |
|  | KKGFYKKKQCRPSKGRKRGFCWAIGLHDPSHGTLPNG (SEQ ID NO: 65) |
|  | IGLHDPSHGTLPNGSKKGFYKKKQCRPSKGRKRGFCW (SEQ ID NO: 66) |
|  | IGLHAPSHGTLPNGSKKGFYKKKQCRPSKGRKRGFCW (SEQ ID NO: 67) |
|  | IGLHDPSHGTLPNGFYKKKQCRPSKGRKRGFCW (SEQ ID NO: 68) |
| 7. MBD9 | KKGFYKKKQCRPSKGRKRGFCW (SEQ ID NO: 9) |
|  | KGFYKKKQCRPSKGRKRGFCW (SEQ ID NO: 69) |
| 8. M9HSBP1 | KGFYKKKQCRPSKGRKRGFCWARIDDMSSRIDDLEKNIADL (SEQ ID NO: 70) |
|  | KGFYKKKQCRPSKGRKRGFCWAAIDDMSSRIDDLEKNIADL (SEQ ID NO: 71) |
|  | KGFYKKKQCRPSKGRKRGFCWARADDMSSRIDDLEKNIADL (SEQ ID NO: 72) |
|  | KGFYKKKQCRPSKGRKRGFCWARIADMSSRIDDLEKNIADL (SEQ ID NO: 73) |
|  | KGFYKKKQCRPSKGRKRGFCWARIDAMSSRIDDLEKNIADL (SEQ ID NO: 74) |
|  | KGFYKKKQCRPSKGRKRGFCWARIDDASSRIDDLEKNIADL (SEQ ID NO: 75) |
|  | KGFYKKKQCRPSKGRKRGFCWARIDDMASRIDDLEKNIADL (SEQ ID NO: 76) |
|  | KGFYKKKQCRPSKGRKRGFCWARIDDMSARIDDLEKNIADL (SEQ ID NO: 77) |
|  | KGFYKKKQCRPSKGRKRGFCWARIDDMSSRIDDLAKNIADL (SEQ ID NO: 78) |
|  | KGFYKKKQCRPSKGRKRGFCWARIDDMSSRIDDLEANIADL (SEQ ID NO: 79) |
|  | KGFYKKKQCRPSKGRKRGFCWARIDDMSSRIDDLEKAIADL (SEQ ID NO: 80) |
|  | KGFYKKKQCRPSKGRKRGFCWARIDDMSSRIDDLEKNIAD (SEQ ID NO: 81) |
|  | KGFYKKKQCRPSKGRKRGFCWARIDDMSSRIDDLEKNIA (SEQ ID NO: 82) |
|  | KGFYKKKQCRPSKGRKRGFCWARIDDMSSRIDDLEKNI (SEQ ID NO: 83) |
|  | KGFYKKKQCRPSKGRKRGFCWARIDDMSSRIDDLEKN (SEQ ID NO: 84) |
|  | KGFYKKKQCRPSKGRKRGFCWAIDDMSSRIDDLEKNIADL (SEQ ID NO: 85) |
|  | KGFYKKKQCRPSKGRKRGFCWAIDDMSSRIDDLEKNI (SEQ ID NO: 86) |
| 9. PEP3 | ETFSDIWKLLKKGFYKKKQCRPSKGRKRGFCW (SEQ ID NO: 18) |
|  | ETFSDIWKLLKGFYKKKQCRPSKGRKRGFCW (SEQ ID NO: 87) |
|  | ETFSDIWKLLAKGFYKKKQCRPSKGRKRGFCW (SEQ ID NO: 88) |
|  | ETFSDIWKLLKKGFYKKKQCRPSKGRKRGFCW (SEQ ID NO: 18) |
|  | ETFSDIWKLAKKGFYKKKQCRPSKGRKRGFCW (SEQ ID NO: 89) |
|  | ETFSDIWKALKKGFYKKKQCRPSKGRKRGFCW (SEQ ID NO: 90) |
|  | ETFSDIWALLKKGFYKKKQCRPSKGRKRGFCW (SEQ ID NO: 91) |
|  | ETFSDIAKLLKKGFYKKKQCRPSKGRKRGFCW (SEQ ID NO: 92) |
|  | ETFSDAWKLLKKGFYKKKQCRPSKGRKRGFCW (SEQ ID NO: 93) |
|  | ETFSAIWKLLKKGFYKKKQCRPSKGRKRGFCW (SEQ ID NO: 94) |
|  | ETFADIWKLLKKGFYKKKQCRPSKGRKRGFCW (SEQ ID NO: 95) |
|  | ETASDIWKLLKKGFYKKKQCRPSKGRKRGFCW (SEQ ID NO: 96) |
|  | EAFSDIWKLLKKGFYKKKQCRPSKGRKRGFCW (SEQ ID NO: 97) |
|  | ATFSDIWKLLKKGFYKKKQCRPSKGRKRGFCW (SEQ ID NO: 98) |
|  | DETFSDIWKLLKKGFYKKKQCRPSKGRKRGFCW (SEQ ID NO: 99) |
|  | FETFSDIWKLLKKGFYKKKQCRPSKGRKRGFCW (SEQ ID NO: 100) |
|  | GETFSDIWKLLKKGFYKKKQCRPSKGRKRGFCW (SEQ ID NO: 101) |
|  | HETFSDIWKLLKKGFYKKKQCRPSKGRKRGFCW (SEQ ID NO: 102) |
|  | IETFSDIWKLLKKGFYKKKQCRPSKGRKRGFCW (SEQ ID NO: 103) |
|  | KETFSDIWKLLKKGFYKKKQCRPSKGRKRGFCW (SEQ ID NO: 104) |
|  | LETFSDIWKLLKKGFYKKKQCRPSKGRKRGFCW (SEQ ID NO: 105) |
|  | METFSDIWKLLKKGFYKKKQCRPSKGRKRGFCW (SEQ ID NO: 106) |
|  | NETFSDIWKLLKKGFYKKKQCRPSKGRKRGFCW (SEQ ID NO: 107) |
|  | PETFSDIWKLLKKGFYKKKQCRPSKGRKRGFCW (SEQ ID NO: 108) |
|  | QETFSDIWKLLKKGFYKKKQCRPSKGRKRGFCW (SEQ ID NO: 109) |
|  | RETFSDIWKLLKKGFYKKKQCRPSKGRKRGFCW (SEQ ID NO: 110) |
|  | SETFSDIWKLLKKGFYKKKQCRPSKGRKRGFCW (SEQ ID NO: 111) |

TABLE 11B-continued

Peptide sequences synthesized by Pepscan
Systems BV. N-terminii were biotinylated.

| ORIGINAL PEPTIDE(S) | NEW PEPTIDE SEQUENCES |
|---|---|
| | TETFSDIWKLLKKGFYKKKQCRPSKGRKRGFCW (SEQ ID NO: 112) |
| | VETFSDIWKLLKKGFYKKKQCRPSKGRKRGFCW (SEQ ID NO: 113) |
| | WETFSDIWKLLKKGFYKKKQCRPSKGRKRGFCW (SEQ ID NO: 114) |
| | YETFSDIWKLLKKGFYKKKQCRPSKGRKRGFCW (SEQ ID NO: 115) |
| 10. M9HSBP2 | KGFYKKKQCRPSKGRKRGFCWAVQTLLQQMQDKFQTMSDQI (SEQ ID NO: 116) |
| | KGFYKKKQCRPSKGRKRGFCWAVQTLLQQMQDKFQTMSDQ (SEQ ID NO: 117) |
| | KGFYKKKQCRPSKGRKRGFCWAVQTLLQQMQDKFQTMSD (SEQ ID NO: 118) |
| | KGFYKKKQCRPSKGRKRGFCWAVQTLLQQMQDKFQTMS (SEQ ID NO: 119) |
| | KGFYKKKQCRPSKGRKRGFCWAQTLLQQMQDKFQTMSDQI (SEQ ID NO: 120) |
| | KGFYKKKQCRPSKGRKRGFCWATLLQQMQDKFQTMSDQI (SEQ ID NO: 121) |
| | KGFYKKKQCRPSKGRKRGFCWALLQQMQDKFQTMSDQI (SEQ ID NO: 122) |
| | KGFYKKKQCRPSKGRKRGFCWAVQTLLQQMQAKFQTMSDQI (SEQ ID NO: 123) |
| | KGFYKKKQCRPSKGRKRGFCWAVQTLLQQMQDKFQTMSAQI (SEQ ID NO: 124) |
| | KGFYKKKQCRPSKGRKRGFCWALLQQMQDKFQTMS (SEQ ID NO: 125) |

TABLE 11C

Additional peptides synthesized by Genemed Inc.
All peptides except AICSKBB35 and HSBB41 are
N-terminally biotinylated.

| PEPTIDE | SEQUENCE |
|---|---|
| AICSK40 | RESLRNLRGYYKKKQCRPSKGRKRGFCWAVAEYARVQKRK (SEQ ID NO: 126) |
| AICSKBB35 | RESLRNLRGYYKCNWAPPFKARCAVAEYARVQKRK (SEQ ID NO: 127) |

TABLE 11C-continued

Additional peptides synthesized by Genemed Inc.
All peptides except AICSKBB35 and HSBB41 are
N-terminally biotinylated.

| PEPTIDE | SEQUENCE |
|---|---|
| PEP3DOK41 | LETFSDIWKLLKGFYKKKQCRPSKGRKRGFCWALYWDLYEM (SEQ ID NO: 128) |
| M2SURV37 | AKPFYKKKQCRPSKGRKRGFCWGSSGLAEFLKLDRER (SEQ ID NO: 61) |
| HSBB41 | LLQQMQDKFQTMSCNWAPPFKAVCGRIDAMSSRIDDLEKNI (SEQ ID NO: 129) |
| MHBX34 | IRLKVFVLGGSRHKGFYKKKQCRPSKGRKRGFCW (SEQ ID NO: 130) |

As shown in FIG. 28, MBD-tagged antibodies are readily taken up by cancer cells. In the experiment shown on FIG. 28, complexes were made up using the following ratio: 1 ug of MBD peptide (SMZ or PEP3) to 5 ug streptavidin (Sigma). The mixture was incubated for twenty minutes at 37 C. Then 15 ug anti-stretptavidin antibody (Sigma) was added and the mixture was incubated for twenty minutes at 37 C. A negative control consisting of streptavidin and anti-streptavidin only (minus peptides) was also set up. MCF-7 cells (ATCC) were grown up to 90-95% confluency. 10 ug complex was added per 100 mm plate of cells and incubated at 37 C for 20 minutes. Supernatent was removed and cells were washed with 1×PBS two times. Cells were incubated five minutes with 2 mls 0.25% trypsin (VWR) then washed with 1×PBS+ 5% FBS (VWR). Cells were centrifuged at 1100 rpm or five minutes and supernatant was removed. Cells were placed on ice. Nuclear and cytoplasmic extracts were made using a kit from Pierce Biotechnology and then protein concentration was determined. Nuclear and cytoplasmic extracts were incubated for one hour a room temperature in a 96 well plate. After incubation the plate was washed three times with 1×PBS+ Tween. 3% BSA was added to cover the wells and incubated at 4 degrees C. overnight. The next morning the plate was washed three times with 1×PBS+Tween then a goat anti-rabbit IgG-alkaline phosphatase conjugate (Pierce Biotechnology) was added for one hour at room temperature. After one hour, the plate was washed three times with 1×PBS+ tween and 1-step PNPP (Pierce Biotechnology) was added for thirty minutes. The plate was read at 405 nm.

TABLE 12

Cytotoxicity of MBD therapeutic peptides. Percent cell viabilities
that were significantly lower (p < 0.05) relative to control cells
treated with an equal dose of control MBD peptide are shown (data from
1–4 representative experiments).

| PEPTIDE/ MECHANISM | LEUKEMIA LINE (% viability @ 48 hr/25 ug/ml peptide) | | | | BREAST CANCER LINE (% viability @ 48 hr/25 ug/ml peptide) | | | | |
|---|---|---|---|---|---|---|---|---|---|
| | CCRF-CEM | MOLT-4 | SR | RPMI-8826 | MCF-7 | MDA-MB231 | MDA-MB435 | Hs578T | MX-I |
| | | | | INFLAMMATORY | | | | | |
| CSK | 75.1 ± 4.5 | 81.0 ± 7.1 | | | 21.1 ± 4.1 | | | 50.2 ± 1.6 | |
| | 85.5 ± 2.3 | 54.8 ± 9.7 | | | 41.3 ± 5.8 | | | 76.3 ± 0.6 | |
| NFKB | 47.4 ± 13.9 | 35.9 ± 6.8 | | 64.6 ± 14.3 | 32.8 ± 17.7 | 91.6 ± 6.1 | 18.0 ± 1.6 | 36.3 ± 5.6 | 74.1 ± 6.1 |
| | | 22.5 ± 3.5 | | | | | 29.6 ± 2.6 | 30.6 ± 2.7 | |
| NEMO | | | 56.9 ± 6.2 | | 77.0 ± 46.7 | 79.0 ± 0.8 | 67.4 ± 21.1 | 81.3 ± 3.0 | 59.1 ± 3.2 |
| | | | | | | | 90.2 ± 3.6 | | |
| VIVIT | 72.1 ± 9.2 | 35.2 ± 4.3 | 63.3 ± 10.3 | 59.8 ± 19.2 | | | | | |

TABLE 12-continued

Cytotoxicity of MBD therapeutic peptides. Percent cell viabilities that were significantly lower ($p < 0.05$) relative to control cells treated with an equal dose of control MBD peptide are shown (data from 1–4 representative experiments).

| PEPTIDE/ MECHANISM | LEUKEMIA LINE (% viability @ 48 hr/25 ug/ml peptide) | | | | BREAST CANCER LINE (% viability @ 48 hr/25 ug/ml peptide) | | | | |
|---|---|---|---|---|---|---|---|---|---|
| | CCRF-CEM | MOLT-4 | SR | RPMI-8826 | MCF-7 | MDA-MB231 | MDA-MB435 | Hs578T | MX-I |
| HEAT SHOCK | | | | | | | | | |
| M9HSBP1 | | | | | 77.1 ± 20.3 | | | 77.7 ± 5.2 | |
| M9HSBP2 | 92.6 ± 2.0 | | | | 94.2 ± 17.1 | | 88.9 ± 4.0 | 81.7 ± 2.9 | |
| | | | | | | | 87.7 ± 6.7 | | |
| APOPTOTIC | | | | | | | | | |
| PEP2 | 71.7 ± 10.0 | 63.5 ± 7.7 | 33.7 ± 16.0 | 38.4 ± 4.2 | 19.3 ± 6.3 | 40.7 ± 1.8 | 18.5 ± 1.0 | 31.1 ± 3.0 | 6.8 ± 1.5 |
| | 5.9 ± 2.6 | 57.9 ± 1.3 | | | 33.5 ± 4.4 | | | 33.5 ± 2.3 | 9.0 ± 0.6 |
| | 80.0 ± 14.6 | 88.2 ± 2.6 | | | 35.6 ± 5.7 | | | | |
| PEP3 | 86.8 ± 3.1 | 73.0 ± 5.5 | 75.9 ± 15.7 | | 27.5 ± 15.2 | 32.9 ± 1.7 | 16.0 ± 2.0 | 18.6 ± 1.7 | |
| | 24.5 ± 8.3 | 58.3 ± 16.5 | | | 30.6 ± 5.7 | | 27.0 ± 3.9 | 55.1 ± 4.1 | |
| | 82.4 ± 7.1 | | | | 21.7 ± 1.5 | | | 33.2 ± 0.7 | |
| MSURVN | | | | | 52.3 ± 3.5 | 91.4 ± 3.3 | 93.8 ± 1.8 | 77.7 ± 4.7 | |
| | | | | | 64.7 ± 5.0 | | 86.0 ± 2.2 | | |
| MDOKB3 | | | | | 92.4 ± 5.4 | | 74.5 ± 1.8 | 77.6 ± 5.6 | |
| | | | | | 82.0 ± 5.9 | | 80.7 ± 22.8 | | |
| MDOKSH | 52.4 ± 12.6 | | | | 72.1 ± 8.2 | | | | |
| | 79.8 ± 3.7 | | | | | | | | |
| | 73.7 ± 12.7 | | | | | | | | |

In order to maximize the effects of cytotoxic peptides, alanine scanning of one peptide (MDOKSH) was undertaken as an illustration. 48 mutants were synthesized, purified and tested in CCRF-CEM and MCF-7. The cytotoxicity of the 48 peptides was strongly correlated in the two cell line assay systems (r=0.606). Some of the mutants synthesized and tested in CCRF-CEM and MCF-7 cells are shown in Table 13. Mutant #27 exhibits greatly enhanced cytotoxicity in both cell line assays. This result illustrates the general applicability of simple substitution and addition of residues, for example, alanine substitution one residue at a time, addition of one (of the 20) amino acid to each end of the peptide sequence, and deletion of one residue at a time. The core MBD sequence may, if desired, be excluded from the region to be explored by mutagenesis, in order to expedite the experiment.

TABLE 13

Up-mutants of MDOKSH peptide.

| PEPTIDE | SEQUENCE | CELL SURVIVAL* | |
|---|---|---|---|
| | | CCRF-CEM | MCF-7 |
| MDOKSH | KKGFYKKKQCRPSKGRKRGFCWKPLYWDLYE (SEQ ID NO: 34) | 100 | 100 |
| Mutant 6 | KKGFYKKKQCRPSKGRKRGFCWKPLYWD-LYEI (SEQ ID NO: 131) | 62.3 ± 5.0 | 68.5 ± 6.5 |
| Mutant 9 | KKGFYKKKQCRPSKGRKRGFCWKPLYWD-LYEM (SEQ ID NO: 132) | 63.8 ± 4.6 | 56.8 ± 8.1 |
| Mutant 11 | KKGFYKKKQCRPSKGRKRGFCWKPLYWD-LYEP (SEQ ID NO: 133) | 64.8 ± 7.2 | 59.6 ± 10.7 |
| Mutant 23 | KKGFYKKKQCRPSKGRKRGFCWKPLYWALYE (SEQ ID NO: 134) | 74.5 ± 8.0 | 58.8 ± 8.1 |
| Mutant 27 | KKGFYKKKQCRPSKGRKRGFCWKALYWDLYE (SEQ ID NO: 38) | 41.0 ± 5.1 | 38.8 ± 7.5 |
| Mutant 28 | KKGFYKKKQCRPSKGRKRGFCWAPLYWDLYE (SEQ ID NO: 135) | 60.1 ± 11.1 | 52.7 ± 11.7 |

TABLE 13-continued

Up-mutants of MDOKSH peptide.

| PEPTIDE | SEQUENCE | CELL SURVIVAL* CCRF-CEM | MCF-7 |
|---|---|---|---|
| Mutant 48 | AKGFYKKKQCRPSKGRKRGFCWKPLYWDLYE (SEQ ID NO: 136) | 71.8 ± 10.7 | 61.6 ± 3.1 |

*expressed relative to the activity of the parental peptide MDOKSH

TABLE 14

Therapeutic peptide sequences.

ETFSDLWKLLKKGFYKKKQCRPSKGRKRGFCW
(SEQ ID NO: 16)

ETFSDVWKLLKKGFYKKKQCRPSKGRKRGFCW
(SEQ ID NO: 17)

ETFSDIWKLLKKGFYKKKQCRPSKGRKRGFCW
(SEQ ID NO: 18)

KKGFYKKKQCRPSKGRKRGFCWAPVQRKRQKLMP
(SEQ ID NO: 19)

KKGFYKKKQCRPSKGRKRGFCWAALDWSWLQT
(SEQ ID NO: 20)

KKGFYKKKQCRPSKGRKRGFCWAVAEYARVQKRK
(SEQ ID NO: 21)

LKILLLRKQCRPSKGRKRGFCWAVDKYG
(SEQ ID NO: 22)

KKGFYKKKQCRPSKGRKRGFCWATGVYVKMPPTEP
(SEQ ID NO: 23)

KKGFYKKKQCRPSKGRKRGFCWAHSD(pY)MNMTPRRP
(SEQ ID NO: 24)

KKGFYKKKQCRPSKGRKRGFCWRFARKGALRQKNV
(SEQ ID NO: 25)

KKGFYKKKQCRPSKGRKRGFCWGPHPVIVITGPHE
(SEQ ID NO: 26)

KKGFYKKKQCRPSKGRKRGFCWAEYARVQRKRQKLMP
(SEQ ID NO: 27)

KKGFYKKKQCRPSKGRKRGFCWALDWSWLQRKRQKLM
(SEQ ID NO: 28)

KKGFYKKKQCRPSKGRKRGFCWARIDDMSSRIDDLEKNIADL
(SEQ ID NO: 29)

KKGFYKKKQCRPSKGRKRGFCWAVQTLLQQMQDKFQTMSDQI
(SEQ ID NO: 30)

AKGFYKKKQCRPSKGRKRGFCWKPLYWDLYE
(SEQ ID NO: 136)

KAGFYKKKQCRPSKGRKRGFCWKPLYWDLYE
(SEQ ID NO: 137)

KKAFYKKKQCRPSKGRKRGFCWKPLYWDLYE
(SEQ ID NO: 138)

KKGAYKKKQCRPSKGRKRGFCWKPLYWDLYE
(SEQ ID NO: 139)

KKGFAKKKQCRPSKGRKRGFCWKPLYWDLYE
(SEQ ID NO: 140)

KKGFYAKKQCRPSKGRKRGFCWKPLYWDLYE
(SEQ ID NO: 141)

KKGFYKAKQCRPSKGRKRGFCWKPLYWDLYE
(SEQ ID NO: 142)

KKGFYKKAQCRPSKGRKRGFCWKPLYWDLYE
(SEQ ID NO: 143)

KKGFYKKKACRPSKGRKRGFCWKPLYWDLYE
(SEQ ID NO: 144)

KKGFYKKKQCAPSKGRKRGFCWKPLYWDLYE
(SEQ ID NO: 145)

KKGFYKKKQCRASKGRKRGFCWKPLYWDLYE
(SEQ ID NO: 146)

KKGFYKKKQCRPAKGRKRGFCWKPLYWDLYE
(SEQ ID NO: 147)

KKGFYKKKQCRPSAGRKRGFCWKPLYWDLYE
(SEQ ID NO: 148)

KKGFYKKKQCRPSKARKRGFCWKPLYWDLYE
(SEQ ID NO: 149)

KKGFYKKKQCRPSKGARKRGFCWKPLYWDLYE
(SEQ ID NO: 150)

KKGFYKKKQCRPSKGRARGFCWKPLYWDLYE
(SEQ ID NO: 151)

KKGFYKKKQCRPSKGRKAGFCWKPLYWDLYE
(SEQ ID NO: 152)

KKGFYKKKQCRPSKGRKRAFCWKPLYWDLYE
(SEQ ID NO: 153)

KKGFYKKKQCRPSKGRKRGACWKPLYWDLYE
(SEQ ID NO: 154)

KKGFYKKKQCRPSKGRKRGFCAKPLYWDLYE
(SEQ ID NO: 155)

KKGFYKKKQCRPSKGRKRGFCWAPLYWDLYE
(SEQ ID NO: 135)

KKGFYKKKQCRPSKGRKRGFCWKALYWDLYE
(SEQ ID NO: 38)

KKGFYKKKQCRPSKGRKRGFCWKPAYWDLYE
(SEQ ID NO: 156)

KKGFYKKKQCRPSKGRKRGFCWKPLAWDLYE
(SEQ ID NO: 157)

KKGFYKKKQCRPSKGRKRGFCWKPLYADLYE
(SEQ ID NO: 158)

TABLE 14-continued

Therapeutic peptide sequences.

KKGFYKKKQCRPSKGRKRGFCWKPLYWALYE
(SEQ ID NO: 134)

KKGFYKKKQCRPSKGRKRGFCWKPLYWDAYE
(SEQ ID NO: 159)

KKGFYKKKQCRPSKGRKRGFCWKPLYWDLAE
(SEQ ID NO: 160)

KKGFYKKKQCRPSKGRKRGFCWKPLYWDLYA
(SEQ ID NO: 161)

KKGFYKKKQCRPSKGRKRGFCWKPLYWDLYE
(SEQ ID NO: 34)

KKGFYKKKQCRPSKGRKRGFCWKPLYWDLYEA
(SEQ ID NO: 162)

KKGFYKKKQCRPSKGRKRGFCWKPLYWDLYED
(SEQ ID NO: 163)

KKGFYKKKQCRPSKGRKRGFCWKPLYWDLYEF
(SEQ ID NO: 164)

KKGFYKKKQCRPSKGRKRGFCWKPLYWDLYEG
(SEQ ID NO: 165)

KKGFYKKKQCRPSKGRKRGFCWKPLYWDLYEH
(SEQ ID NO: 166)

KKGFYKKKQCRPSKGRKRGFCWKPLYWDLYEI
(SEQ ID NO: 131)

KKGFYKKKQCRPSKGRKRGFCWKPLYWDLYEW
(SEQ ID NO: 167)

KKGFYKKKQCRPSKGRKRGFCWKPLYWDLYEK
(SEQ ID NO: 168)

KKGFYKKKQCRPSKGRKRGFCWKPLYWDLYEL
(SEQ ID NO: 169)

KKGFYKKKQCRPSKGRKRGFCWKPLYWDLYEM
(SEQ ID NO: 132)

KKGFYKKKQCRPSKGRKRGFCWKPLYWDLYEN
(SEQ ID NO: 170)

KKGFYKKKQCRPSKGRKRGFCWKPLYWDLYEP
(SEQ ID NO: 133)

KKGFYKKKQCRPSKGRKRGFCWKPLYWDLYEQ
(SEQ ID NO: 171)

KKGFYKKKQCRPSKGRKRGFCWKPLYWDLYER
(SEQ ID NO: 172)

KKGFYKKKQCRPSKGRKRGFCWKPLYWDLYES
(SEQ ID NO: 173)

KKGFYKKKQCRPSKGRKRGFCWKPLYWDLYET
(SEQ ID NO: 174)

KKGFYKKKQCRPSKGRKRGFCWKPLYWDLYEV
(SEQ ID NO: 175)

KKGFYKKKQCRPSKGRKRGFCWKPLYWDLYEW
(SEQ ID NO: 167)

RENLRIALRYYKKKQCRPSKGRKRGFCW
(SEQ ID NO: 36)

RESLRNLRGYYKKKQCRPSKGRKRGFCW
(SEQ ID NO: 37)

KKGFYKKKQCRPSKGRKRGFCWKPLYWDLYE
(SEQ ID NO: 38)

TABLE 14-continued

Therapeutic peptide sequences.

KKGFYKKKQCRPSKGRKRGFCWKALYWDLYE
(SEQ ID NO: 39)

KGFYKKKQCRPSKGRKRGFCWKALYWDLYE
(SEQ ID NO: 40)

KGFYKKKQCRPSKGRKRGFCWKALYWDLYEM
(SEQ ID NO: 41)

KGFYKKKQCRPSKGRKRGFCWAALYWDLYEM
(SEQ ID NO: 42)

KGFYKKKQCRPSKGRKRGFCWALYWDLYEM
(SEQ ID NO: 43)

KGFYKKKQCRPSKGRKRGFCWAPVQRKRQKLMP
(SEQ ID NO: 44)

KKGFYKKKQCRPSKGRKRGFCWAPVQRKRQKLMP
(SEQ ID NO: 19)

KKGFYKKKQCRPSKGRKRGFCWAVQRKRQKLMP
(SEQ ID NO: 45)

KGFYKKKQCRPSKGRKRGFCWAVAEYARVQKRK
(SEQ ID NO: 46)

KGFYKKKQCRPSKGRKRGFCWAVALYARVQKRK
(SEQ ID NO: 47)

VAEYARVQKRKGFYKKKQCRPSKGRKRGFCW
(SEQ ID NO: 48)

VALYARVQKRKGFYKKKQCRPSKGRKRGFCW
(SEQ ID NO: 49)

AKPFYKKKQCRPSKGRKRGFCWGSSGLGEFLKLDRER
(SEQ ID NO: 31)

AKPFYKKKQCRPSKGRKRGFCWASGLGEFLKLDRER
(SEQ ID NO: 50)

AKPFYKKKQCRPSKGRKRGFCWAGLGEFLKLDRER
(SEQ ID NO: 51)

AKPFYKKKQCRPSKGRKRGFCWGSSGLGEFLKLDREA
(SEQ ID NO: 52)

AKPFYKKKQCRPSKGRKRGFCWGSSGLGEFLKLDRAR
(SEQ ID NO: 53)

AKPFYKKKQCRPSKGRKRGFCWGSSGLGEFLKLDAER
(SEQ ID NO: 54)

AKPFYKKKQCRPSKGRKRGFCWGSSGLGEFLKLARER
(SEQ ID NO: 55)

AKPFYKKKQCRPSKGRKRGFCWGSSGLGEFLKADRER
(SEQ ID NO: 56)

AKPFYKKKQCRPSKGRKRGFCWGSSGLGEFLALDRER
(SEQ ID NO: 57)

AKPFYKKKQCRPSKGRKRGFCWGSSGLGEFAKLDRER
(SEQ ID NO: 58)

AKPFYKKKQCRPSKGRKRGFCWGSSGLGEALKLDRER
(SEQ ID NO: 59)

AKPFYKKKQCRPSKGRKRGFCWGSSGLGAFLKLDRER
(SEQ ID NO: 60)

AKPFYKKKQCRPSKGRKRGFCWGSSGLAEFLKLDRER
(SEQ ID NO: 61)

AKPFYKKKQCRPSKGRKRGFCWGSSGAGEFLKLDRER
(SEQ ID NO: 62)

TABLE 14-continued

Therapeutic peptide sequences.

KKGFYKKKQCRPSKGRKRGFCWAIGLHDPSHGTLPNGS
(SEQ ID NO: 63)

KKGFYKKKQCRPSKGRKRGFCWAIGLHAPSHGTLPNGS
(SEQ ID NO: 64)

KKGFYKKKQCRPSKGRKRGFCWAIGLHDPSHGTLPNG
(SEQ ID NO: 65)

IGLHDPSHGTLPNGSKKGFYKKKQCRPSKGRKRGFCW
(SEQ ID NO: 66)

IGLHAPSHGTLPNGSKKGFYKKKQCRPSKGRKRGFCW
(SEQ ID NO: 67)

IGLHDPSHGTLPNGFYKKKQCRPSKGRKRGFCW
(SEQ ID NO: 68)

KGFYKKKQCRPSKGRKRGFCWARIDDMSSRIDDLEKNIADL
(SEQ ID NO: 70)

KGFYKKKQCRPSKGRKRGFCWAAIDDMSSRIDDLEKNIADL
(SEQ ID NO: 71)

KGFYKKKQCRPSKGRKRGFCWARADDMSSRIDDLEKNIADL
(SEQ ID NO: 72)

KGFYKKKQCRPSKGRKRGFCWARIADMSSRIDDLEKNIADL
(SEQ ID NO: 73)

KGFYKKKQCRPSKGRKRGFCWARIDAMSSRIDDLEKNIADL
(SEQ ID NO: 74)

KGFYKKKQCRPSKGRKRGFCWARIDDASSRIDDLEKNIADL
(SEQ ID NO: 75)

KGFYKKKQCRPSKGRKRGFCWARIDDMASRIDDLEKNIADL
(SEQ ID NO: 76)

KGFYKKKQCRPSKGRKRGFCWARIDDMSARIDDLEKNIADL
(SEQ ID NO: 77)

KGFYKKKQCRPSKGRKRGFCWARIDDMSSRIDDLAKNIADL
(SEQ ID NO: 78)

KGFYKKKQCRPSKGRKRGFCWARIDDMSSRIDDLEANIADL
(SEQ ID NO: 79)

KGFYKKKQCRPSKGRKRGFCWARIDDMSSRIDDLEKAIADL
(SEQ ID NO: 80)

KGFYKKKQCRPSKGRKRGFCWARIDDMSSRIDDLEKNIAD
(SEQ ID NO: 81)

KGFYKKKQCRPSKGRKRGFCWARIDDMSSRIDDLEKNIA
(SEQ ID NO: 82)

KGFYKKKQCRPSKGRKRGFCWARIDDMSSRIDDLEKNI
(SEQ ID NO: 83)

KGFYKKKQCRPSKGRKRGFCWARIDDMSSRIDDLEKN
(SEQ ID NO: 84)

KGFYKKKQCRPSKGRKRGFCWAIDDMSSRIDDLEKNIADL
(SEQ ID NO: 85)

KGFYKKKQCRPSKGRKRGFCWAIDDMSSRIDDLEKNI
(SEQ ID NO: 86)

ETFSDIWKLLKKGFYKKKQCRPSKGRKRGFCW
(SEQ ID NO: 18)

ETFSDIWKLLKGFYKKKQCRPSKGRKRGFCW
(SEQ ID NO: 87)

ETFSDIWKLLAKGFYKKKQCRPSKGRKRGFCW
(SEQ ID NO: 88)

TABLE 14-continued

Therapeutic peptide sequences.

ETFSDIWKLLKKGFYKKKQCRPSKGRKRGFCW
(SEQ ID NO: 18)

ETFSDIWKLAKKGFYKKKQCRPSKGRKRGFCW
(SEQ ID NO: 89)

ETFSDIWKALKKGFYKKKQCRPSKGRKRGFCW
(SEQ ID NO: 90)

ETFSDIWALLKKGFYKKKQCRPSKGRKRGFCW
(SEQ ID NO: 91)

ETFSDIAKLLKKGFYKKKQCRPSKGRKRGFCW
(SEQ ID NO: 92)

ETFSDAWKLLKKGFYKKKQCRPSKGRKRGFCW
(SEQ ID NO: 93)

ETFSAIWKLLKKGFYKKKQCRPSKGRKRGFCW
(SEQ ID NO: 94)

ETFADIWKLLKKGFYKKKQCRPSKGRKRGFCW
(SEQ ID NO: 95)

ETASDIWKLLKKGFYKKKQCRPSKGRKRGFCW
(SEQ ID NO: 96)

EAFSDIWKLLKKGFYKKKQCRPSKGRKRGFCW
(SEQ ID NO: 97)

ATFSDIWKLLKKGFYKKKQCRPSKGRKRGFCW
(SEQ ID NO: 98)

DETFSDIWKLLKKGFYKKKQCRPSKGRKRGFCW
(SEQ ID NO: 99)

FETFSDIWKLLKKGFYKKKQCRPSKGRKRGFCW
(SEQ ID NO: 100)

GETFSDIWKLLKKGFYKKKQCRPSKGRKRGFCW
(SEQ ID NO: 101)

HETFSDIWKLLKKGFYKKKQCRPSKGRKRGFCW
(SEQ ID NO: 102)

IETFSDIWKLLKKGFYKKKQCRPSKGRKRGFCW
(SEQ ID NO: 103)

KETFSDIWKLLKKGFYKKKQCRPSKGRKRGFCW
(SEQ ID NO: 104)

LETFSDIWKLLKKGFYKKKQCRPSKGRKRGFCW
(SEQ ID NO: 105)

METFSDIWKLLKKGFYKKKQCRPSKGRKRGFCW
(SEQ ID NO: 106)

NETFSDIWKLLKKGFYKKKQCRPSKGRKRGFCW
(SEQ ID NO: 107)

PETFSDIWKLLKKGFYKKKQCRPSKGRKRGFCW
(SEQ ID NO: 108)

QETFSDIWKLLKKGFYKKKQCRPSKGRKRGFCW
(SEQ ID NO: 109)

RETFSDIWKLLKKGFYKKKQCRPSKGRKRGFCW
(SEQ ID NO: 110)

SETFSDIWKLLKKGFYKKKQCRPSKGRKRGFCW
(SEQ ID NO: 111)

TETFSDIWKLLKKGFYKKKQCRPSKGRKRGFCW
(SEQ ID NO: 112)

VETFSDIWKLLKKGFYKKKQCRPSKGRKRGFCW
(SEQ ID NO: 113)

TABLE 14-continued

Therapeutic peptide sequences.

WETFSDIWKLLKKGFYKKKQCRPSKGRKRGFCW
(SEQ ID NO: 114)

YETFSDIWKLLKKGFYKKKQCRPSKGRKRGFCW
(SEQ ID NO: 115)

KGFYKKKQCRPSKGRKRGFCWAVQTLLQQMQDKFQTMSDQI
(SEQ ID NO: 116)

KGFYKKKQCRPSKGRKRGFCWAVQTLLQQMQDKFQTMSDQ
(SEQ ID NO: 117)

KGFYKKKQCRPSKGRKRGFCWAVQTLLQQMQDKFQTMSD
(SEQ ID NO: 118)

KGFYKKKQCRPSKGRKRGFCWAVQTLLQQMQDKFQTMS
(SEQ ID NO: 119)

KGFYKKKQCRPSKGRKRGFCWAQTLLQQMQDKFQTMSDQI
(SEQ ID NO: 120)

KGFYKKKQCRPSKGRKRGFCWATLLQQMQDKFQTMSDQI
(SEQ ID NO: 121)

KGFYKKKQCRPSKGRKRGFCWALLQQMQDKFQTMSDQI
(SEQ ID NO: 122)

KGFYKKKQCRPSKGRKRGFCWAVQTLLQQMQAKFQTMSDQI
(SEQ ID NO: 123)

TABLE 14-continued

Therapeutic peptide sequences.

KGFYKKKQCRPSKGRKRGFCWAVQTLLQQMQDKFQTMSAQI
(SEQ ID NO: 124)

KGFYKKKQCRPSKGRKRGFCWALLQQMQDKFQTMS
(SEQ ID NO: 125)

RESLRNLRGYYKKKQCRPSKGRKRGFCWAVAEYARVQKRK
(SEQ ID NO: 126)

RESLRNLRGYYKCNWAPPFKARCAVAEYARVQKRK
(SEQ ID NO: 127)

LETFSDIWKLLKGFYKKKQCRPSKGRKRGFCWALYWDLYEM
(SEQ ID NO: 128)

AKPFYKKKQCRPSKGRKRGFCWGSSGLAEFLKLDRER
(SEQ ID NO: 61)

LLQQMQDKFQTMSCNWAPPFKAVCGRIDAMSSRIDDLEKNI
(SEQ ID NO: 129)

IRLKVFVLGGSRHKGFYKKKQCRPSKGRKRGFCW
(SEQ ID NO: 130)

Although the foregoing invention has been described in some detail by way of illustration and example for purposes of clarity of understanding, the descriptions and examples should not be construed as limiting the scope of the invention.

---

I claim:

1. A polypeptide comprising the amino acid sequence ETFSDLWKLLKKGFYKKKQCRPSKGRKRGFCW (SEQ ID NO:16).

2. A composition comprising the polypeptide of claim 1 and a pharmaceutical excipient.

3. A nucleic acid encoding the polypeptide of claim 1.

4. A vector comprising the nucleic acid of claim 3.

5. A polypeptide comprising the amino acid sequence ETFSDVWKLLKKGFYKKKQCRPSKGRKRGFCW (SEQ TD NO:17).

6. A composition comprising the polypeptide of claim 5 and a pharmaceutical excipient.

7. A nucleic acid encoding the polypeptide of claim 5.

8. A vector comprising the nucleic acid of claim 7.

9. A polypeptide comprising the amino acid sequence ETFSDJWKLLKKGFYKKKQCRPSKGRKRGFCW (SEQ ID NO:18).

10. A composition comprising the polypeptide of claim 9 and a pharmaceutical excipient.

11. A nucleic acid encoding the polypeptide of claim 9.

12. A vector comprising the nucleic acid of claim 11.

* * * * *

UNITED STATES PATENT AND TRADEMARK OFFICE
CERTIFICATE OF CORRECTION

PATENT NO. : 7,618,816 B2  Page 1 of 1
APPLICATION NO. : 11/595367
DATED : November 17, 2009
INVENTOR(S) : Desmond Mascarenhas It is certified that error appears in the above-identified patent and that said Letters Patent is hereby corrected as shown below:

Col. 132, in Claim 9, line 2, please replace the sequence

"ETFSDJWKLLKKGFYKKKQCRPSKGRKRGFCW" with the sequence

--ETFSDIWKLLKKGFYKKKQCRPSKGRKRGFCW--.

Signed and Sealed this

Twenty-seventh Day of April, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,618,816 B2 | Page 1 of 1 |
| APPLICATION NO. | : 11/595367 | |
| DATED | : November 17, 2009 | |
| INVENTOR(S) | : Desmond Mascarenhas | |

It is certified that error appears in the above-identified patent and that said Letters Patent is hereby corrected as shown below:

Col. 132, in Claim 9, line 56, please replace the sequence

"ETFSDJWKLLKKGFYKKKQCRPSKGRKRGFCW" with the sequence

--ETFSDIWKLLKKGFYKKKQCRPSKGRKRGFCW--.

This certificate supersedes the Certificate of Correction issued April 27, 2010.

Signed and Sealed this

Eighteenth Day of May, 2010

David J. Kappos
*Director of the United States Patent and Trademark Office*